United States Patent [19]

Costanzo et al.

[11] Patent Number: 5,523,308
[45] Date of Patent: Jun. 4, 1996

[54] PEPTIDYL HETEROCYCLES USEFUL IN THE TREATMENT OF THROMBIN RELATED DISORDERS

[76] Inventors: Michael J. Costanzo, 14 Breckenridge Dr., Ivyland, Pa. 18974; Bruce E. Maryanoff, 3204 Aquetong Rd., New Hope, Pa. 18938

[21] Appl. No.: 486,473

[22] Filed: Jun. 7, 1995

[51] Int. Cl.$^6$ .................. A61K 31/445; C07D 417/06; C07D 413/06
[52] U.S. Cl. .................. 514/317; 514/321; 546/198; 546/209
[58] Field of Search .................. 546/209, 198; 514/321, 317

[56] References Cited

U.S. PATENT DOCUMENTS 5,476,861  12/1995  Carr et al. .................. 514/321

*Primary Examiner*—Johann Richter
*Assistant Examiner*—Laura R. Cross
*Attorney, Agent, or Firm*—Ralph R. Palo

[57] ABSTRACT

Compounds of the Formula I:

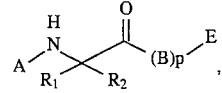

useful in the treatment of thrombin and trypsin related disorders.

40 Claims, No Drawings

PEPTIDYL HETEROCYCLES USEFUL IN THE TREATMENT OF THROMBIN RELATED DISORDERS

This invention relates a series of peptidyl heterocycles, intermediates used in their manufacture and pharmaceutical compositions containing them. The compounds are inhibitors of serine proteases, particularly α-thrombin and may be used in a variety of thrombin related disorders such as venous thrombosis and arterial thrombosis.

BACKGROUND OF THE INVENTION

With a rapidly aging population, diseases of the vascular system are of great concern to our society. Arterial thrombosis is the major cause of death in the form of heart attacks and strokes, while venous thrombosis is associated with pulmonary embolism which occurs after surgery or extended periods of inactivity.

Thrombin is a multifunctional serine protease whose role in thrombosis and hemostasis has been documented by a number of sources (See generally, Tapparelli, et al. *TiPS* 1993, 14, 366–76). Thrombin acts as a procoagulant through proteolytic cleavage of fibrinogen to form fibrin and as an anticoagulant through activation of the protein C pathway. (followed by inactivation of coagulation factors V and VIII.) The concentration of active thrombin is limited by a number of feedback mechanisms involving endogenous factors and proteins. In addition to protein C, antithrombin III is another regulating protein which forms a complex with endogenous heparin. This complex binds to active thrombin, thus inactivating it.

Current anticoagulant therapy consists of three classes of compounds: heparins, coumarins and low molecular weight heparins. These drugs act indirectly to limit the concentration of active thrombin. Heparins and low molecular weight heparins interact with antithrombin III and the coumarins inhibit a number of vitamin K dependent coagulation factors. Although these drugs are prescribed for diseases associated with venous thrombosis and arterial thrombosis, their use is limited. They have a number of side effects, a slow onset of action and only the coumarins are orally active (warfarin and dicumarol).

Indirect thrombin inhibitors have been shown to be less effective at controlling associated diseases than direct thrombin inhibitors. Thus the search for orally active direct thrombin inhibitors is underway in a number of laboratories.

These efforts have produced a number of small peptidyl compounds which directly inhibit thrombin. PPACK, argatroban, (D)-NAPAP and DUP 714 are examples of the direct thrombin inhibitors of interest.

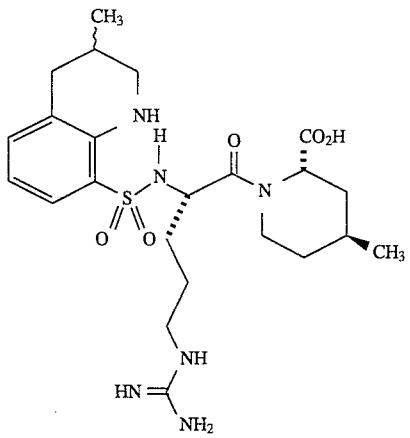
argatroban

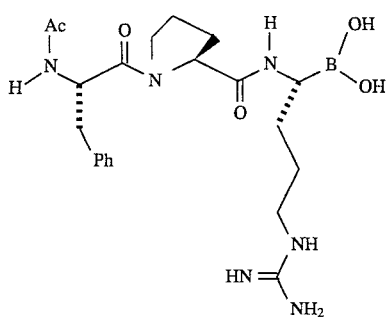
DUP 714

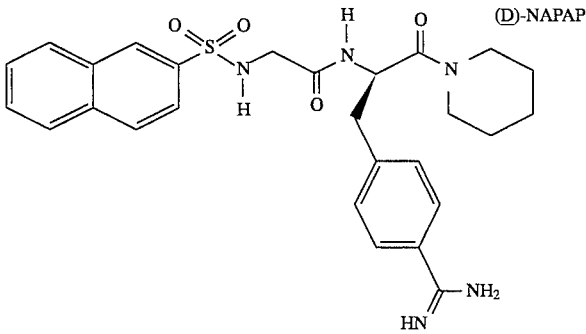
(D)-NAPAP

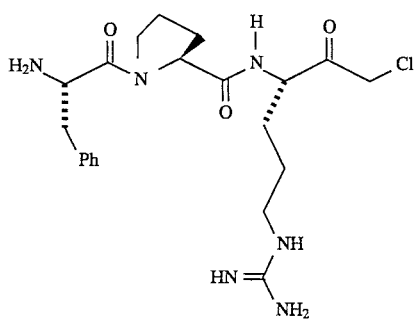
PPACK

Unfortunately, only some of these compounds are weakly orally active and most have a poor selectivity for thrombin versus other serine proteases. Therefore, a need remains for direct thrombin inhibitors which exhibit good selectivity over other serine proteases and are orally active.

SUMMARY OF THE INVENTION

The invention relates to new compounds of the Formula I:

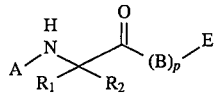

wherein:

A is selected from the group consisting of $C_{1-8}$alkyl, carboxy$C_{1-4}$alkyl, $C_{1-4}$alkoxycarbonyl$C_{1-4}$alkyl, phenyl$C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), formyl, $C_{1-4}$alkoxycarbonyl, $C_{1-12}$alkylcarbonyl, phenyl$C_{1-4}$alkoxycarbonyl, $C_{3-7}$cycloalkylcarbonyl, phenylcarbonyl, substituted phenylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), $C_{1-4}$alkylsulfonyl, $C_{1-4}$alkoxysulfonyl, perfluoro$C_{1-4}$alkylsulfonyl, phenylsulfonyl, substituted phenylsulfonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, $C_{1-4}$alkylsulfinyl, perfluoro$C_{1-4}$alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl, 1-naphthylsulfonyl, 2-naphthylsulfonyl or substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, carboxy or $C_{1-4}$alkoxycarbonyl), 1-naphthylsulfinyl, 2-naphthylsulfinyl or substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

a D or L amino acid which is coupled at its carboxy terminus to the nitrogen depicted in formula I and is selected from the group consisting of alanine, asparagine, 2-azetidinecarboxylic acid, glycine, N-$C_{1-8}$alkylglycine, proline, 1-amino-1-cyclo$C_{3-8}$-alkylcarboxylic acid, thiazolidine-4-carboxylic acid, 5,5-dimethylthiazolidine-4-carboxylic acid, oxazolidine-4-carboxylic acid, pipecolinic acid, valine, methionine, cysteine, serine, threonine, norleucine, leucine, tert-leucine, isoleucine, phenylalanine, 1-naphthalanine, 2-naphthalanine, 2-thienylalanine, 3-thienylalanine, [1,2,3,4]-tetrahydroisoquinoline-1-carboxylic acid and 1,2,3,4]-tetrahydroisoquinoline-2-carboxylic acid where the amino terminus of said amino acid is connected to a member selected from the group consisting of $C_{1-4}$alkyl, tetrazol-5-yl-$C_{1-2}$alkyl, carboxy$C_{1-4}$alkyl, $C_{1-4}$alkoxycarbonyl$C_{1-4}$alkyl, phenyl$C_{1-4}$alkyl, substituted phenyl $C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3-carbonyl, 1-methylamino-1-cyclohexanecarbonyl, 1-hydroxy-1-cyclohexanecarbonyl, 1-hydroxy-1-phenylacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl) 1,1-diphenyl$C_{1-4}$alkylcarbonyl, substituted 1,1-diphenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), perfluoro$C_{1-4}$alkylsulfonyl, $C_{1-4}$alkylsulfonyl, $C_{1-4}$alkoxysulfonyl, phenylsulfonyl, substituted phenylsulfonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, perfluoro$C_{1-4}$alkylsulfinyl, $C_{1-4}$alkylsulfinyl, phenylsulfinyl, substituted phenylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1-naphthylsulfonyl, 2-naphthylsulfonyl, substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl),1-naphthylsulfinyl, 2-naphthylsulfinyl, and substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

or a poly peptide comprised of two amino acids, where the first amino acid is a D or L amino acid, bound via its carboxy terminus to the nitrogen depicted in formula I and is selected from the group consisting of glycine, N-$C_{1-8}$alkylglycine, alanine, 2-azetidinecarboxylic acid, proline, thiazolidine-4-carboxylic acid, 5,5-dimethylthiazolidine-4-carboxylic acid, oxazolidine-4-carboxylic acid, 1-amino-1-cyclo$C_{3-8}$alkylcarboxylic acid, 3-hydroxyproline, 4-hydroxyproline, 3-($C_{1-4}$alkoxy)proline, 4-($C_{1-4}$alkoxy)proline, 3,4-dehydroproline, 2,2-dimethyl-4-thiazolidine carboxylic acid, 2,2-dimethyl-4-oxazolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalanine, [1,2,3,4]-tetrahydroisoquinoline- 1-carboxylic acid, [1,2,3,4]-tetrahydroisoquinoline- 2-carboxylic acid, aspartic acid-4-$C_{1-4}$alkyl ester and glutamic acid-5-$C_{1-4}$alkyl ester and the second D or L amino acid, is bound to the amino terminus of said first amino acid, and is selected from the group consisting of phenylalanine, 4-benzoylphenylalanine, 4-carboxyphenylalanine, 4-(carboxy $C_{0-2}$alkyl)phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 3-benzothienylalanine, 4-biphenylalanine, homophenylalanine, octahydroindole-2-carboxylic acid, 2-pyridylalanine, 3-pyridylalanine, 4-thiazolyalanine, 2-thienylalanine, 3-(3-benzothienyl)alanine, 3-thienylalanine, tryptophan, tyrosine, asparagine, 3-tri-$C_{1-4}$alkylsilylalanine, cyclohexylglycine, diphenylglycine, phenylglycine, methionine sulfoxide, methionine sulfone, 2,2-dicyclohexylalanine, 2-(1-naphthylalanine), 2-(2-naphthylalanine), phenyl substituted phenylalanine (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), aspartic acid, aspartic acid-4-$C_{1-4}$alkyl ester, glutamic acid, glutamic acid-5-$C_{1-4}$ alkyl ester, cyclo$C_{3-8}$alkylalanine, substituted cyclo$C_{3-8}$alkylalanine (where the ring substituents are carboxy, $C_{1-4}$alkylcarboxy, $C_{1-4}$alkoxycarbonyl or aminocarbonyl), 2,2-diphenylalanine and all alpha-$C_{1-5}$alkyl of all amino acid derivatives thereof, where the amino terminus of said second amino acid is unsubstituted or monosubstituted with a member of the group consisting of formyl, $C_{1-12}$alkyl, tetrazol-5-yl$C_{1-2}$alkyl, carboxy$C_{1-8}$alkyl, carboalkoxy$C_{1-4}$alkyl, phenyl $C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, $C_{1-6}$alkoxycarbonyl, phenyl$C_{1-6}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkylcarbonyl, $C_{1-4}$alkylsulfonyl, $C_{1-4}$alkoxysulfonyl, perfluoro$C_{1-4}$alkylsulfonyl, phenylsulfonyl, substituted phenylsufonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, $C_{1-4}$alkylsulfinyl, perfluoro $C_{1-4}$alkylsulfinyl, phenylsulfinyl, substituted phenylsufinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl 1-naphthylsulfonyl, 2-naphthylsulfonyl, substituted naphthylsulfonyl (where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1-naphthylsulfinyl, 2-naphthylsulfinyl and substituted naphthylsulfinyl (where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

$R_1$ is selected from the group consisting of hydrogen and $C_{1-5}$alkyl;

$R_2$ is selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy $C_{2-5}$alkyl, phenyl, substituted phenyl (where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro), benzyl, phenyl substituted benzyl (where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro), hydroxy$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alkyl and $C_{1-5}$alkyl;

p is 0 or 1;

B is

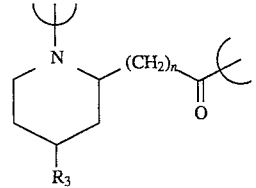

where n is 0–3, R3 is H or $C_{1-5}$alkyl and the carbonyl moiety of B is bound to E;

E is a heterocycle selected from the group consisting of oxazolin-2-yl, oxazol-2-yl, thiazol-2-yl, thiazol-5-yl, thiazol-4-yl, thiazolin-2-yl, imidazol-2-yl, 4-oxo-2-quinoxalin-2-yl, 2-pyridyl, 3-pyridyl, benzo[b]thiophen-2-yl, benzoxazol-2-yl, benzimidazol-2-yl, benzothiazol-2-yl, triazol-4-yl, triazol-6-yl, tetrazol-2-yl, pyrimidin-2-yl, quinolin-2-yl, indol-2-yl, pyrazol-2-yl, 4,5,6,7-tetrahydrobenzothiazol-2-yl, naphtho[2,1-d]thiazol-2-yl, naphtho[1,2-d]thiazol-2-yl quinoxalin- 2-yl, isoquinolin-1-yl, isoquinolin-3-yl, benzo[b]furan-2-yl, pyrazin-2-yl, quinazolin-2-yl, isothiazol-5-yl, isothiazol-3-yl, purin-8-yl and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl, hydroxy or phenyl$C_{1-4}$alkylaminocarbonyl;

or pharmaceutically acceptable salts thereof.

The terms used in describing the invention are commonly used and known to those skilled in the art. However, the terms that could have other meanings are defined. "Independently" means that when there are more than one substituent, the substitutents may be different. The term "alkyl" refers to straight, cyclic and branched-chain alkyl groups and "alkoxy" refers O-alkyl where alkyl is as defined supra. "CBZ" refers to benzyloxycarbonyl. "BOC" refers to t-butoxycarbonyl and "Ts" refers to toluenesulfonyl. "DCC" refers to 1,3-dicyclohexylcarbodiimide, "DMAP" refers to 4-N'N-dimethylaminopyridine and "HOBT" refers to 1-hydroxybenzotriazole hydrate. "Dansyl" refers to 5-dimethylamino-1-naphthalenesulfonamide and "FMoc" refers to N-(9-fluorenylmethoxycarbonyl).

DETAILED DESCRIPTION OF THE INVENTION

The compounds of the invention may be prepared as illustrated in Scheme I. The illustrated example prepares a compound where A is a polypeptide where the first amino acid is L-proline and the second amino acid is N-methyl-D-phenylalanine, $R_1$ is hydrogen, $R_2$ is amidino $C_4$ alkyl, p is 0 and E is benzoxazol-2-yl. Other compounds which may be prepared from this general scheme are listed below with the appropriate modifications.

A natural or unnatural amino acid is the starting point for the scheme. Compound Ia is prepared by known synthetic procedures to give the protected amino acid, where the α-amino group is protected with CBZ and the ω-amino is protected with a Ts. Culvenor, et al. *J. Chem. Soc. D.* 1969 19,, 1091. The protecting groups can be varied. In Scheme I the α-amino and ω-amino protecting groups must be stable to moderately acidic conditions and removed by methods that are mutually exclusive. Examples of appropriate α-amino and ω-amino protecting groups are listed respectively: FMOC-TS, FMOC-NO$_2$ and CBZ-NO$_2$. For examples of other suitable protecting groups see Green, Theodora, *Protecting Groups in Organic Synthesis;* John Wiley & Sons, New York, 1981.

SCHEME I

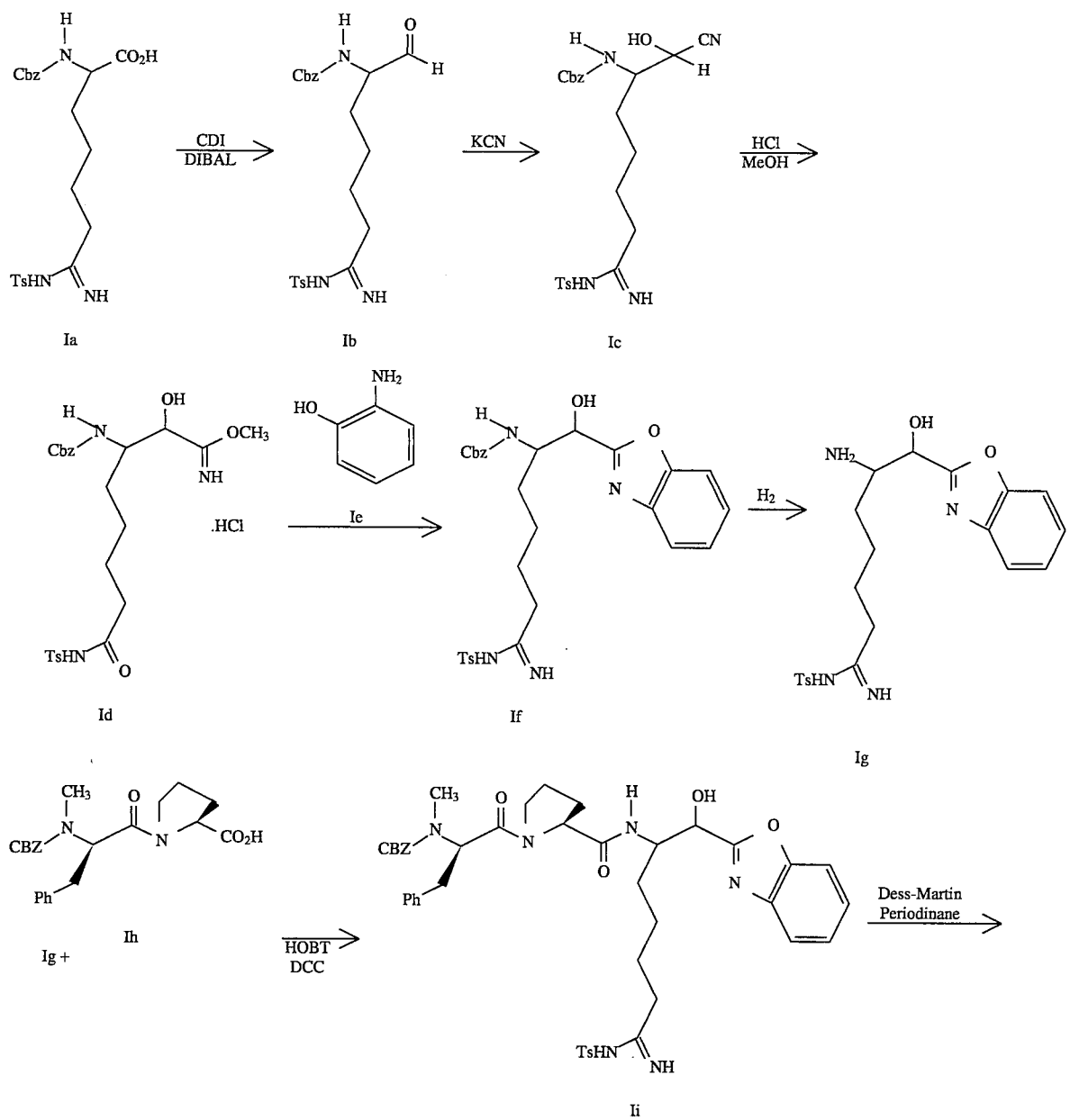

-continued
SCHEME I

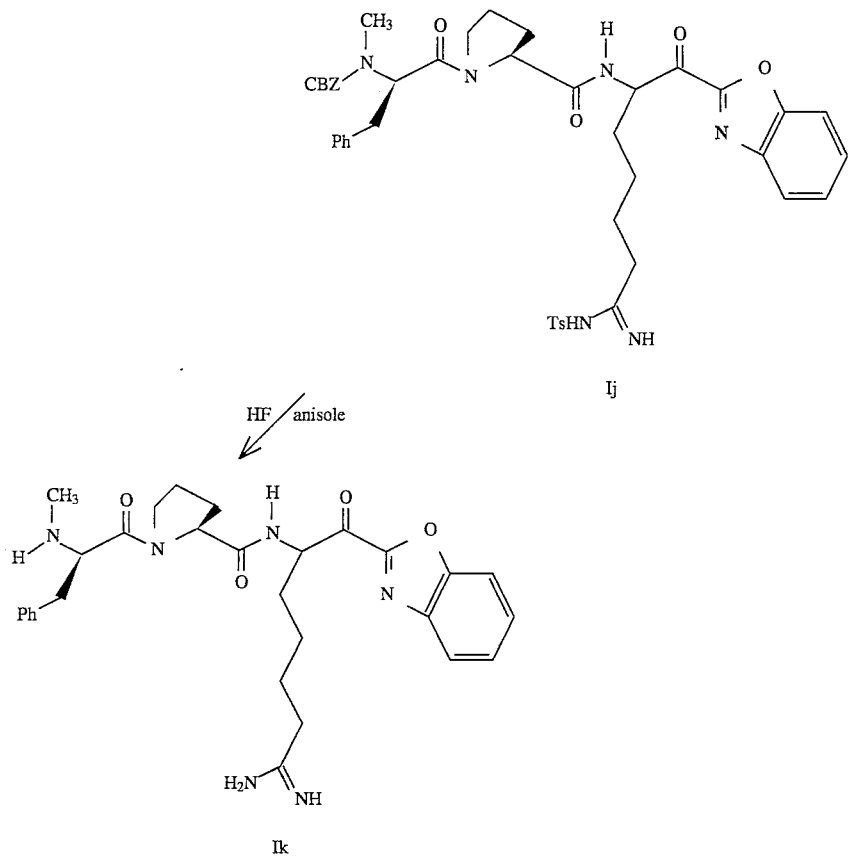

Compound Ia is coupled to 1,1'-carbonyldiimidazole in THF at 0°–10° C., followed by treatment with DIBAL/hexane at −42° C. to give aldehyde Ib using the method described by Greco, et al, *Journal Of The American Chemical Society*, 1995, 117, 1225. A direct conversion of Ia to Ib may be accomplished using bis(N-methylpiperazinyl)aluminum hydride in toluene at 0° C. to reflux. (Hubert, et al. *Journal Of Organic Chemistry* 1984, 49, 2279). Another method for the direct conversion of Ia to Ib uses borane-dimethylsulfide in THF at 25° C. to reflux. Brown, et al, *Synthesis* 1979, 704. Yet another method is to convert the carboxylic acid to the corresponding Weinreb Amide using triethylamine, BOP and N,O-dimethylhydroxylamine hydrochloride. Reduction of formed amide with LAH in THF gives the corresponding aldehyde.

Cyanohydrin Ic is prepared by the addition of KCN to an emulsion of the aldehyde Ib in $H_2O$, MeOH and ethyl acetate at room temperature. Alternatively compound Ic can prepared combining aldehyde Ib, acetone cyanohydrin and triethylamine in dichloromethane at room temperature. Imidate Id, is prepared by treating Ic with gaseous HCl in methanol. Benzoxazole If is prepared by heating Id with Ie in ethanol at reflux.

Amine Ig is prepared by hydrogenolysis of If using $Pd(OH)_2/C$ as a catalyst at room temperature under atmospheric or elevated pressure using a hydrogen donor solvent. Other catalysts such as Pd/C or Pd black can be employed using suitable reaction conditions. Other reagents that may be used to remove the CBZ group include: hydrazine, iodotrimethylsilane methanesulfonic acid/anisole and boron tribromide.

Compound Ig may be coupled with acid Ih HOBT and DCC in $CH_3CN$ at room temperature to give the coupled alcohol Ii. Other suitable coupling reagents include: BOP, BOP-Cl and PyBrOP.

Compound Ii is oxidized to compound Ij using periodinane in an anhydrous aprotic solvent. The final step of the Scheme I is deprotection of Ij using HF in the presence of a carbocation scavenger such as anisole, thioanisole, pentamethylbenzene, dimethylsulfide and cresol followed by reverse phase choromatography to give the final product Ik.

To produce the compounds of the invention where A is $C_{1-4}$alkyl, phenyl$C_{1-4}$alkyl and substituted phenyl$C_{1-4}$alkyl, the starting material of Scheme I is modified. Treatment of compound Ia with two equivalents of sodium hydride in DMF from 0° C. to room temperature followed by an alkyl halide gives the N-alkylated carboxylic acid. This acid can be treated under the same reaction conditions used in Scheme I to give the desired compounds as illustrated in Scheme IA.

SCHEME IA

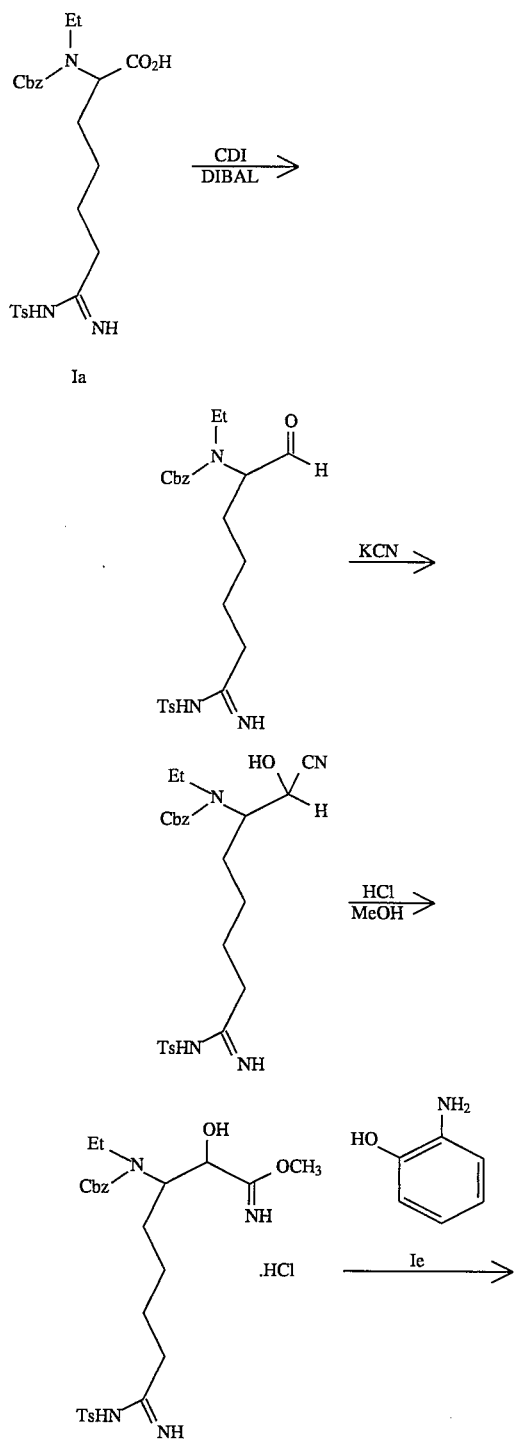

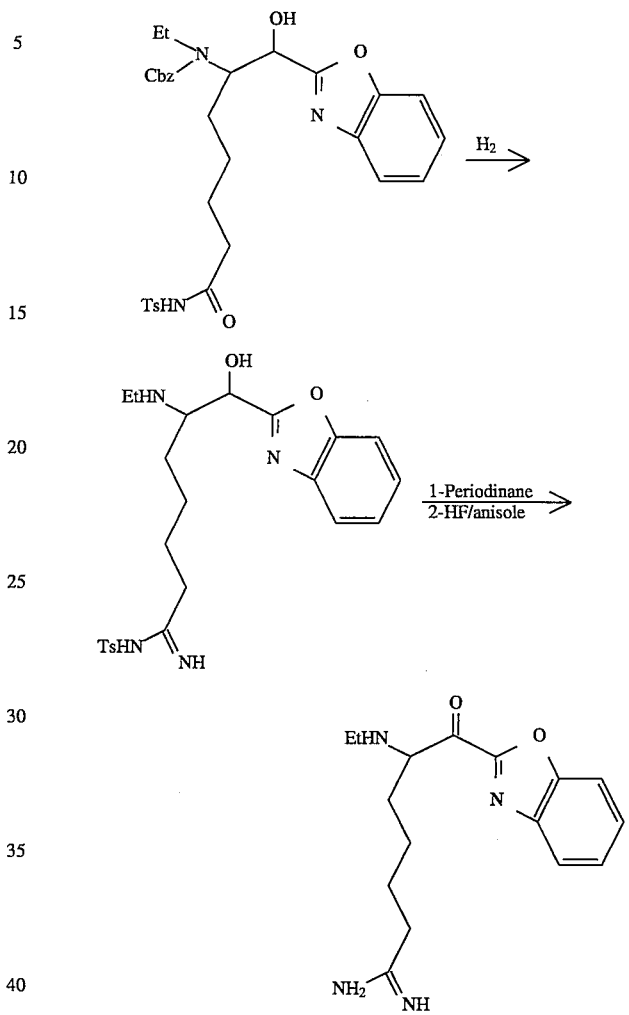

If A is $C_{1-4}$alkoxycarbonyl, phenyl$C_{1-4}$alkoxycarbonyl, $C_{1-4}$alkylcarbonyl, $C_{3-7}$cycloalkylcarbonyl, phenylcarbonyl, and substituted phenylcarbonyl, Scheme I may be modified once again. The CBZ group of Ia is removed and the resulting free amine is reacted with an appropriate carbonyl compound. Examples of such compounds are benzoyl chloride, propionyl chloride, methyl chloroformate, cyclohexane carbonyl chloride, benzyl chloroformate and the like. This starting material is used in Scheme IB, under the same conditions used in Scheme IA to give the desired compounds.

SCHEME IB

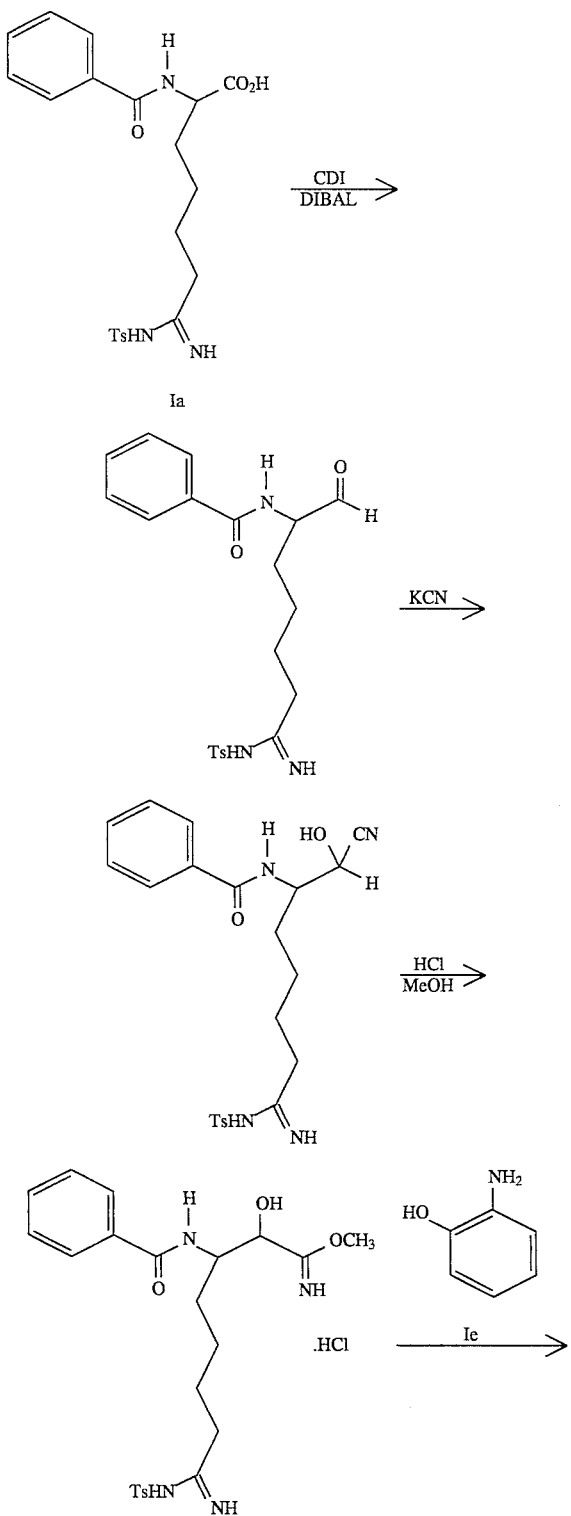

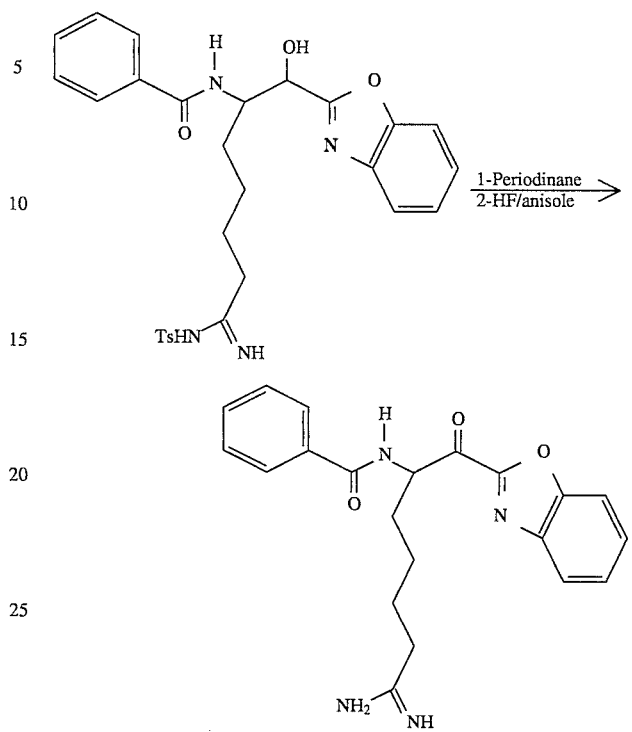

Similarly, when A is: $C_{1-4}$alkylsulfonyl, perfluoro $C_{1-4}$alkylsulfonyl, phenylsulfonyl, substituted phenylsulfonyl, $C_{1-4}$alkylsulfinyl, perfluoro $C_{1-4}$alkylsulfinyl, phenylsulfinyl, substituted phenylsulfinyl, 1-napthylsulfonyl, 2-napthylsulfonyl and substituted napthylsulfonyl, 1-napthylsulfinyl, 2-napthylsulfinyl or substituted napthylsulfinyl; the desired compounds may be prepared from their corresponding commercially available arylsulfonyl and aryl sulfinyl halides using Scheme IB.

If A is an amino acid, whose amino terminus is connected to another group, Scheme I may be used again. The N-coupled amino acid (protected if necessary) replaces Ih in Scheme I using the same reaction conditions. Alanine, asparagine, 2-azetidinecarboxylic acid, glycine, proline, pipecolinic acid, valine, methionine, cysteine, serine, threonine, leucine, tert-leucine, and isoleucine may be used in this scheme where their amino groups are connected to $C_{1-4}$alkyl, (phenyl$C_{1-4}$alkyl), (substituted phenyl $C_{1-4}$alkyl), (1,1-diphenyl$C_{1-4}$alkyl, 3-phenyl-2-hydroxypropionyl), (2,2-diphenyl-1-hydroxyethylcarbonyl), ([1,2,3,4]-tetrahydroisoquinoline-1-carbonyl), ([1,2,3,4]-tetrahydroisoquinoline-3-carbonyl), (1-methylamino-1-cyclohexanecarbonyl), (1-hydroxy-1-cyclohexanecarbonyl), (1-hydroxy-1-phenylacetyl), 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-4}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl, 1,1-diphenyl$C_{1-4}$ alkylcarbonyl, substituted 1,1-diphenyl$C_{1-4}$ alkylcarbonyl, perfluoro$C_{1-4}$ alkylsulfonyl, $C_{1-4}$ alkylsulfonyl, phenylsulfonyl, substituted phenylsulfonyl, perfluoroC$_{1-4}$alkylsulfinyl, C$_{1-4}$alkylsulfinyl, phenylsulfinyl, substituted phenylsulfinyl, 1-napthylsulfonyl, 2-napthylsulfonyl, substituted napthylsulfonyl, 1-napthylsulfinyl, 2-napthylsulfinyl, and substituted napthylsulfinyl.

If A is a dipeptide whose amino terminus is connected to another group, once again Scheme I may be used. One example is the replacement of Ih with N-methyl-N-CBZ-D-phenylalanyl-L-azetidinecarboxylic acid to give the corresponding final product using substantially the same reaction conditions as Scheme I.

To prepare compounds where R$_1$ is H and R$_2$ is aminoC$_{2-5}$alkyl, guanidinoC$_{2-5}$alkyl, amidinoC$_{2-5}$alkyl, C$_{1-3}$alkoxyC$_{2-5}$ alkyl, phenyl, substituted phenyl (where the substituents are selected from amidino, guanidino, C$_{1-4}$alkylamino, halogen, perfluoro C$_{1-4}$ alkyl, C$_{1-4}$alkyl, C$_{1-3}$alkoxy and nitro), benzyl, aryl substituted benzyl (where the substituents are selected from amidino, guanidino, C$_{1-4}$alkylamino, halogen, perfluoro C$_{1-4}$alkyl, C$_{1-4}$alkyl, C$_{1-3}$ alkoxy and nitro), (pyridin-4-yl)amino C$_{1-4}$alkyl, (pyridin-3-yl)amino C$_{1-4}$alkyl, C$_{1-5}$alkylamino C$_{2-5}$alkyl, and C$_{1-5}$alkyl; Scheme I may be used once again. Starting material Ia may be replaced with commercially available amino acids, such as: arginine, leucine, phenylalanine, lysine, p-amidinophenyl alanine, methoxypropyl glycine and 2-(3-pyridyl)alanine; where the α amino group, as well as any other reactive substituents are protected with CBZ, Ts or FMOC as appropriate. If the desired substituents are not commercially available, as is the case when R$_2$ is substituted phenyl and substituted benzyl, the desired amino acid may be synthesized by published chemical procedures. See D. A. Evans et al (*Tetrahedron* 1988, 44, 5525–5540).

To prepare compounds where E is 4-oxo-2-quinoxalin-2-yl, benzimidazol-2-yl and benzothiazol-2-yl, Scheme I may be used again. Replacement of Ie with 2-aminothiophenol gives the benzothiazole derivatives following the same reaction conditions as Scheme I; with the caveat one must not use Pd to remove the CBZ group. However any of the other methods listed earlier may be used.

If E is 5-carboethoxythiazol-2-yl, Scheme I may be modified to give the desired compounds, as illustrated in Scheme Ic. Replacement of compound Ie with cysteine ethyl ester hydrochloride gives the thiazoline derivative Il at room temperature using CH$_2$Cl$_2$ as a solvent. Oxidation of the thaizoline ring of compound Il with MnO$_2$ at room temperature gives thiazole Im. Oxidation of the hydroxyl group of Im, followed by removal of the amino protecting groups with HF/anisole gives the carboethoxy derivative In.

To prepare ester derivatives of In, the carboethoxy group in either Il, In or Im may be modified using known chemistry. One can prepare the following ester derivatives in this manner: carboxy, phenylC$_{1-4}$alkylaminocarbonyl, amido, formyl and other alkoxyC$_{1-4}$carbonyl groups.

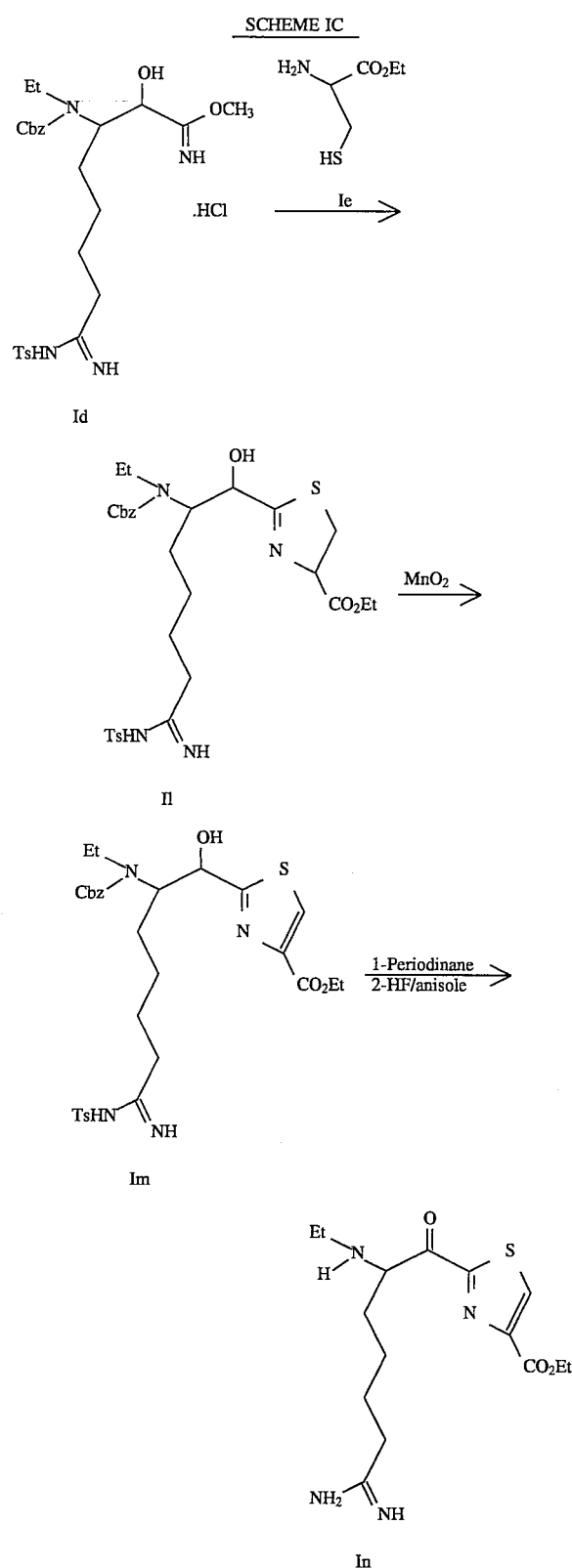

Another method of preparing the compounds of the invention is illustrated in Scheme II. The illustrated example prepares a compound where A is L-proline which is connected at its N-terminus to (1,1-diphenyl C$_2$ alkylcarbonyl), R$_1$ is hydrogen, R$_2$ is guanidino C$_3$ alkyl, p is 0 and E is thiazol-2-yl. Other compounds which may be prepared from this general scheme are listed below with the appropriate modifications.

SCHEME II

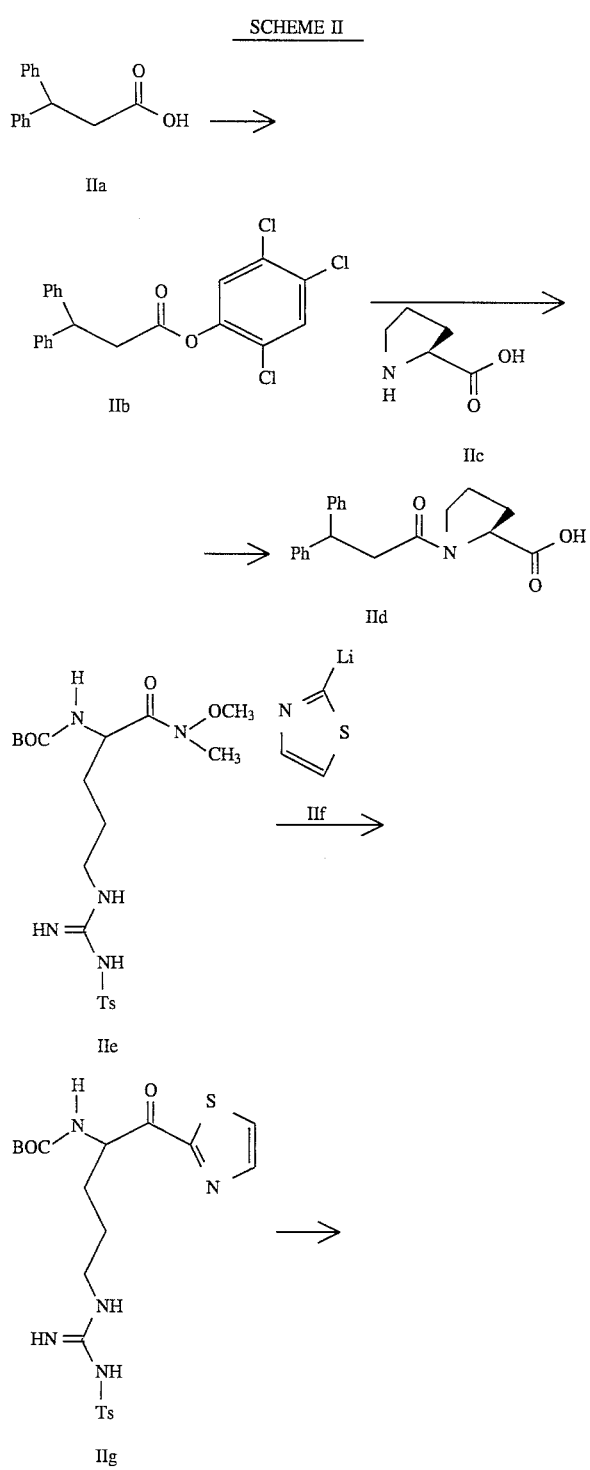

-continued
SCHEME II

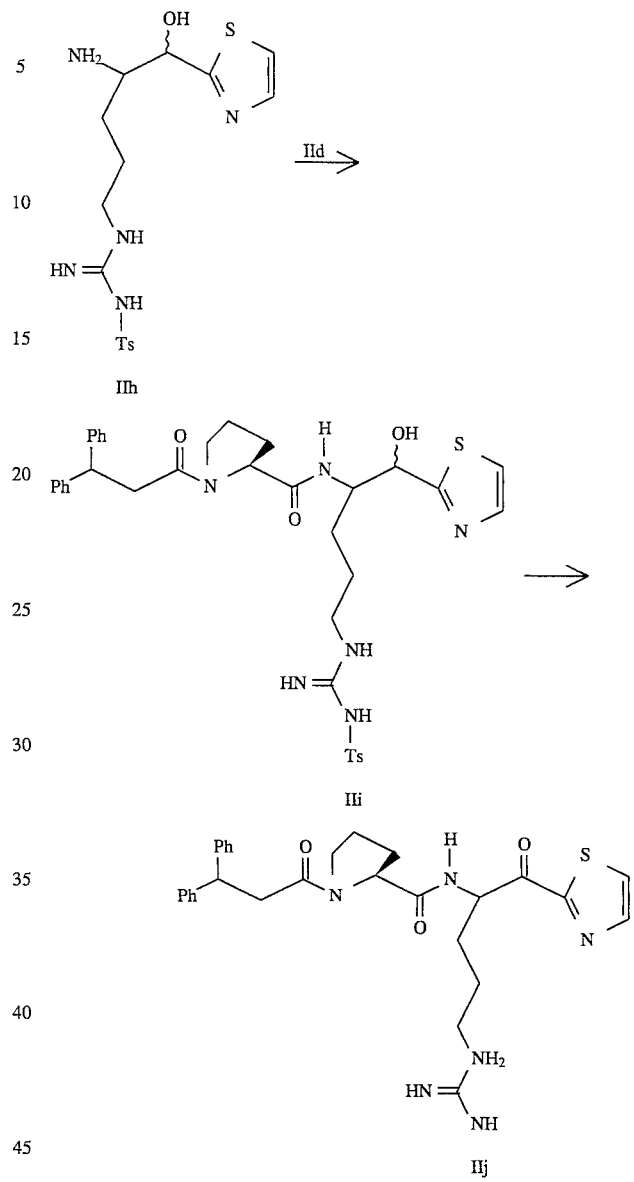

A commercially available acid IIa is the starting point for this scheme. Said acid is converted into the activated ester derivative IIb by treatment with DCC and 2,4,5-trichlorophenol at −20°–0° C. in an inert solvent such as THF. The proline derivative IId was prepared by treating IIb with IIc, triethyl amine and pyrindine. Alternatively IId could have been prepared directly by treating acid IIa with amino acid IIc in the presence any of the peptide coupling agents listed in Scheme I.

The Weinrab amide of $N^{\alpha}$Boc-$N^{\omega}$-tosylarginine, IIe, was prepared by literature procedures from the protected acid. DiMaio, et al. *Journal of Medicinal Chemistry* 1992, 35, 3331. This amide was treated with IIf at –78° C. in THF to give ketone IIg. This ketone may be reduced with a hydride reducing agent such as sodium borohydride, at –20° to room temperature followed by treatment with TFA at room temperature to give the corresponding amine IIh.

Coupling IIh and IId in the presence of DCC and HOBT at room temperature in acetonitrile gives the coupled alcohol IIi. Other peptide coupling reagents which can be used for this reaction include: benzotriazol-1 -yloxy-tris(dimethylamino)phosphonium hexafluorophosphate, bis (2-oxo-3-oxazolidinyl)phosphinic chloride, 2-dimethylaminoisopropyl chloride hydrochloride and bromo-tris-pyrrolidinophosphonium hexafluorophosphate. Oxidation of IIi to the ketone using periodinane in $CH_2Cl_2$, followed by removal of the ω-amino protecting group with HF and anisole gives the desired product IIj.

To prepared compounds of the invention where A is $C_{1-4}$alkyl, phenyl$C_{1-4}$alkyl, or substituted phenyl$C_{1-4}$alkyl, the starting material of Scheme II can modified and used as illustrated in Scheme IIA.

SCHEME IIA

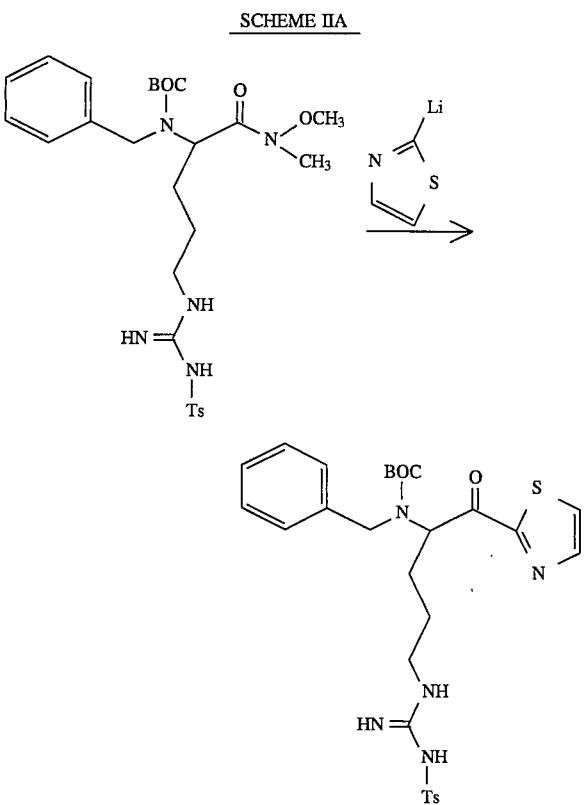

-continued
SCHEME IIA

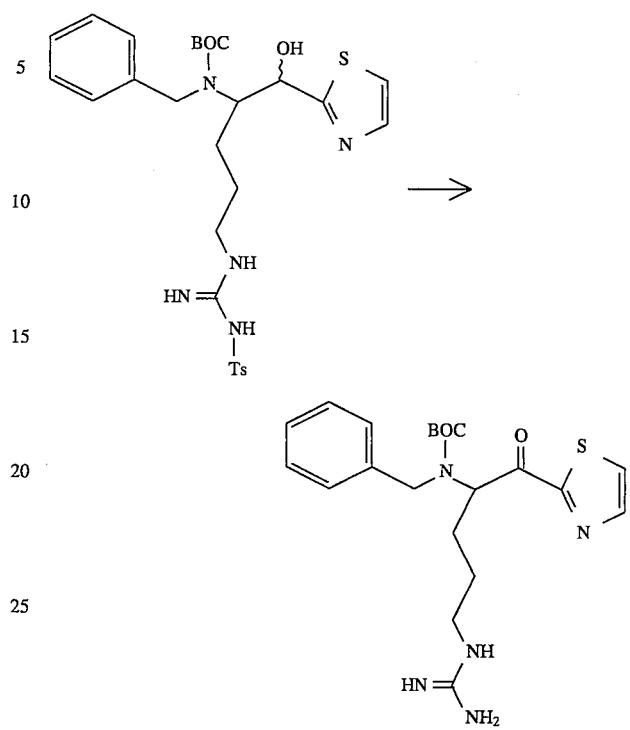

The starting material for Scheme IIA is made from the protected Weinrab amide, IIe. The amide is deprotected with TFA, reductively alkylated with an appropriate substrate and sodium cyanoborohydride and protection with BOC to the N-alkylated starting material. The illustrated example uses benzaldehyde as a substrate for the reductive alkylation. The alkylated material can be treated with the same conditions and reagents as Scheme II to give the desired compounds.

If A is formyl, $C_{1-4}$alkoxycarbonyl, phenyl$C_{1-4}$ alkoxycarbonyl, $C_{1-4}$alkylcarbonyl, $C_{3-7}$cycloalkylcarbonyl, phenylcarbonyl, and substituted phenylcarbonyl, Scheme II may be modified once again. The BOC group of IIe is removed with TFA at room temperature and the resulting free amine is reacted with an appropriate commercially available carbonyl compound. Examples of such compounds are formic acid/acetic anhydride, benzoyl chloride, propionyl chloride, methyl chloroformate, cyclohexane carbonyl chloride and the like. This starting material is used under the same conditions used in Scheme IIA to give the desired compounds.

Similarly, when A is: $C_{1-4}$alkylsulfonyl, perfluoro $C_1$-alkylsulfonyl, phenylsulfonyl, substituted phenylsulfonyl, $C_{1-4}$alkylsulfinyl, perfluoro $C_{1-4}$alkylsulfinyl, phenylsulfinyl, substituted phenylsulfinyl, 1-napthylsulfonyl, 2-napthylsulfonyl and substituted napthylsulfonyl, 1-napthylsulfinyl, 2-napthylsulfinyl and substituted napthylsulfinyl; the desired compounds may be prepared from their corresponding commercially available arylsulfonyl and aryl sulfinyl halides using Scheme IIA.

If A is an amino acid, whose amino terminus is connected to another group, Scheme II may be used again. The N-coupled amino acid may be purchased or prepared by known procedures. This amino acid will replace IId in Scheme II using the same reaction conditions. Alanine, asparagine, 2-azetidinecarboxylic acid, glycine, proline, pipecolinic acid, valine, methionine, cysteine, serine, threonine, leucine, tert-leucine, and isoleucine may be used in this scheme where their amino groups are connected to $C_{1-4}$alkyl, phenyl$C_{1-4}$alkyl, substituted phenyl $C_{1-4}$alkyl, 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3-carbonyl, 1-methylamino-1-cyclohexanecarbonyl, 1-hydroxy-1-cyclohexanecarbonyl, 1-hydroxy-1-phenylacetyl, 1-cyclohexyl- 1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$ alkoxycarbonyl, $C_{1-4}$alkylcarbonyl, perfluoro $C_{1-4}$alkyl $C_{0-4}$ alkylcarbonyl, phenyl $C_{1-4}$ alkylcarbonyl, substituted phenyl $C_{1-4}$alkylcarbonyl, 1,1-diphenyl $C_{1-4}$alkylcarbonyl, substituted 1,1-diphenyl $C_{1-4}$alkylcarbonyl, perfluoro$C_{1-4}$ alkylsulfonyl, $C_{1-4}$alkylsulfonyl, phenylsulfonyl, substituted phenylsulfonyl, perfluoro$C_{1-4}$alkylsulfinyl, $C_{1-4}$alkylsulfinyl, phenylsulfinyl, substituted phenylsulfinyl, 1-napthylsulfonyl, 2-napthylsulfonyl, and substituted napthylsulfonyl, 1-napthylsulfinyl, 2-napthylsulfinyl, and substituted napthylsulfinyl.

If A is a dipeptide whose amino terminus is connected to another group, once again Scheme II may be used. One example is the replacement of IId with N-methyl-phenylalane-pipecolinic acid to give the corresponding final product using substantially the same reaction conditions as Scheme II.

To prepare compounds where $R_1$ is H and $R_2$ is amino $C_{2-5}$ alkyl, guanidino $C_{2-5}$alkyl, amidino $C_{2-5}$alkyl, $C_1$-alkoxy $C_{2-5}$alkyl, phenyl, substituted phenyl (where the substituents are selected from amidino, guanidino, $C_{1-4}$ alkylamino, halogen, perfluoro $C_{1-4}$ alkyl, $C_{1-4}$alkyl, $C_{1-3}$alkoxy and nitro), benzyl, aryl substituted benzyl (where the substituents are selected from amidino, guanidino, $C_{1-4}$alkylamino, halogen, perfluoro $C_{1-4}$alkyl, $C_{1-4}$alkyl, $C_{1-3}$ alkoxy and nitro), (pyridin-4-yl)amino $C_{1-4}$alkyl, (pyridin-3-yl)amino $C_{1-4}$alkyl, $C_{1-5}$ alkylamino $C_{2-5}$alkyl, and $C_{1-5}$ alkyl; Scheme II may be used once again. Using the methods of DiMaio, et al. *Journal of Medicinal Chemistry* 1992, 35, 3331, the Weinreb amides of known protected amino acid may prepared. These compounds replace compound IIe, in Scheme II and are treated under the same reaction conditions illustrated in Scheme II.

Scheme II may be used once again to prepare compounds of the invention where E is oxazol-2-yl; thiazol-2-yl; thiazol-5-yl; thiazol-4-yl; 1-alkylimidazol-2-yl; 2-pyridyl; 3-pyridyl; 4-pyridyl; benzo[b]thiophen-2-yl; benzoxazol-2-yl; 1-alkylbenzimidazol-1-yl; benzothiazol-2-yl; 1-alkylindol-2-yl; 4,5,6,7-tetrahydrobenzothiazol-2-yl; naphtho[2, 1 -d]thiazol-2-yl; naphtho[1,2-d]thiazol-2-yl; pyrimidin-2-yl; quinoxalin-2-yl; benzo[b]furan- 2-yl; pyrazin-2-yl, quinazolin-2-yl, isothiazol-5-yl, isothiazol-3-yl. When the nitrogen at position 1 is protected with a base-stable protecting group (eg. TMS, Boc, Ts, etc), Scheme II may be used to prepare compounds of the invention where E is imidazol-2-yl; pyrazol-2-yl; triazol-2-yl; triazol-4-yl; triazol-6-yl; tetrazol-2-yl; quinolin-2-yl; indol-2-yl; isoquinolin-1-yl; isoquinolin-3-yl; and purin-8-yl (requires protection at position 7 instead of 1). Replacement of IIf with any of the known lithiated heterocycles listed gives the desired compounds.

Another method of preparing the compounds of the invention is illustrated in Scheme III. The illustrated example prepares a compound where A is a polypeptide Where the first amino acid is L-proline and the second amino acid is N-methyl-D-phenylalanine, $R_1$ is hydrogen, $R_2$ is (guanidino $C_3$ alkyl), p is 1, n is 0, $R_3$ is H and E is thiazol-2-yl.

SCHEME III

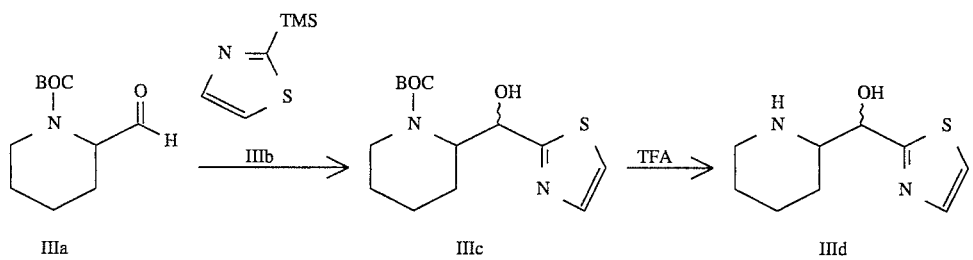

-continued
SCHEME III

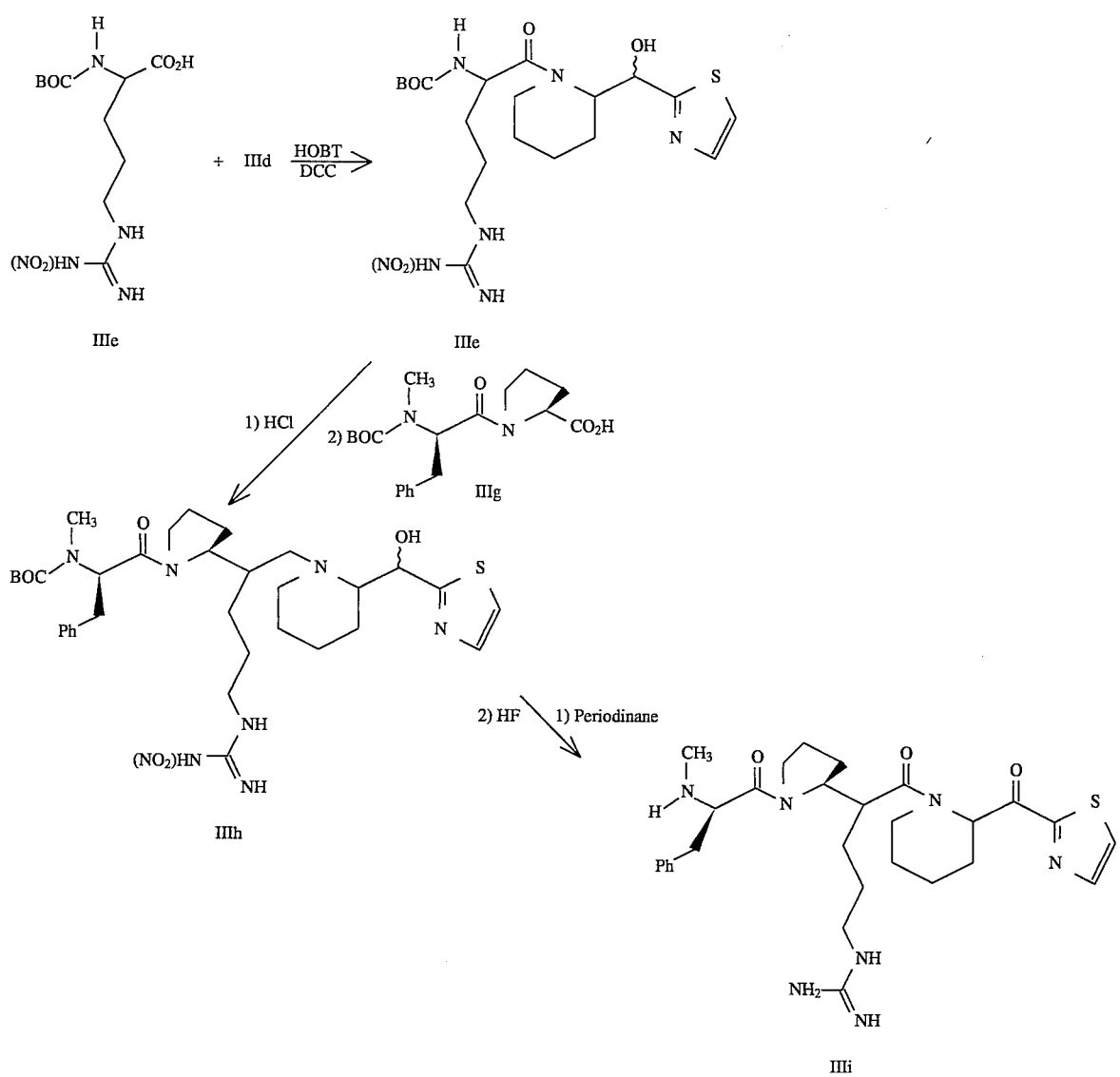

Compounds of the invention where E is equal to pyrazo3-yl is can be prepared via the 1,3-dipolar addition of diazoketones to alkynes (Padwa et al, "1,3-Dipolar Cycloaddition Chemistry," 2 vols., Wiley, New York, 1984), which is exemplified in Scheme IV. Diazoketone intermediate IVa (U.S. Pat. No. 4,318,904) can be reacted with alkyne IVb in refluxing benzene to give pyrazole IVc, which can be elaborated further to pyrazole IVd as previously described.

SCHEME IV

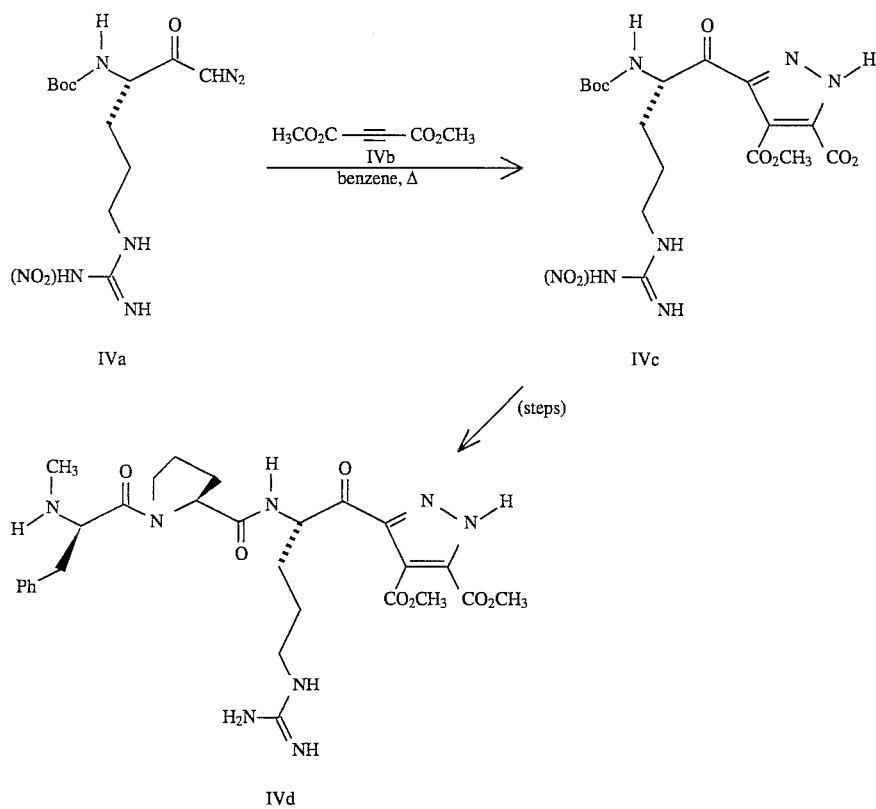

Compounds of the invention where E is equal to thiazol-2-yl and oxazole-2-yl can also be prepared as shown in Scheme V. Cyclization of alcohols Va and Vb with the Burgess reagent to the corresponding thiazoline and oxazoline followed by oxidation with $MnO_2$ or $NiO_2$ will furnish Vc and Vd (P. Wipf et al *Tetrahedron Letters,* 1992, 33, 6267–6270). Similarly, aldehyde Ve can be converted to Vd with triphenylphoshine/iodine in the presence of triethylamine (P. Wipf et al *Journal of Organic Chemistry* 1993, 58, 3604–3603).

SCHEME V

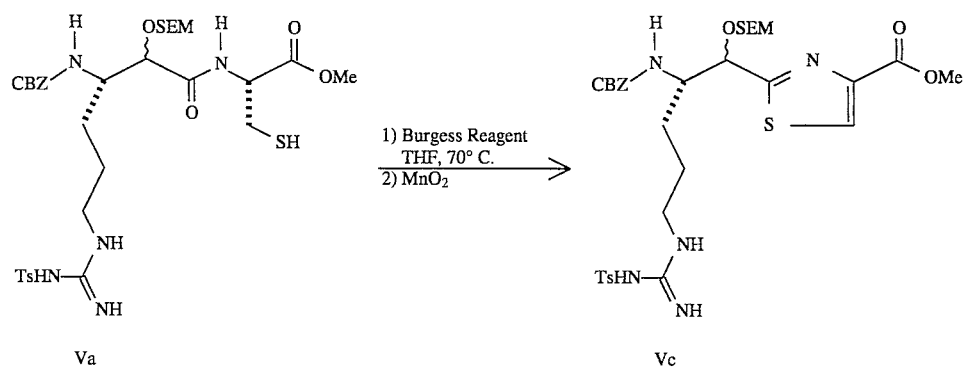

-continued
SCHEME V
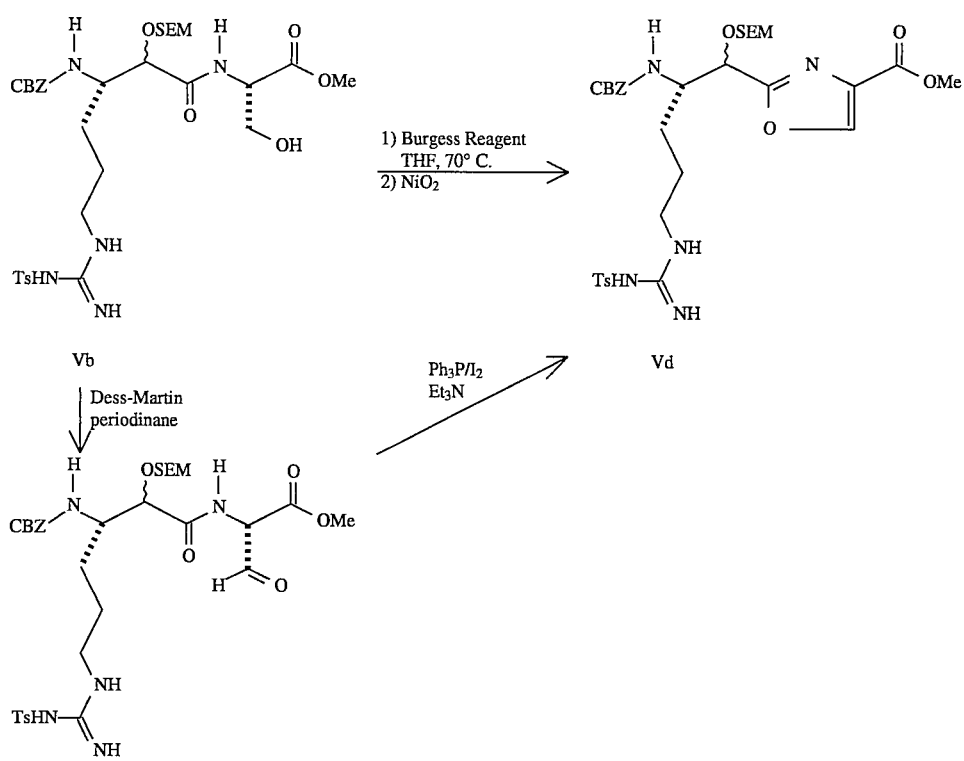
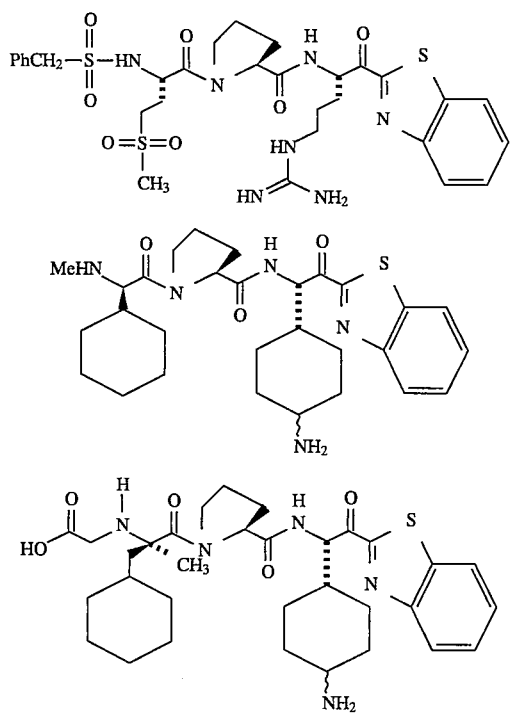
Although the claimed compounds are useful as thrombin or trypsin inhibitors, the preferred compounds of Formula I include:
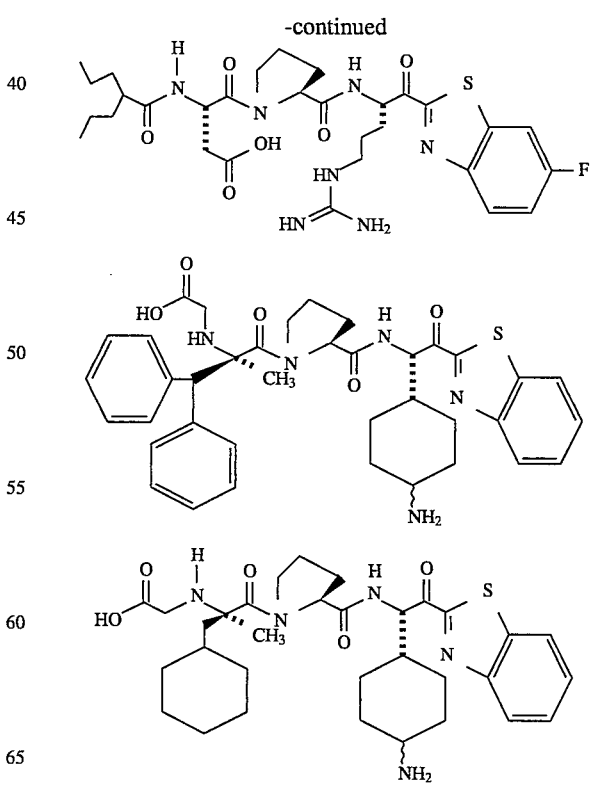

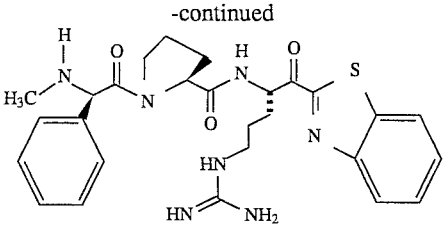

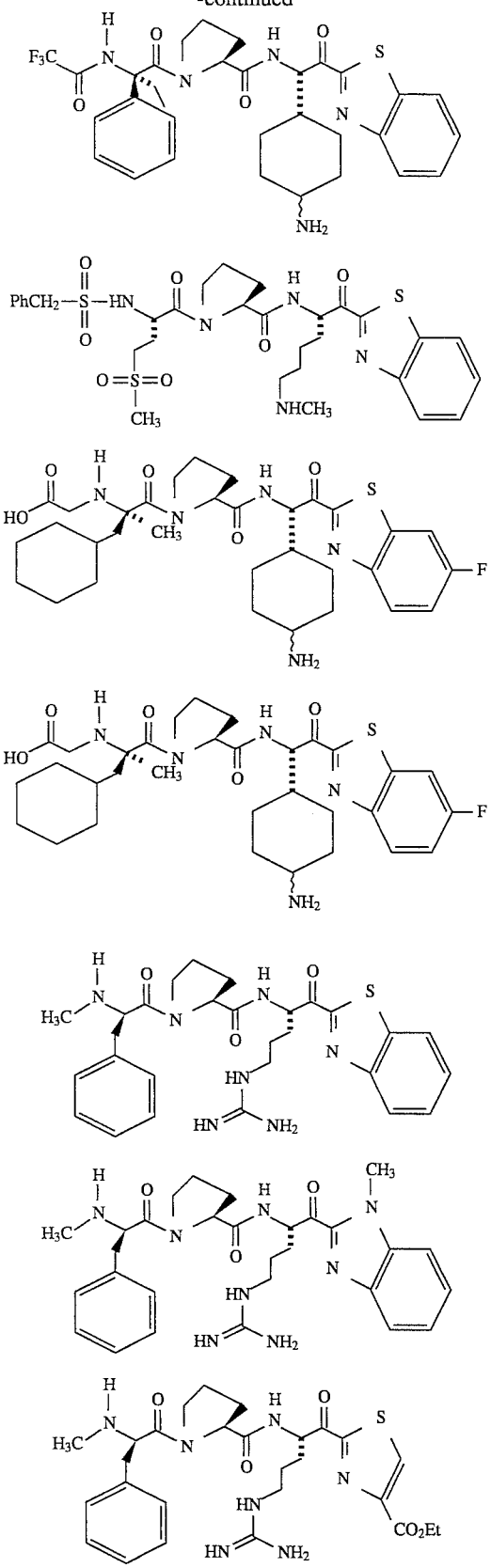

The particularly preferred "A"s are:
1 naphthylsulfonyl, 2-naphthylsulfonyl, substituted naphthylsulfonyls (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy and $C_{1-4}$alkoxycarbonyl);

an L amino acid such as glycine or proline, where the amino terminus is unsubstituted or monosubstituted with a member of the group consisting of 1 naphthylsulfonyl, 2-naphthylsulfonyl and substituted naphthylsulfonyls (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy and $C_{1-4}$alkoxycarbonyl), formyl, and phenylcarbonyl; or a poly peptide comprised of two amino acids, where the first acid is L- proline or L-pipecolinic and the second acid is D-phenylalanine, D-cyclohexylalanine, D-diphenylalanine or (2,3,4,5,6-pentafluorophenyl)alanine where the amino terminus of said second amino acid is unsubstituted or monosubstituted with a member of the group consisting of $C_{1-5}$alkyl perfluoro$C_{1-4}$alkyl or formyl.

The particularly preferred "$R_1$"s are hydrogen and methyl. The particularly preferred "$R_2$"s are selected from the group consisting of amino$C_{2-5}$alkyl, guanidino$C_{2-5}$alkyl, amidino$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alky, 3-aminocyclohexyl$C_{0-2}$alky and $C_{1-5}$alky.

The particularly preferred "E"s are heterocycles selected from the group consisting of thiazol-2-yl, thiazol-5-yl, thiazol-4-yl, thiazolin-2-yl, benzoxazol-2-yl, benzimidazol-2-yl, imidazol-2-yl, 4-oxo-2-quinoxalin-2-yl, benzothiazol-2-yl, triazol-4-yl, triazol-6-yl, tetrazol-2-yl, pyrimidin-2-yl, quinolin-2-yl, pyrazol-2-yl, [4,5,6,7]-tetrahydrobenzothiazol- 2-yl, naphtho[2,1 -d]thiazol-2-yl, naphtho[1,2-d]thiazol-2-yl, quinazolin-2-yl, isothiazol-5-yl, isothiazol-3-yl, purin-8-yl and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl and hydroxy.

The compounds of the invention were tested for their ability to inhibit thrombin mediated hydrolysis. An in vitro enzyme assay was performed as well as an ex vivo assay. In addition, the compounds were tested in vitro for their ability to inhibit trypsin, as an indication of their selectivity.

Thrombin-catalyzed hydrolysis rates were measured spectrophotometrically using commercial human alpha-thrombin (American Diagnostica), a chromogenic substrate (Spectozyme® TH (H-D-HHT-Ala-Arg-pNA.2AcOH), American Diagnostica) in aqueous buffer (10 mM Tris, 10 mM Hepes, 150 mM NaCl, 0.1% PEG; pH 7.4), and a microplate reader (Molecular Devices). Changes in absorbance at 405 nm were monitored (Softmax, Molecular Devices), upon addition of enzyme, both with and without inhibitor present at 37° C. over 30 minutes. $IC_{50}$s were determined by fixing the enzyme and substrate concentrations and varying the inhibitor concentration (1 nM thrombin, 50 μM Spectozyme® TH). Michaelis-Menton kinetics were applied to the initial reaction slopes. Inhibition constants (Ki) were determined by fixing the enzyme and inhibitor concentrations and varying the substrate concentration (1 nM thrombin, 5–100 μM Spectozyme® TH). Michaelis-Menton kinetics were applied to the initial reaction slopes using the program K.Cat (Bio Metallics Inc.).

Trypsin-catalyzed hydrolysis rates were measured using the same method as the thrombin procedure. Bovine type 1 trypsin (Sigma) and Spectrozyme® TRY (Cbo-Gly-D-Ala-Arg-pNA.AcOH, American Diagnostics) replaced their thrombin equivalents in a concentration range of 3.2 U/ml trypsin and 0.1–0.3 mM Spectrozyme.

The $IC_{50}$ for representative compounds are listed in Table A. Representative Kis are listed in place of the $IC_{50}$ value for selected compounds. N-Me PPACK aldehyde and argatroban were used as reference standards and their values are listed below. The compound numbers in the table correspond to the examples described hereinafter.

An ex vivo assay was conducted to determine the duration of action of the compounds of Formula I. For this i.v. assay male rats (Long Evans, 350–500 g) were implanted with a teflon cannulae via the femoral artery while under anesthesia (pentobarbital i.p., 35 mg/kg). After surgery, the animals were individually housed in standard cages, fed with rat chow (Hanlan, #8604) and continuously infused with physiological saline to maintain arterial patency, (0.5 mL/h, intra arterial) using a spring-shielded swivelling tether connected to an infusion system. The animals were allowed to recover for at least 24 h after the surgical procedure.

A sample of blood was drawn from the animals 15 min before dosing with the inhibitor (0.25 mL blood is drawn into a syringe containing 0.025 mL of Sigma sodium citrate). The test compound was dispersed in water and delivered to the animal (0.25 mL) via the femoral vein. The inhibitor was given at a concentration (mg/mL) which produced 80% inhibition of $V_o$ in a plasma sample at 5 min after infusion. Blood was drawn from the arterial line (blood:sodium citrate, 0.25/0.025 mL) at regular intervals after dosing (5, 10, 15, 30, 60 and 120 min) and placed in a centrifuge tube. A plasma sample was obtained by centrifuging the blood at 10,000 rpm for 5 min. This sample is analyzed for thrombin inhibition using the chromogenic assay, described below.

The rate of increase in absorbance at 405 nm of synthetic peptides (50 μM Spectozyme® TH (H-D-H HT-Ala-Arg-pNA.2AcOH), American Diagnostica) is measured in the presence of plasma with a microplate reader (Molecular Devices) at 37° C. using an aqueous buffer (10 mM Tris, 10 mM Hepes, 150 mM NaCl, 0.1% PEG; pH 7.4). The buffer was added to the plasma samples (1:1) dilution prior to delivery to the microplate (1:5 and 1:50 for final plasma dilutions of 1:10 and 1:100 respectively) followed by the enzyme (1 nM human α thrombin). Datum was collected over a 30 min period and the initial rate of substrate hydrolysis ($V_0$ (mOD/min)) was calculated with an analysis program (Softmax, Molecular Devices).

The time to half plasma elimination (t ½) was calculated from the slope of $V_o$ vs. time, using the following equation: t ½=−1.6 slope. These datum are presented in Table A Bioavailability was determined by an ex vivo assay which incorporated hydrolysis rates from drug administered both i.v. and p.o. In this assay male rats were prepared as described above with a teflon tube implanted in their femoral artery. Blood was drawn from the animals 15 min before dosing with the inhibitor (0.25 mL blood was drawn into a syringe containing 0.025 mL of Sigma sodium citrate) and set aside for analysis. The test compound was dispersed in water (0.3–3.0 mg/mL final conc.) and delivered to the animals (0.25 mL) either i.v. or p.o.. Blood was drawn from the arterial line (blood:sodium citrate, 0.25/0.025 mL) at regular intervals after dosing (0.25, 0.5, 1.0, 2.0 and 3.0 h) and plasma was obtained by centrifuging the blood at 10,000 rpm for 5 min. This sample was analyzed for thrombin inhibition using the chromogenic assay, described below.

The rate of increase in absorbance at 405 nm of synthetic peptides (50 μM Spectozyme® TH (H-D-HHT-Ala-Arg-pNA.2AcOH), American Diagnostica) was measured in the presence of plasma with a microplate reader (Molecular Devices) at 37° C. using an aqueous buffer (10 mM Tris, 10 mM Hepes, 150 mM NaCl, 0.1% PEG; pH7.4). The buffer was added to the plasma samples (1:1) dilution prior to delivery to the microplate (1:5 and 1:50 for final plasma dilutions of 1:10 and 1:100 respectively) followed by the enzyme (1 nM human α thrombin). Datum were collected over a 30 min period and the initial rate of substrate hydrolysis ($V_0$(mOD/min)) was calculated with an analysis program (Softmax, Molecular Devices).

A standard curve was generated by adding of drug or vehicle (100 μL) to whole blood (900 μL) followed by incubating (5 min) and centrifuging to obtain plasma. The percentage of thrombin inhibition was calculated by comparing the $V_0$ of the vehicle to that of the drug treated samples. Datum from several runs were normalized with a statistical package (SAS) to generate a standard curve.

The percentage of thrombin inhibition in the treated animals was calculated by comparing the $V_0$ prior to treatment with the $V_0$ obtained from samples collected after treatment. The percent inhibition was applied to the standard curve (generated above) using the statistical package (SAS) and the quantity of drug in the sample was extrapolated.

Bioavailability (Bioavail.) was calculated from the plots of the extrapolated drug in sample vs. time for both i.v. and p.o. administration using the following equation:

%Bioavail. =(i.v. dose administered/p.o. dose administered)×(area under p.o. curve/area under curve i.v.)

TABLE A

| Cpd # | Thr $IC_{50}$ (μM) | Trp $IC_{50}$ (μM) | $t_{1/2}$ (min) | Bioavail, (%) |
|---|---|---|---|---|
| 1 | Ki = 0.00023 | Ki = 0.0031 | 19 | 1.2 |
| 2 | Ki = 0.0009 | Ki = 0.013 | | |
| 3 | 0.011 | Ki = 0.022 | 6 | |
| 4 | 0.019 | 0.006 | 16 | |
| 5 | 0.11 | 0.28 | 18 | |
| 6 | 42.0 | 6.34 | | |
| 7 | 26 | 50 | | |
| 8 | 3.5 | 19 | | |
| 9 | 4.0 | 0.012 | | |
| 10 | 40.15 | 7.74 | | |
| 11 | Ki = 0.42 | Ki = 6.01 | | |
| 12 | 0.003 | 0.003 | 43 | |
| 13 | 0.0070 | 0.002 | 25 | |
| 14 | 0.005 | 0.0030 | | |
| 15 | 0.0070 | 0.0030 | 16 | |
| 16 | 0.6830 | 0.2380 | | |
| 17 | 0.007 | 0.004 | 8 | |
| 18 | 0.21 | 0.13 | | |
| 19 | 0.026 | 0.005 | 14 | |
| 20 | 0.45 | 0.058 | | |
| 21 | 0.024 | 0.051 | 5 | |
| 22 | 1.519 | 18.404 | | |
| 23 | 0.928 | 0.238 | | |
| 24 | 0.106 | 0.014 | | |
| 25 | 0.003 | 0.003 | 14 | |
| 26 | Ki = 38 | Ki = 180 | | |

TABLE A-continued

| Cpd # | Thr IC$_{50}$ (μM) | Trp IC$_{50}$ (μM) | t$_{1/2}$ (min) | Bioavail, (%) |
|---|---|---|---|---|
| 27 | Ki = 1.2 | Ki = 12 | | |
| 28 | 0.111 | 1.199 | 15 | |
| 29 | 0.003 | 0.002 | 14 | |
| 30 | 0.029 | 0.002 | 6 | |
| 31 | 50.0 | 0.0800 | | |
| 32 | 0.0020 | 0.0020 | 19 | |
| 33 | 0.0070 | 0.0020 | 18 | |
| 34 | 0.0380 | 0.0030 | 26 | |
| 35 | 0.2010 | 0.0020 | 11 | |
| 36 | 0.001 | 0.001 | | |
| 37 | 0.0020 | 0.0010 | 42 | |
| 38 | 29.9 | 38.7 | | |
| 39 | 100 | 100 | | |
| 40 | 20.5 | 7.01 | | |
| 41 | 0.002 | 0.001 | | |
| 42 | 0.0040 | 0.0020 | | |
| 43 | 0.200 | 0.0020 | | |
| 44 | 50.0 | 4.38 | | |
| 45 | 0.371 | 0.009 | | |
| 46 | 0.015 | 0.003 | | |
| 47 | 0.003 | 0.004 | | |
| 48 | 100 | 0.684 | | |
| 49 | 12.9 | 6.88 | | |
| 50 | 0.002 | Ki = 0.0020 | | |
| 51 | 0.0170 | 0.0070 | 17 | |
| 52 | 0.012 | 0.005 | 8 | |
| 53 | 45.5 | 7.44 | | |
| 54 | 0.11 | 0.013 | 15 | |
| 55 | 0.83 | 0.0086 | | |
| 56 | 21.0 | 0.02790 | | |
| 57 | 19.6 | 0.182 | | |
| N—Me PPACK | Ki = 0.010 | Ki = 0.0039 | | |
| Argatroban | Ki = 0.010 | Ki = 2.9 | | |

As indicated by Table A, the compounds of Formula I may be used in pharmaceutical compositions to treat patients (humans and other primates) with thrombotic disorders in a similar manner as known heparins and coumarins. The compounds can be administered by any parenteral route (intraperitoneal, intraperitoneal, subcutaneous, dermal patch), where the preferred route is intravenous infusion. Infusion doses can range from about 0.1–300 μg/kg/min of inhibitor, admixed with a pharmaceutical carrier over a period ranging from several minutes to several days. Selected compounds can also be administered by the oral route in doses ranging from about 1–100 mg/kg.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In addition to the treatment of thrombotic disorders, the compounds of Formula I may be used to prevent coagulation of stored blood samples and as coatings on medical devices such as stents and orthopedic devices. Generally they may be used in any circumstance where one seeks to inhibit coagulation by placing the compounds in contact with the medium containing thrombin. Those experienced in the use of anticoagulant agents, may find a variety of other uses for the thrombin inhibitors of this invention. These uses are considered to be within the scope of this invention, for this invention contemplates the use of compounds of Formula I as antithrombotic agents.

Yet another use for the compounds of the invention is as trypsin inhibitors. Inhibitors of trypsin have been used clinically in the treatment of pancreatic disorders, such as pancreatitis. The IC$_{50}$ values for the compounds of the invention compare favorably with the pancreatic agents camostat mesilate and nafamostat (IC$_{50}$ s, 1×10$^{-8}$ and 1.3× 10$^{-8}$ respectively). The compounds of Formula I may be used in the same manner as those therapeutic agents.

In order to illustrate the invention the following examples are included. These examples do not limit the invention. They are only meant to suggest a method of practicing the invention. Those skilled in the art may find other methods of practicing the invention, which are obvious to them. However those methods are deemed to be within the scope of this invention.

EXAMPLES 1 and 2

N-METHYL-D-PHENYLALANYL-N-[4-[(AMINOIMINOMETHYL)AMINO]-1S-[(BENXOTHIAZOL-2-YL)CARBONYL]BUTYL]-L-PROLINAMIDE Cpd#1

N-METHYL-D-PHENYLALANYL-N-[4-[(AMINOIMINOMETHYL)AMINO]-1R-[(BENXOTHIAZOL-2-YL)CARBONYL]BUTYL]-L-PROLINAMIDE Cpd#2

STEP a    1a

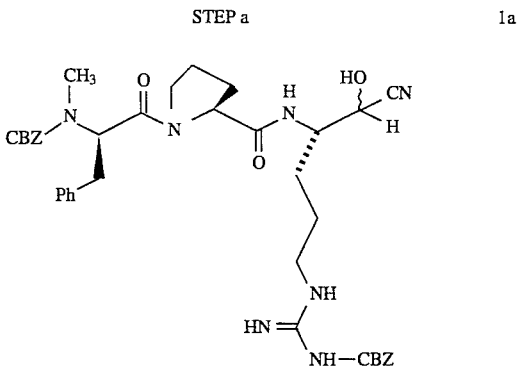

A mixture of N-CBZ-N-methyl-D-phenylalanyl-L-prolyl-N$^G$-CBZ-L-arginine-aldehyde (9.92 g, 14.5 mmol; U.S. Pat. No. 4,703,036), CH$_2$Cl$_2$ (48 mL), acetone cyanohydrin (4.0 mL, 43.4 mmol), and triethylamine (1.2 mL, 8.7 mmol) was stirred at room temperature under argon for 3 h. An additional portion of acetone cyanohydrin (1.3 mL, 14.2 mmol) was added followed by another hour of stirring. The mixture was concentrated in vacuo and partitioned between water and ethyl acetate. The resulting organic layer was washed with portions of water and brine, dried (Na$_2$SO$_4$) and concentrated in vacuo. The residue was triturated with several portions of hexane, and the resulting solid precipitate was dried in vacuo to give the cyanohydrin intermediate 1a, as a solid.

STEP b                    1b

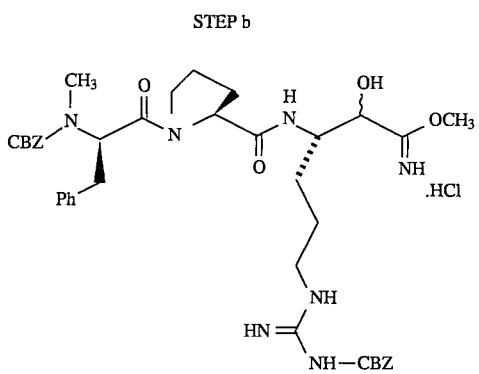

Gaseous HCl (51 g) was bubbled into a solution of cyanohydrin 1a (9.3 g, 13.1 mmol) and MeOH (200 mL) at −50° to −70° C. under an atmosphere of argon over 1.5 h. The reaction mixture was placed in a refrigerator at 0° C., monitored (TLC and NMR) over 3 days, and transferred to a separatory funnel under argon. The reaction mixture was added dropwise to a stirred mixture of water (700 mL), ethyl acetate (250 mL) and NaHCO$_3$ (159 g, 1.4 mol), at 0°–6° C. The pH of the quenching solution was monitored and not allowed to go below pH 6.8. Additional portions of water and NaHCO$_3$ were added (as dictated by the measured pH) until the reaction mixture was neutralized. The resulting mixture was filtered through a filter aid, leaving a filtrate, which was washed with several portions of ethyl acetate. The combined organic layers were washed with brine, dried (Na$_2$SO$_4$), and concentrated in vacuo to give the HCl salt of imidate 1b, as a solid.

STEP c                    1c

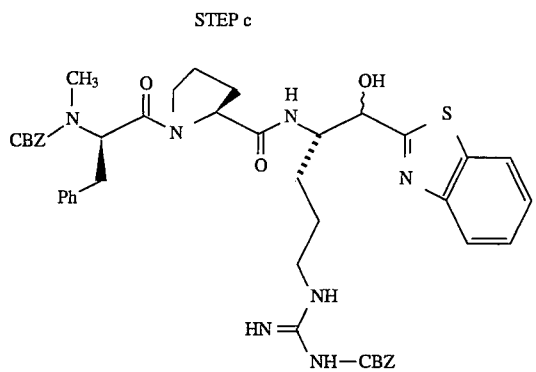

2-Aminothiophenol (18.53, 18.52 mmol) was added to a degassed solution of imidate 1b (7.23 g, 9.26 mmol) in absolute ethanol (290 mL) at room temperature under an atmosphere of argon. The resulting mixture was heated at reflux for 4.75 h, cooled to room temperature, exposed to atmospheric oxygen at room temperature for 18 h atmosphere and concentrated in vacuo. The residue was purified by chromatography on silica gel eluting with CH$_2$Cl$_2$/methanol (95:5) to give the hydroxy benzothiazole intermediate 1c as a white foam.

STEP d                    1d

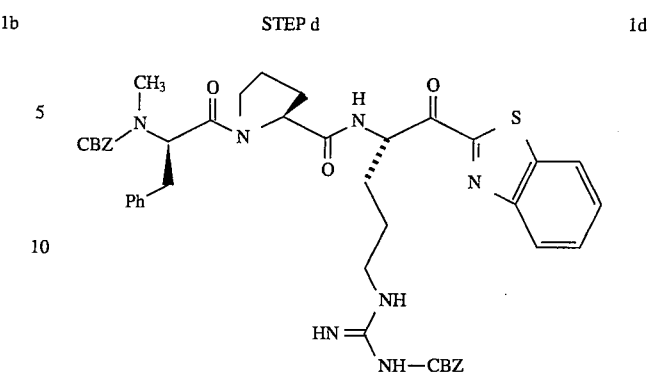

The Dess-Martin periodinane (1.59 g, 3.76 mmol) was added to a solution of 1c (3.08 g, 3.76 mmol) in CH$_2$Cl$_2$ (40 mL) at room temperature under an atmosphere of argon. The resulting mixture was stirred for 45 rain and an additional potion of periodinane (1.2 g, 2.83 mmol) was added, followed by another 15 min of stirring. The excess periodinane was consumed by the addition of 8 mL of quench solution (25 g Na$_2$S$_2$O$_3$ in 100 mL saturated aqueous NaHCO$_3$) diluted with ethyl acetate (300 mL), and stirred at room temperature for 15 min. The resulting aqueous layer was isolated and extracted with several potions of ethyl acetate and the combined organic extracts were washed with successive potions of water and brine, dried (Na$_2$SO$_4$) and concentrated in vacuo to give the ketone 1d, as a white foam.

STEP e

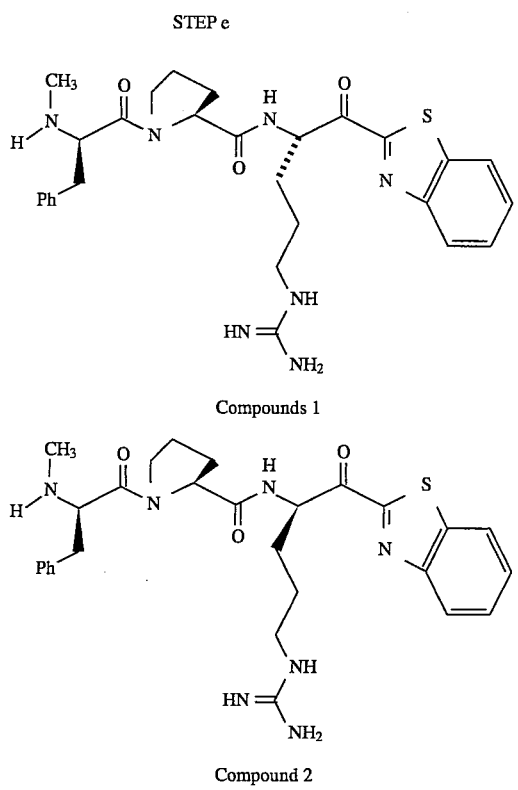

Compounds 1

Compound 2

The intermediate ketone 1d (2.97 g, 3.63 mmol) and anisole (10 mL) were placed in a Teflon reaction tube of an HF apparatus under anhydrous conditions and cooled to −78° C. HF (15–20 mL) was distilled into this tube and upon completion of addition, the temperature of the mixture was allowed to rise to 0° C. This mixture was stirred for 2 h, concentrated in vacuo and triturated with several portions of ether to give a yellow solid. This solid was purified by reverse-phase, HPLC using water/acetonitrile/TFA (70:30:0.2) to give compounds 1 and 2. Each diastereomer was lyophilized to give the desired products as white foams where compound 1 is 91.5% of the material collected. Compound 1 (L-arginine diastereomer): FAB-MS m/z 550 (MH$^+$); [α]$_D^{20}$=-72.5°, (c 1.00, MeOH).
Anal. Calc'd for $C_{28}H_{35}N_7O_3S \cdot 2.75$ TFA·0.5 H$_2$O: Calculated: C, 46.12; H, 4.47; N, 11.24; H$_2$O, 1.03. Found: C, 46.13; H, 4.37; N, 11.35; H$_2$O, 1.27.
Compound 2 (D-arginine diastereomer): FAB-MS m/z 550 (MH$^+$); [α]$_D^{20}$=-67.5° (c 0.67, MeOH).
Anal. Calc'd for $C_{28}H_{35}N_7O_3S \cdot 3$ TFA·2 H$_2$O: Calculated: C, 44.01; H, 4.56; N, 10.57; H$_2$O, 3.88. Found: C, 44.11; H, 4.34; N, 10.96; H$_2$O, 3.80.

EXAMPLE 3

STEP a 3a

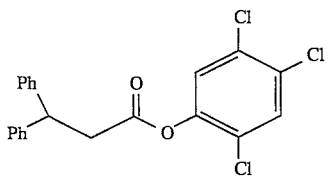

A solution of dicyclohexylcarbodiimide (18.24 g, 88.4 mmol) in THF (35 mL) was added dropwise to a stirred solution of 3,3-diphenylpropionic acid (20.0 g, 88.4 mmol), 2,4,5-trichlorophenol (17.45 g, 88.4 mmol) and THF (50 mL) under argon at −20° C. The reaction mixture was stirred at −20° C. for 2.5 h, placed in a refrigerator at 0° C. for 16 h, and filtered through filter aid. The mother liquor was concentrated in vacuo and recrystallized from ethanol to give the activated ester 3a, as a solid.

STEP b 3b

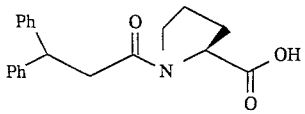

Activated ester 3a (15.0 g, 37.0 mmol) was added to a mixture of L-proline (4.26 g, 37.0 mmol), triethylamine (5.15 mL) and pyridine (45 mL) at 5° C. under argon. The reaction mixture was allowed to warm to room temperature, stirred for 76 h, and concentrated in vacuo. An aqueous solution of NaHCO$_3$ (3.42 g/130 mL) and ether (100 mL) were added to the residue and the resulting mixture was stirred at room temperature for 45 min. The organic layer was extracted several times with water. The combined aqueous layer was extracted with two portions of ether, acidified with 1N HCl and extracted with several portions of ethyl acetate. The combined ethyl acetate extracts were washed with brine, dried (MgSO$_4$) and concentrated ill vacuo to give the proline intermediate 3b, as a solid.

STEP c 3c

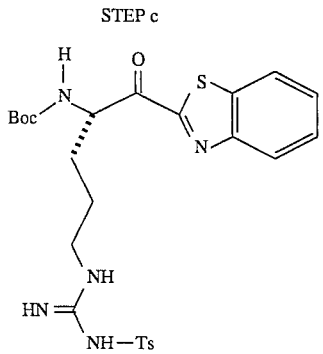

1.6M n-Butyl lithium/hexane (16 mL, 25.6 mmol) was added to a solution of benzothiazole (3.7 mL, 33.9 mmol) and anhydrous THF (114 mL) at −78° C. under argon. The reaction mixture was stirred at −78° C. for 15 min and a solution of N-α-Boc-N$^G$-tosyl-L-arginine N,O-dimethyl amide (800 mg, 1.69 mmol; DiMaio, et al. *Journal of Medicinal Chemistry* 1992, 35, 3331) and THF (43 mL) was added via cannula while keeping the temperature below 70° C. The resulting mixture was stirred for 1.66 h at −78° C., poured into a saturated aqueous NH$_4$Cl solution (600 mL), stirred vigorously for 15 min, and extracted with several portions of ethyl acetate. The combined ethyl acetate extracts were washed with successive portions of water and brine, dried (Na$_2$SO$_4$) and concentrated in vacuo. The residue was purified by column chromatography on silica gel eluting with ethyl acetate/hexane (5:2) to give the benzothiazole derivative 3c as an oil.

STEP d 3d

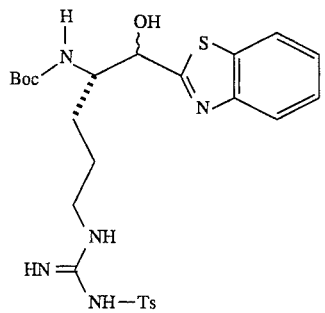

Sodium borohydride (63.8 mg, 1.69 mmol) was added dropwise to a solution of benzothiazole 2c (307 mg, 0.563 mmol) in MeOH (10 mL) at −20° C. under argon. This mixture was stirred at approximately −20° C. for 40 min and acetone (2 mL) was slowly added. The resulting mixture was allowed to warm up to room temperature over 1.25 h, concentrated in vacuo, and partitioned between ethyl acetate and water. The aqueous layer was extracted with several portions of ethyl acetate. The combined ethyl acetate extracts were washed with brine, dried (Na$_2$SO$_4$), and concentrated in vacuo to give the alcohol 3d, as a pale yellow foam.

STEP e

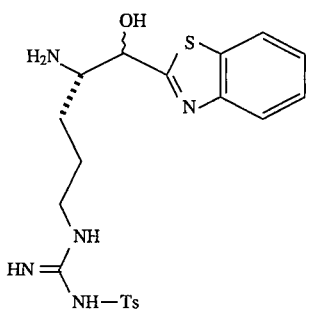

3e

A solution of alcohol 3d (0.27 g, 0.49 mmol) in 10 mL of TFA/CH$_2$Cl$_2$ (1:4) was stirred at room temperature under argon for 1.5 h. The resulting mixture was concentrated in vacuo to give the TFA salt of 3e, as an oil.

STEP f

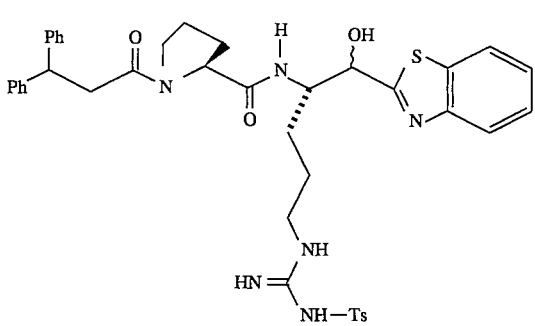

3f

A solution of the TFA salt of amine 3e (0.49 mmol), triethylamine (0.25 mL), intermediate 3b (158 mg, 0.49 mmol), hydroxybenzotriazole hydrate (111 mg, 0.54 mmol) in acetonitrile (10 mL) was treated with DCC (73 mg, 0.54 mmol) and stirred at room temperature under argon for 20 h. The resulting mixture was filtered and the solids were washed with several portions of acetonitrile. The filtrate and washings were combined, concentrated in vacuo and partitioned between ethyl acetate and water. The organic layer was washed with successive portions of 1N HCl, water, saturated aqueous NaHCO$_3$, and brine; dried (Na$_2$SO$_4$) and concentrated in vacuo. The residue was purified using preparative TLC on silica gel, eluting with CHCl$_3$/MeOH benzothiazole 3f, as a tacky solid.

STEP g

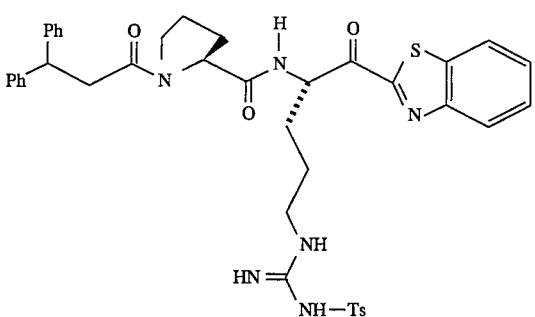

3g

A mixture of 3f (7.2 mg, 0.0096 mmol) CH$_2$Cl$_2$ (1 mL) and Dess-Martin periodinane (8.1 mg, 0.019 mmol) was stirred at room temperature under nitrogen for 1 h, treated with 4 mL of quench solution (25 g Na$_2$S$_2$O$_3$ in 100 mL saturated aqueous NaHCO$_3$), and diluted with water and CH$_2$Cl$_2$. The resulting organic layer was washed with water, dried (Na$_2$SO$_4$) and concentrated in vacuo to give the ketone 3g, as a foam.

STEP h

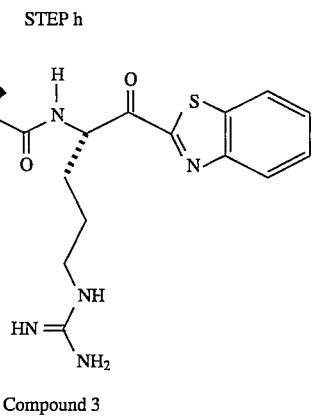

Compound 3

A mixture of anisole (1 mL) and ketone 3g (137 mg, 0.17 mmol) was placed in a Teflon reaction tube, attached to an HF apparatus, and cooled to −78° C. HF (5 mL) was distilled into the reaction tube and the resulting mixture was stirred at 0° C. for 3 h. The HF was removed in vacuo and the mixture was triturated with three portions of ether. The resulting precipitate was filtered, air dried, dissolved in acetonitrile/water (1:1) and purified by reverse-phase HPLC using CH$_3$CN+2% TFA/H$_2$O +0.016% TFA as an eluent. The desired fractions were concentrated in vacuo and lyophilized to give compound 2 as a 1:3 mixture of D and L arginine diastereomers; IR (KBr, cm$^{-1}$) 1674, 1450, 1204, 1135; $[\alpha]_D^{19}$ =−74.0 (c 0.60, MeOH); mp=106°–120° C. Anal. Calc'd for C$_{33}$H$_{36}$N$_6$O$_3$S·1.75 TFA·0.33 H$_2$O: Calculated: C, 52.96; H, 5.02; N, 10.15; H$_2$O=3.81. Found: C, 53.27; H, 5.13; N, 10.34; H$_2$O=3.86.

EXAMPLE 4

STEP a

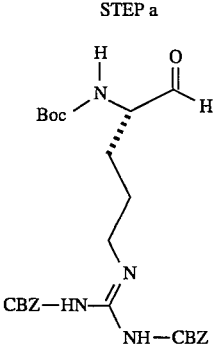

4a 1,1'-Carbonyldiimidazole (0.65 g, 4.05 mmol) was added to a mixture of N-α-Boc-N$^G$,N$^{G'}$-di-CBZ-L-arginine (92.0 g, 3.69 mmol) and THF at 0° C. under argon and the resulting mixture was stirred for an hour at 0° C. The mixture was cooled to −48° C. and a solution of 1M DIBAL/hexane (10.3 mL, 10.3 mmol) was added at a rate which kept the reaction temperature between −48° and −42° C. The resulting mixture was stirred for another 15 min at −48° C. and an aqueous solution of KHSO$_4$ (1.4 g/5.0 mL) was added at a temperature of between −40° and −28° C. The mixture was allowed to warm up to room temperature, CH$_2$Cl$_2$ was added, and the resulting solids were filtered and washed with additional portions of CH$_2$Cl$_2$. The collected filtrates were washed with water, dried (MgSO$_4$) and concentrated in vacuo. The residue was purified by crystallization from i-PrOH and hexane to give the aldehyde 4a, as a solid.

STEP b                                                          4b

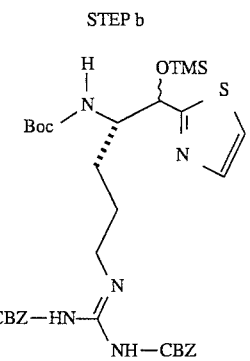

A mixture of aldehyde 4a, (0.765 g, 1.36 mmol), $CH_2Cl_2$ (5 mL) and 2-(trimethylsilyl)thiazole (1.07 g, 6.8 mmol) was stirred at room temperature under argon for 16 h. The reaction mixture was concentrated in vacuo to give 4b as an oil.

STEP c                                                          4c

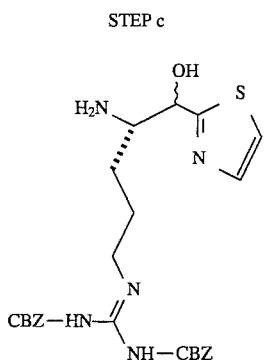

Trifluoroacetic acid (6 mL) was added slowly to a stirred mixture of thiazole 4b (1.36 mmol) and $CH_2Cl_2$, (30 mL) at room temperature under argon. The reaction mixture was stirred for 6 h and concentrated in vacuo. The residue was purified by flash chromatography on silica gel using $CH_2Cl_2$/MeOH/$NH_4OH$ (95:4.5:0.5) as an eluent to give a single diastereomer. The isolated product was dissolved in $CH_2Cl_2$, dried ($K_2CO_3$), filtered and concentrated in vacuo to give the alcohol 4c, as a glassy oil.

STEP d                                                          4d

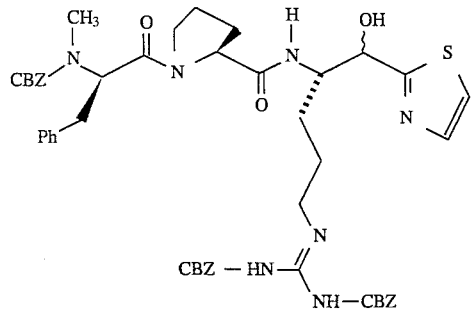

DCC (0.079 g, 0.38 mmol was added to a mixture of alcohol 4c (0.18 g, 0.35 mmol), (CBZ)-N-methyl-D-phenyalanyl-L-proline (0.14 g, 0.35 mmol; U.S. Pat. No. 4,703,036), hydroxybenzotriazole hydrate (0.053 g, 0.38 mmol) and $CH_3CN$ (4.5 mL) at room temperature. The reaction mixture was stirred for 3.5 h and the resulting solid precipitate was washed with portions of $CH_3CN$. The combined filtrates were concentrated in vacuo and partitioned between in ethyl acetate and water. The organic layer was washed with successive portions of water and brine, dried ($MgSO_4$) and concentrated in vacuo. The residue was purified by chromatography (silica gel, $CH_2Cl_2$/MeOH (95/5)) to give the coupled alcohol 4d, as a white foam.

STEP e                                                          4e

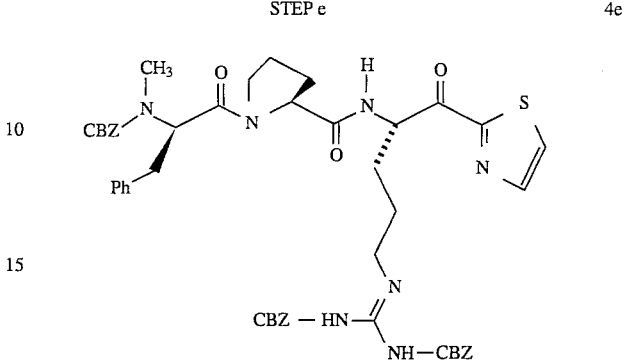

A solution of the alcohol 4d (0.14 g, 0.15 mmol) and $CH_2Cl_2$ (3 mL) was added in one portion to a mixture of Dess-Martin periodinane (76 mg, 0.179 mmol) and $CH_2Cl_2$ (4 mL) at room temperature. The reaction mixture was stirred for 35 min and a few additional milligrams of Dess-Martin periodinane was added. The resulting mixture was stirred for another 10 min and 10 mL of quench solution (25 g $Na_2S_2O_3$ in 100 mL saturated aqueous $NaHCO_3$) was added followed by an additional 10 min of stirring. The resulting mixture was partitioned between ethyl acetate and water and stirred for another 5 min. The organic layer was washed with several portions of water and brine, dried ($MgSO_4$) and concentrated in vacuo to give the ketone 4e, as a colorless glass.

STEP f

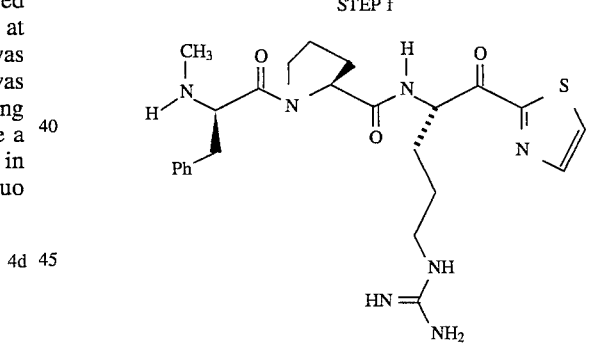

Compound 4 (RWJ 50026)

Ketone 4e (0.13 g, 0.144 mmol) and anisole (1 mL) were placed in a Teflon reaction tube of an HF apparatus under anhydrous conditions and cooled to −78° C. HF (5–10 mL) was distilled directly into this flask, the temperature of the mixture was allowed to rise to 0° C. and this mixture was stirred for 1.5 h. The HF was removed in vacuo and the residue was triturated with several portions of ether to give a solid. This solid was purified by reverse-phase HPLC eluting with water/acetonitrile/TFA (50:50:0.2) and concentrated in vacuo. The residue was dissolved in water and adjusted to pH 6.48 with freshly rinsed Amberlite® IRA-400 ($OH^-$) ion exchange resin and aqueous 0.1M TFA. The solid precipitates were isolated by filtration and the filtrate was lyophilized to give compound 4 as a white solid.

Anal. Calc'd for $C_{24}H_{33}N_7O_3 \cdot 2\ C_2HF_3O_4 \cdot 0.2\ H_2O$: Calculated: C, 44.88; H, 5.03; N, 13.08; $H_2O$, 2.88. Found: C, 44.49; H, 4.93; N, 12.98; H₂O, 2.64.

EXAMPLE 5

STEP a

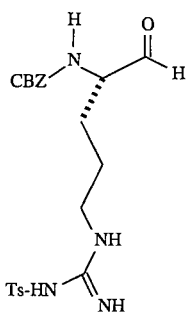

5a 1,1'-Carbonyldiimidazole (9.89 g, 0.053 mmol) was added in one portion to a stirred solution of N-α-CBZ-N$^G$-tosyl-L-arginine (25.2 g, mmol) and THF (160 mL) at 0°–10° C. After 1 h, the reaction mixture was cooled to –42° C. and 1M DIBAL/hexane (130 mL, 1.30 mmol) was added over 30 min. The resulting mixture was stirred for another 30 min at –42° C. The reaction was quenched by the slow addition of 1.2M HCL (365 mL) and the reaction temperature was allowed to warm to room temperature. This mixture was treated with 0.6M HCl (360 mL) and CHCl₃ (400 mL) and stirred at room temperature for 2.5 h. The aqueous phase was washed with several portions of CHCl₃ and the combined organic extracts were washed with successive portions of water, dried (Na₂SO₄) and concentrated in vacuo to give the aldehyde 5a as a solid; FAB-MS m/z 447 (MH)⁺

STEP b

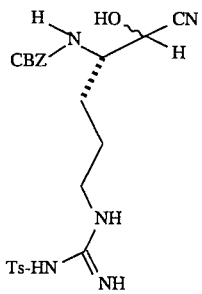

5b

KCN (6.0 g, 92 mmol) was added to a stirred mixture of aldehyde 4a (22.0 g, 49 mmol) in MeOH (60 mL), H₂O (60 mL) and ethyl acetate (110 mL) and stirred at 22° C. for 16 h. The resulting aqueous layer was extracted with several portions of ethyl acetate and the combined organic extracts were washed with water, dried (Na₂SO₄) and concentrated in vacuo to give the nitrile 5b as a foam; FAB-MS m/z 474 (MH)⁺.

STEP c

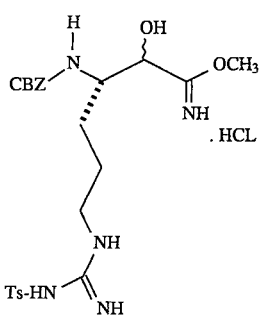

5c

Anhydrous HCl (g) was bubbled into a solution of nitrile 5b (8.0 g, 16.9 mmol) and anhydrous MeOH (162 mL) at –78° C. at a rate such that the temperature does not exceed –40° C. After the addition the reaction was stirred for 30 min at 20° C. The reaction mixture was added to a vigorously stirred saturated aqueous NaHCO₃ while maintaining the pH above pH 6. After neutralization, the pH was adjusted to pH 4.0 with glacial acetic acid and ethyl acetate (350 mL) was added. The mixture was stirred for 4 h, separated and the aqueous layer was extracted with ethyl acetate three times. The combined ethyl acetate extracts were washed with water, saturated aqueous NaHCO₃ as well as brine, dried (Na₂SO₄) and concentrated in vacuo to give the imidate 5c, as a white solid; FAB-MS m/z 507 (MH)⁺.

STEP d

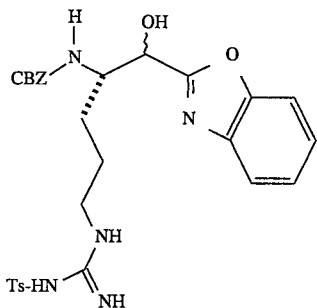

5d

A solution of imidate 5c (1.00 g, 1.84 mmol), 2-aminophenol (0.22 g, 2.03 mmol) and absolute EtOH (40 mL) was heated at reflux under N₂ for 24 h and concentrated in vacuo. The residue was purified by chromatography on silica gel eluting with CH₂Cl₂/MeOH (95:5) to give the benzoxazole 5d as a white foam; mp 81°–91° C.; [α]$_D^{25}$ –2.9 (c, 0.68, CHCl₃).

Anal. Calc'd for C₂₈H₃₁N₅O₆S ·0.6H₂O: Calculated: C, 58.34; H, 5.14; N, 12.15; H₂O, 1.87 Found: C, 58.32; H, 5.14; N, 11.97; H₂O, 1.67

STEP e

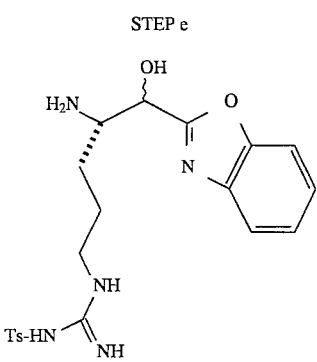

A mixture of 5d (0.87 g, 1.53 mmol), 20% Pd(OH)$_4$/C (0.21 g) and absolute EtOH (19 mL) was placed on an atmospheric hydrogenator and stirred under H$_2$ for 16 h. The resulting mixture was filtered, through a filter aid and concentrated in vacuo to give the free amine 5e as a yellow foam.

STEP f

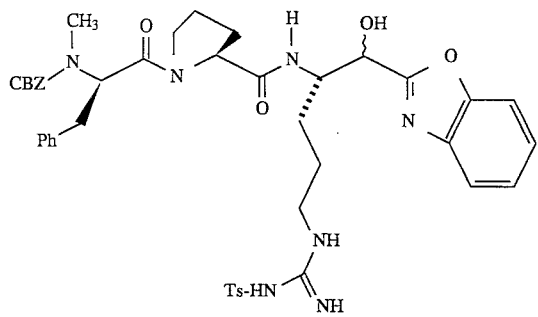

A solution of DCC (0.25 g, 1.1 mmol) and CH$_3$CN (1 mL) was added dropwise to a solution of 1-hydroxybenztriazole hydrate (0.16 g, 1.2 mmol), amine 5e (0.47 g, 1.1 mmol), CBZ N-methyl-phenylalanyl-proline (0.44 g, 1.1 mmol) and CH$_3$CN (15 mL) under N$_2$. The reaction mixture was stirred for 3.5 h, filtered and the resulting filter cake was washed with several portions of CH$_3$CN. The combined filtrate was concentrated in vacuo, dissolved in ethyl acetate, washed with successive portions of water and brine, dried (MgSO$_4$) and concentrated in vacuo. The residue was purified by column chromatography on silica gel eluting with CH$_2$Cl$_2$/MeOH (93:7) to give the coupled alcohol 5f, as a yellow glass.

STEP g

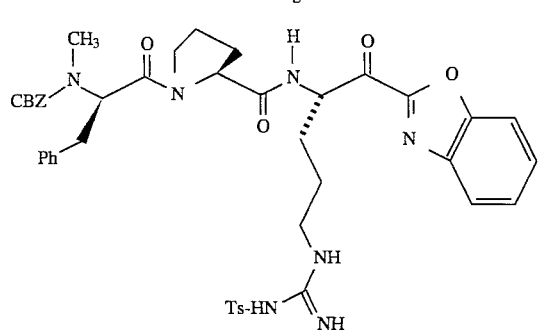

A solution of alcohol 5f (0.45 g, 0.56 mmol) and anhydrous CH$_2$Cl$_2$ (5 mL) was added to a stirred mixture of Dess-Martin periodinane (300 mg, 0.73 mmol) and anhydrous CH$_2$Cl$_2$ (20 mL) at room temperature under argon. The reaction mixture was stirred for 30 min and another portion of Dess-Martin periodinane (50 mg, 0.12 mmol) was added followed by another 10 min of stirring at room temperature. To the stirred reaction mixture was added 30 mL of quench solution (25 g Na$_2$S$_2$O$_3$ in 100 mL saturated aqueous NaHCO$_3$) followed by a portion of ethyl acetate. The resulting organic layer was washed with successive portions of saturated aqueous NaHCO$_3$ and brine, dried (MgSO$_4$) and concentrated in vacuo to give the ketone 5g, as a foam; FAB-MS m/z 882 (MH)$^+$.

STEP h

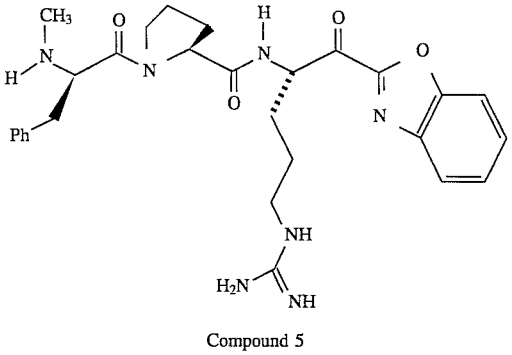

Compound 5

Ketone 5g (0.45 g, 0.54 mmol) and anisole (ca. 2.0 mL) were placed in a Teflon reaction tube of an HF apparatus under anhydrous conditions and cooled to –78° C. HF (0.5–1.0 mL) was distilled directly into this flask, the temperature of the mixture was allowed to rise to 0° C. and this mixture was stirred at 0° C. for 4 h. The HF was removed in vacuo and the residue was triturated with several portions of ether to give a yellow solid, which was purified by reverse-phase HPLC eluting with water/acetonitrile/TFA (70:30:0.2). The fractions containing the desired product were concentrated in vacuo and lyophilized to give compound 5 as a powder; mp 81°–91° C.; $[\alpha]_D^{25}$ –63.3 (c 0.58, MeOH); FAB-MS m/z 534 (MH)$^+$.

Anal. Calc'd for $C_{28}H_{35}N_7O_4 \cdot 4 \cdot (C_2HF_3O_2) \cdot 2.5\ H_2O$ Calculated: C, 41.97; H, 4.25; N, 9.52; H$_2$O, 3.93. Found: C, 42.26; H, 4.42; N, 9.87; H$_2$O, 4.27.

EXAMPLE 6

STEP a

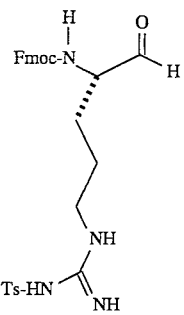

1,1-Carbonyldiimidazole (1.8 g, 11.0 mmol) was added to a solution of N-α-Fmoc-N$^G$-tosyl-L-arginine (6.0 g, 10.0 mmol) in anhydrous THF (30 mL) at 0° C. under argon and stirred at 0° C. for 1.5 h. The reaction mixture was cooled to –48° C. and 1M DIBAL (28 mL, 28 mmol) was added dropwise over 20 min. The resulting mixture was stirred for another 1.5 h and 1.2N HCL (67 mL) was added with stirring. The mixture was allowed to warm up to room temperature and partitioned between 0.6N HCl (65 mL) and chloroform. The resulting aqueous layer was washed with several portions of chloroform. The combined organic extracts were washed successive portions of water and brine, dried (Na₂SO₄) and concentrated in vacuo to the aldehyde 6a as a white flakey solid.

STEP b

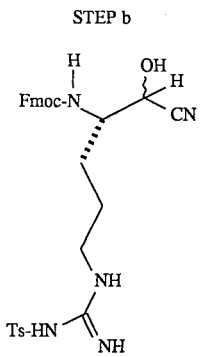

6b

A solution of KCN (1.44 g; 22 mmol) and H₂O (125 mL) was added to a solution of aldehyde 6a (5.9 g, 11.0 mmol) in ethyl acetate (250 mL) and the resulting mixture was stirred for 40 h at room temperature under argon. The organic layer was separated and the aqueous layer was washed with three portions of ethyl acetate. The combined ethyl acetate extracts were washed with brine, dried (Na₂SO₄), concentrated in vacuo and stored in the refrigerator under argon. The residue was partitioned between ethyl acetate (100 mL) and saturated aqueous NaHCO₃ (200 mL) and the pH was maintained at 7.0 by the addition of solid NaHCO₃. The solid NaHCO₃ was removed by filtration and the resulting aqueous layer was washed with several portions of ethyl acetate. The combined organic layer was washed twice with brine, dried (MgSO₄) and concentrated in vacuo to give the cyanohydrin 6b as a white solid; FAB-MS m/z 562 (MH)⁺.

STEP c

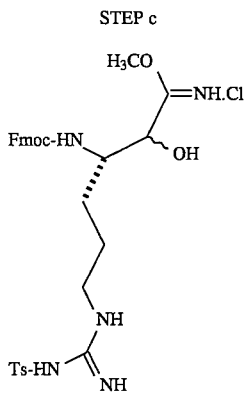

6c

HCl (21 g) was bubbled into a solution of nitrile 6b (3.0 g, 5.34 mmol) and methanol (53 mL) under argon of at a temperature of less than −40° C. over 20 min. This reaction vessel was closed under nitrogen and placed in a freezer at −15° C. for 46 h and concentrated in vacuo at room temperature. The residue was partitioned between saturated aqueous NaHCO₃ solution (250 mL) and ethyl acetate. The organic layer was washed with two portions of brine, dried (MgSO₄) and concentrated in vacuo to give the imidate 6c, as a solid.

STEP d

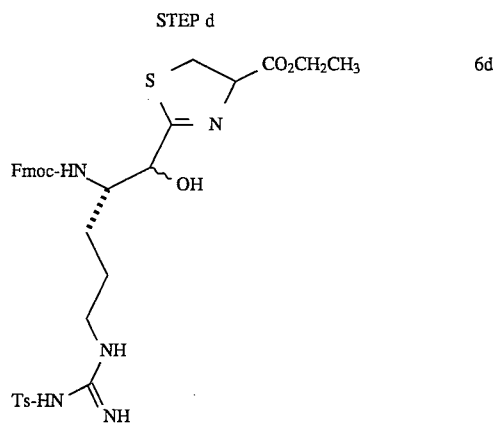

6d

Cysteine ethyl ester hydrochloride (1.97 g, 10.6 mmol) was added to a solution of imidate 6c (3.30 g, 5.3 mmol) and CH₂Cl₂ (100 mL) and the resulting mixture was stirred under argon at room temperature for 3 h. The solid precipitate was removed by filtration and the filtrate was concentrated in vacuo. The residue was purified by HPLC using CH₂Cl₂/methanol (97:3) as an eluent to give the thiazoline derivative 6d, as a solid; FAB-MS m/z 694 (MH)⁺.

STEP e

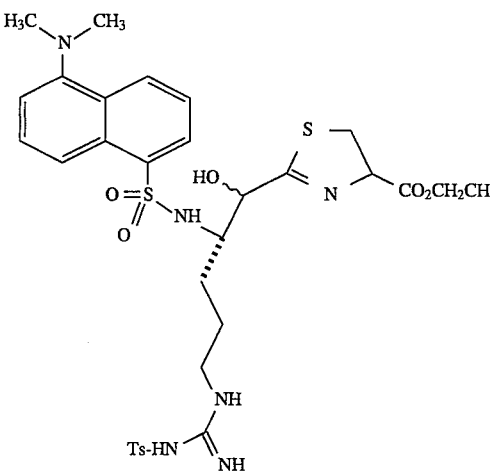

6e

Diethylamine (2.5 mL, 24.2 mmol) was added dropwise to a stirred solution of derivative 6d (2.20 g, 3.17 mmol) in anhydrous acetonitrile (50 mL) at −5° C. and the reaction was allowed to warm up to room temperature over 18 h. The residue was concentrated in vacuo, dissolved in anhydrous CH₂Cl₂, and concentrated in vacuo again. The residue was triturated with several portions of hexane and concentrated in vacuo to give the amine 6e as an oil; FAB-MS m/z 472 (MH)⁺.

STEP f

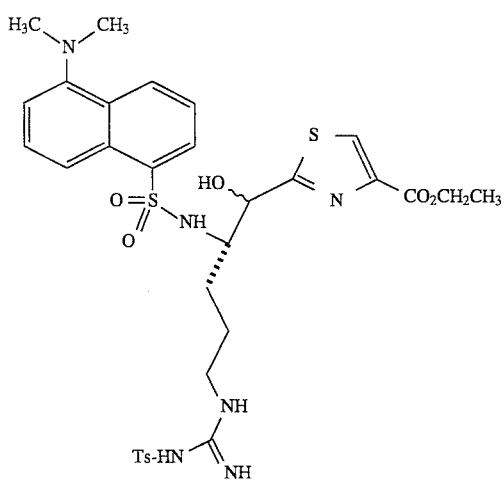

Dansyl chloride (890 mg, 3.3 mmol) was added to a solution of amine 6e (2.21 g, 3.1 mmol) and CH$_2$Cl$_2$ at −5° C. under argon. Upon completion of addition, the reaction mixture was stirred at room temperature for 1 h. The resulting mixture was concentrated in vacuo and partitioned between CHCl$_3$ and saturated aqueous NaHCO$_3$. The organic layer was washed with brine, dried (K$_2$CO$_3$), and concentrated in vacuo. The residue was purified by chromatography on silica gel eluting with CH$_2$Cl$_2$/MeOH (97:3) to afford protected amine 6f; FAB-MS m/z 705 (MH)$^+$.

STEP g

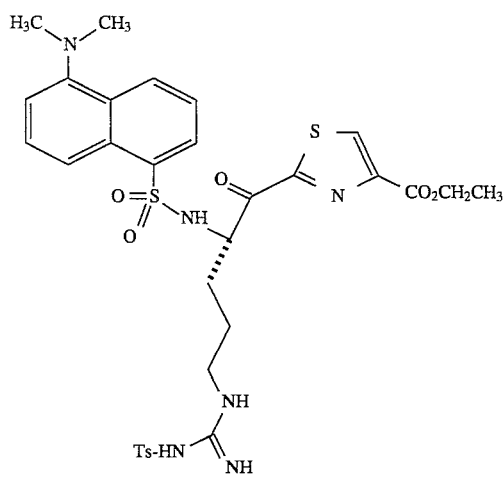

Activated MnO$_2$ (0.75 g) was added to a solution of amine 6f (0.70 g, 1.49 mmol) and CH$_2$Cl$_2$ (25 mL) and the resulting mixture was stirred overnight at room temperature. An additional portion of MnO$_2$ (0.75 g) was added and this mixture was stirred for 4 h at room temperature. Yet another portion of MnO$_2$ (0.75 g) was added and the resulting mixture was stirred for 16 h at room temperature. The reaction mixture was filtered once through filter aid and then through a Nylon 66 filter (0.45 μm) using CHCl$_3$/MeOH to wash the filter cakes. The combined washings were dried (Na$_2$SO$_4$) and concentrated in vacuo. The residue was purified by HPLC using silica gel and CH$_2$Cl$_2$/MeOH (97:3) as an eluent to give the thiazole 6g, as a solid; FAB-MS m/z 701 (MH)$^+$.

STEP h

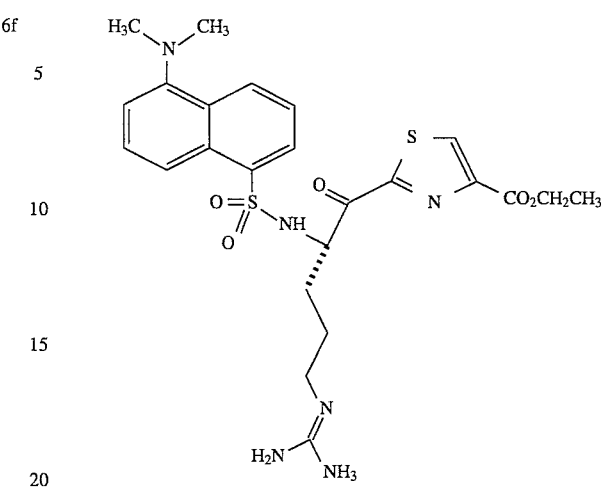

Compound 6

A solution of thiazole 6g (141 mg, 0.20 mmol) and anisole was placed in an HF apparatus reaction vessel under anhydrous conditions and cooled to −78° C. Anhydrous HF (4.5–6.0 mL) was distilled into the vessel and the reaction mixture was allowed to warm to 5° C. and stirred at 5° C. for 3.5 h. The HF was removed in vacuo and the residue was triturated with several portions of ether to give a solid. This solid was purified by reverse-phase HPLC eluting with H$_2$O/CH$_3$CN/TFA (30:20:0.2) to give an oil. This oil was dissolved in distilled water an neutralized to pH 6.20 by the addition of Amberlite® IRA 400 (OH$^-$) resin. The solution was filtered and lyophilized to give compound 6 as a solid; mp 90°–98° C.; FAB-MS m/z 547 (MH)$^+$.

EXAMPLE 7

STEP a

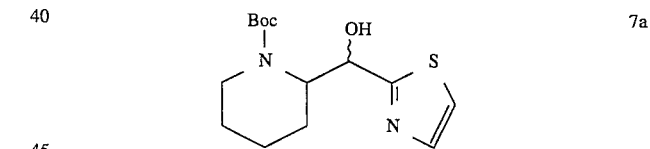

(±)-N-tert-Butoxycarbonyl-2-piperdinecarboxaldehyde (2.13 g, 10.0 mmol; Hassner, et al. *Journal Of Organic Chemistry* 1991, 56, 2775) was added to 2-(trimethylsilyl)thiazole (2.03 g, 11.0 mmol) at room temperature under argon. The reaction mixture was stirred for 6 h, then diluted with anhydrous THF (100 mL) and 5 mL of 1.0M tetrabutylammonium fluoride/THF, stirred for another 40 min and concentrated in vacuo. The residue was dissolved in ethyl acetate and washed with saturated aqueous NaHCO$_3$, dried (Na$_2$SO$_4$) and concentrated in vacuo to give thiazole 7a, as a solid; FAB-MS m/z 299 (MH)$^+$.

STEP b

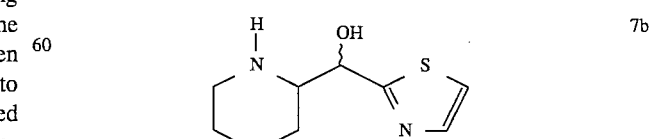

A solution of thiazole 7a (3.22 g, 9.0 mmol), CH$_2$Cl$_2$ (100 mL) and TFA (20 mL) was stirred under argon at room temperature for 3 h and concentrated in vacuo. The residue was partitioned between CHCl₃ (100 mL) and 50% aqueous NaOH (20 mL), then stirred under argon at room temperature. Another portion of CHCl₃ (100 mL) was added and the mixture was stirred yet again. The organic layer was removed and the resulting aqueous layer was washed with several portions of CHCl₃. The combined organic washings were dried (K₂CO₃) and concentrated in vacuo. The residue was purified by chromatography on silica gel, eluting with EtOAc/MeOH/NH₄OH (97:3:1) to give the piperidine derivatives 7b, as separated diastereomers.

STEP c    7c

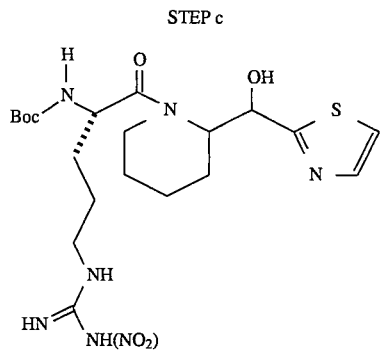

N-Methylmorpholine (0.48 g, 4.68 mmol) was added to a mixture of N-α-Boc-N$^G$-nitro-L-arginine·⅔ Et₂O·¼ EtOAc and anhydrous THF (20 mL) at −20° C. Isobutylchloroformate was added dropwise to this mixture at −15° to −20° C. the resulting mixture was stirred for 35 min. A solution of the piperidine derivative 7b (0.85 g, 4.2 mmol) and anhydrous THF (30 mL) was added under argon at −20° C. This mixture was stirred at −15° C. for 45 min, allowed to warm to room temperature over 3 h and placed in the refrigerator at 0° C. for 16 h. The reaction mixture was filtered and the filtrate was concentrated in vacuo. The residue was dissolved in CHCl₃ and the organic layer was washed with successive portions of saturated aqueous NaHCO₃ and brine, dried (Na₂SO₄) and concentrated in vacuo to give the arginine derivative 7c as a solid; FAB-MS m/z 500 (MH)⁺.

STEP d    7d

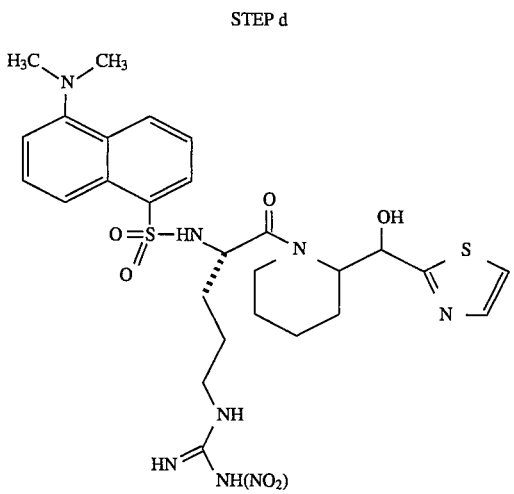

6N HCl/EtOH (40 mL) was added under argon to a solution of arginine derivative 7c (1.75 g, 3.5 mmol) and anhydrous THF (30 mL) at room temperature. The reaction mixture was stirred for 1 h and another portion of 6N HCl/EtOH (10 mL) was added followed by additional stirring (2 h). Yet another portion of 6N HCl/EtOH (10 mL) was added, followed by another hour of stirring. The reaction mixture was concentrated in vacuo and triturated with THF to give a solid. A portion of this solid (1.26 g, 2.30 mmol) stirred with anhydrous THF (45 mL), and triethylamine (0.75 mL). Dansyl chloride (0.63 g, 2.33 mmol) added and the reaction mixture was stirred for 3 h at room temperature. Another portion of triethylamine (0.25 g) and dansyl chloride (0.20 g) was added followed by another hour of stirring at room temperature. The reaction mixture was filtered, concentrated in vacuo and triturated with several portions of ether to give a solid. This solid was purified by column chromatography on silica gel eluting with EtOAc/MeOH/NH₄OH (96:3:1) to give 7d as a solid; FAB-MS m/z 633 (MH)⁺.

STEP e

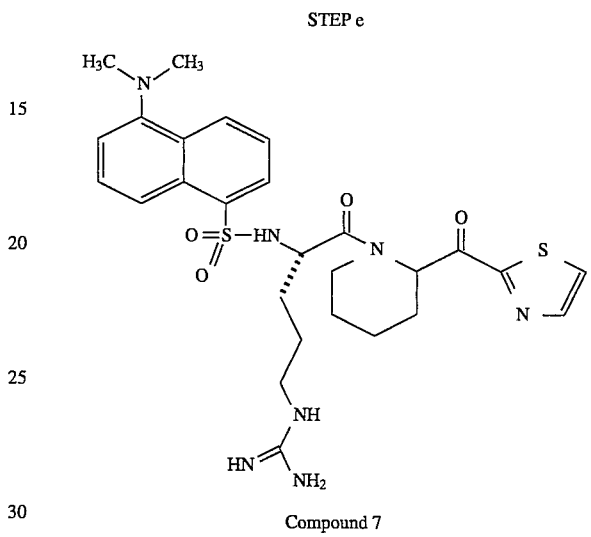

Compound 7

The Dess-Martin periodinane was added to a stirred solution of derivative 7d (0.19 g, 0.30 mmol) and CH₂Cl₂ (10 mL) at room temperature under argon. The reaction mixture was stirred for 1.5 h and treated with 30 mL of quench solution (25 g Na₂S₂O₃ in 100 mL saturated aqueous NaHCO₃). The resulting organic layer was washed with brine, dried (Na₂SO₄) and concentrated in vacuo. The residue was placed in the reaction vessel of an HF apparatus with anisole and cooled to −78° C. HF was distilled into the reaction vessel and the temperature of the vessel was allowed to rise to 5° C. and was maintained there for 40 min. The mixture was concentrated in vacuo and triturated with ether to give a tacky solid. The solid was purified by reverse-phase HPLC using H₂O/CH₃CN/TFA (60:40:0.2) to give compound 7 as a mixture of diastereomers; mp 85°–100° C.; [α]$_D^{25}$ +60.4 (c 0.95, CH₃OH); FAB-MS m/z 586 (MH)⁺.

Anal. Calc'd for C₂₇H₃₅N₇O₄S₂·C₂HF₃O₂·0.2 H₂O: Calculated: C, 44.44; H, 4.53; N, 11.52; H₂O, 1.05. Found: C, 44.36; H, 4.44; N, 11.54; H₂O, 0.92.

EXAMPLE 8

STEP a    8a

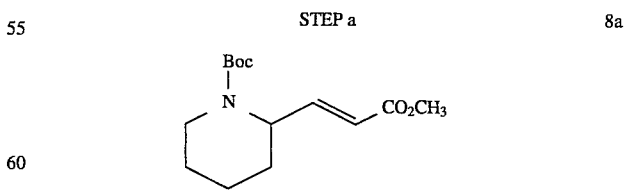

Methyl (triphenylphosphoranylidiene)acetate (4.89 g, 114.6 mmol) was added portionwise to a solution of (±)-N-(tert-butoxycarbonyl)piperdine-2-carboxaldehyde (3.12 g, 14.6 mmol) and anhydrous THF (30 mL) at room temperature under argon. The reaction mixture was stirred at room temperature for 16 h and concentrated in vacuo. The residue was treated with ether (25 mL) and the resulting precipitate was removed by filtration. The filtrate concentrated in vacuo and the residue was purified by chromatography on silica gel using hexane/ether (4:1) as an eluent to give the the ester derivative 8a, as an oil.

STEP b  8b

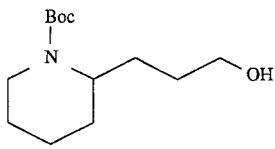

Lithium chloride (1.04 g, 24.5 mmol) was added to a solution of ester 8a (2.20 g, 8.2 mmol) and anhydrous THF (24 mL). Sodium borohydride (0.93 g, 24.5 mmol) was added to this mixture, followed by absolute ethanol (29 mL) and the resulting mixture was stirred at room temperature for 48 h. The mixture was cooled to 0° C. and 10% aqueous citric acid was added to bring the pH to 4. The resulting mixture was concentrated in vacuo, dissolved in $H_2O$ (40 mL) and adjusted with 10% aqueous citric acid to pH 4. The aqueous layer was extracted with several portions of $CH_2Cl_2$ and the combined organic extracts were washed with brine, dried ($Na_2SO_4$) and concentrated in vacuo to give the alcohol derivative 8b as an oil: GC/MS (EI) m/z 227 (M)$^+$.

STEP c  8c

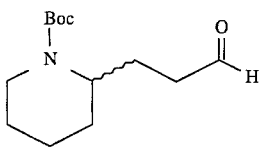

A solution of alcohol 8b (2.06 g, 8.2 mmol) and $CH_2Cl_2$ (20 mL) was added over 2 min to a mixture of pyridinium chlorochromate (2.64 g, 12.3 mmol) and $CH_2Cl_2$ at room temperature. The mixture was stirred for 30 min, ether (200 mL) was added and the resulting solid precipitate was filtered off. This solid was washed with several portions of ether/$CH_2Cl_2$ (2:1) and the combined filtrate and organic washings were combined and filtered through silica gel. The organic solution was dried ($Na_2SO_4$) and concentrated in vacuo to give the aldehyde derivative 8c as an oil.

STEP d  8d

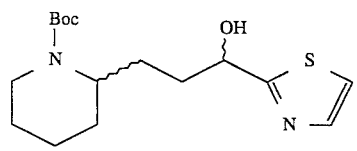

2-Trimethylsilylthiazole (1.63 g, 8.8 mmol) was added to aldehyde 8c (1.93 g, 8.0 mmol) under argon at room temperature. The resulting reaction mixture was stirred for 3.25 h, diluted with anhydrous THF and 1.0M tetrabutylammonium fluoride/THF (4.0 mL), stirred for 30 min and concentrated in vacuo. The residue was dissolved in ethyl acetate, washed with saturated aqueous $NaHCO_3$, dried ($Na_2SO_4$) and concentrated in vacuo to give the thiazole derivative 8d as an oil.

STEP e  8e

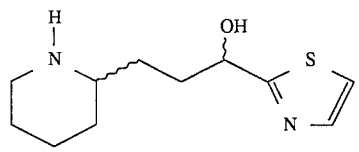

Trifluoroacetic acid (16 mL) was added to a solution of thiazole derivative 8d (2.48 g, 7.6 mmol) and $CH_2Cl_2$ (50 mL) at room temperature under argon. The reaction mixture was stirred for 2 h, concentrated in vacuo and dissolved in $CHCl_3$ (60 mL). This solution was basified with 50% aqueous NaOH (20 mL) and the aqueous layer was washed with several portions of $CHCl_3$/2-propanol (20:1). The combined organic extracts were dried ($K_2CO_3$) and concentrated in vacuo to give an oil. This oil was purified chromatography on silica gel eluting with ethyl acetate/MeOH/$NH_4OH$ (97:3:1 to 90:7:3) to give the deprotected thiazole 8e; FAB-MS m/z 227 (MH)$^+$.

STEP f  8f

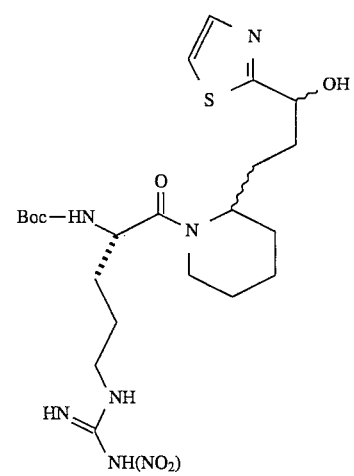

Isobutylchloroformate (0.39 g, 2.87 mmol) was added dropwise to a solution of N-α-Boc-N$^G$-nitro-L-arginine·⅔ $Et_2O$·¼ EtOAc (1.12 g, 2.87 mmol), N-methylmorpholine (0.32 g, 3.20 mmol) and anhydrous THF (20 mL) at −20° C. under argon. The reaction mixture was stirred stirred at −5° to −10° C. for 30 min and cooled to −20° C. A solution of thiazole derivative 8e (0.65 g, 2.87 mmol) and THF (20 mL) was added dropwise over 2–3 min and the resulting mixture was stirred at −15° to −10° C. for 45 min and stirred at room temperature for 16 h. Another potion of N-α-Boc-N$^G$-nitro-L-arginine·⅔ $Et_2O$·¼ EtOAc (0.56 g, 1.44 mmol), N' methylmorpholine (0.16 g, 1.6 mmol) and isobutylchloroformate (0.195 g, 1.44 mmol) was prepared as above and stirred at −15° to −10° C. for 1 h and added to the initial reaction mixture. The resulting mixture was stirred at −15° to −10° C. for 1 h and at room temperature for 16 h. The reaction mixture was filtered and concentrated in vacuo and dissolved in $CHCl_3$. The organic solution was washed with successive potions of saturated aqueous $NaHCO_3$ and brine, dried ($Na_2SO_4$) and concentrated in vacuo. The residue was purified by HPLC eluting with ethyl acetate/MeOH/$NH_4OH$ (30:3:1) to give the arginine derivative 8f as a solid.

STEP g

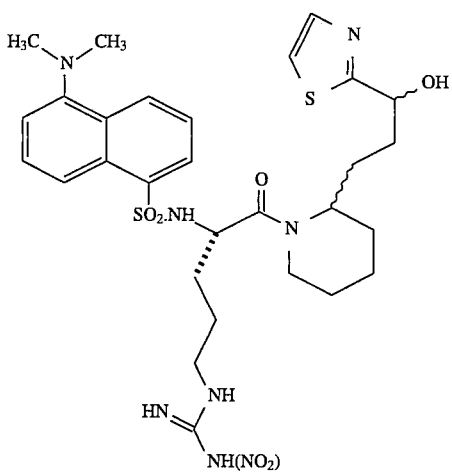

8g

Ethanolic 6N HCl (20 mL) was added slowly to a stirred solution of arginine derivative 8f (0.87 g, 1.65 mmol) and anhydrous THF (15 mL) at room temperature under argon. The reaction mixture was stirred for 45 min, concentrated in vacuo and dissolved in THF (20 mL). Triethylamine (0.75 g, 7.4 mmol) was added followed by dansyl chloride (0.46 g, 1.70 mmol) and the resulting mixture was 'stirred at room temperature under argon for 18 h. Another portion of triethylamine (0.50 g, 4.9 mmol) followed by dansyl chloride (0.23 g, 8.5 mmol) was added and the resulting mixture was stirred for 24 h. The mixture was filtered and the filtrate was concentrated in vacuo and triturated with several portions of ether to give the dansyl derivative 8g as a solid which was used without further purification; FAB-MS m/z 661 (MH)$^+$.

STEP h

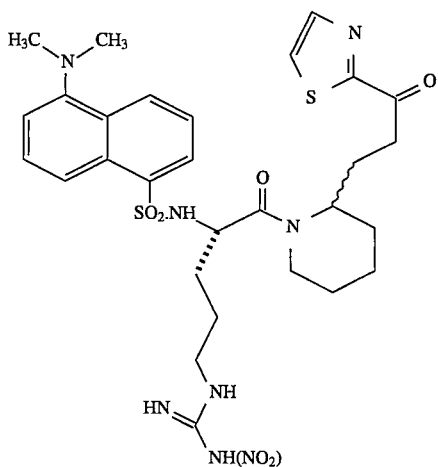

8h

Dess-Martin periodinane (0.72 g, 1.70 mmol) was added portionwise to a stirred mixture of dansyl derivative 8f (1.20 g, 1.36 mmol) and anhydrous CH$_2$Cl$_2$ (40 mL) at 5° C. under argon. The reaction mixture was allowed to warm up to room temperature, stirred for 1.5 h, treated with 100 mL of quench solution (25 g Na$_2$S$_2$O$_3$ in 100 mL saturated aqueous NaHCO$_3$) and extracted with CHCl$_3$ (50 mL) and the resulting aqueous layer was washed with several portions of CHCl$_3$. The combined organic extracts were washed with brine, dried (Na$_2$SO$_4$) and concentrated in vacuo. The residue was purified by chromatography (silica gel) eluting with ethyl acetate/MeOH/NH$_4$OH (95:5:1). The desired fractions were concentrated in vacuo, dissolved in CH$_2$Cl$_2$, dried (Na$_2$SO$_4$) and concentrated in vacuo to give the ketone derivative 8h as a solid; FAB-MS m/z 882 (MH)$^+$.

STEP i

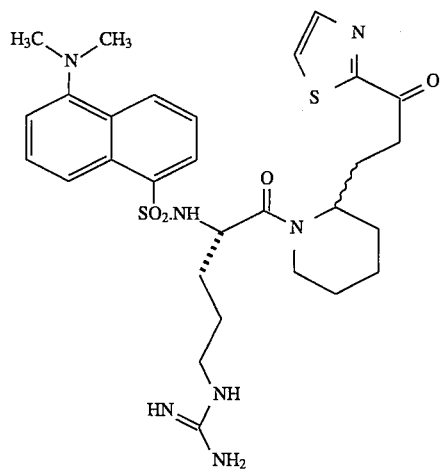

Compound 8

Ketone derivative 8h (160 mg, 0.2 mmol) was placed the reaction vessel of an HF apparatus, anhydrous anisole (2 mL) was added and the mixture was cooled to −78° C. HF (5 mL) was distilled into the vessel and the reaction mixture was allowed to warm up to 0° C. After 1 h, the HF was removed in vacuo, ether (25 mL) was added to the residue and the mixture was stored in the refrigerator at 0° C. under argon for 16 h. The ether was removed and the solid residue was triturated with several portions of ether, isolated and dried in vacuo. The residue was purified by column chromatography (reverse-phase) eluting with CH$_3$CN/H$_2$O/TFA (93:7:0.2) to give compound 8 as a 1:1 mixture of diastereomers: mp 65°–70° C.; $[\alpha]_D^{25}$ +35.6 (c 0.52, MeOH); FAB-MS m/z 614 (MH)$^+$.
Anal. Calc'd for C$_{29}$H$_{39}$N$_7$O$_4$S$_2$·3.5C$_2$HF$_3$O$_2$·0.5 H$_2$O: Calculated: C, 42.71; H, 4.29; N, 9.59; H$_2$O, 0.88. Found: C, 42.76; H, 4.44; N, 9.67; H$_2$O, 0.81.

EXAMPLE 9

STEP a

9a

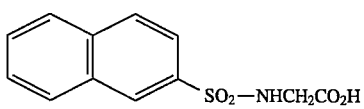

A solution of 2-napthalenesulfonyl chloride (4.52 g, 20 mmol) and ether (50 mL) was added to a stirred solution of glycine (1.5 g, 20 mmol) and 1N NaOH (40 mL) at room temperature. This mixture was stirred for 6 h, the ether layer was separated and the aqueous layer was washed with several portions of ether. The aqueous layer was adjusted to pH 1 with 1N HCl and diluted with H$_2$O (50 mL). The resulting solid precipitate was isolated by filtration and dried in vacuo to give the acid 9a as a solid.

STEP b 9b

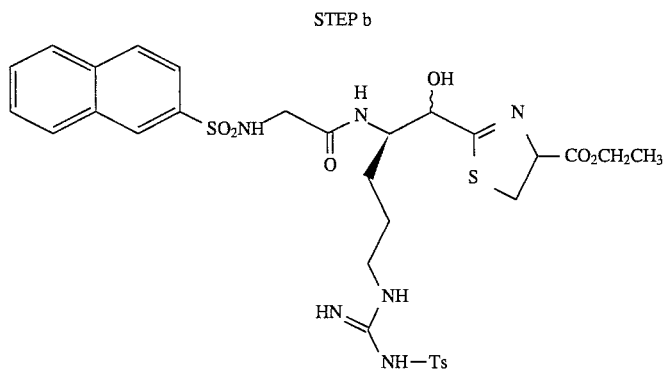

15

A solution of DOG (0.55 g, 2.67 mmol) and CH₃CN (10 mL) was added dropwise to a solution of 1-hydroxybenzotriazole hydrate (0.49 g, 3.64 mmol), the D-arginine epimer of amine 6e (1.43 g, 2.43 mmol), acid 9a (0.64 g, 2.43 mmol) and CH₃CN (20 mL) under argon. The mixture was stirred at room temperature for 2 h, filtered and concentrated in vacuo. The residue was dissolved in water, washed with successive portions of saturated aqueous NaHCO₃ and brine, dried (Na₂SO₄) and concentrated in vacuo. This residue was purified by chromatography eluting with ethyl acetate/MeOH/NH₄OH (95:5:1) as an eluent. The desired fractions were combined, dried (Na₂SO₄) and concentrated in vacuo to give the coupled intermediate 9b as a mixture of diastereomers; FAB-MS m/z 719 (MH)⁺.

was purified by chromatography on silica gel eluting ethyl acetate/MeOH (95:5) as an eluent. The desired fractions were combined, dissolved in CH₂Cl₂, dried (Na₂SO₄) and concentrated in vacuo to give the thiazole derivative 9c as a mixture of diastereomers; FAB-MS m/z 717 (MH)⁺.

STEP c 9c

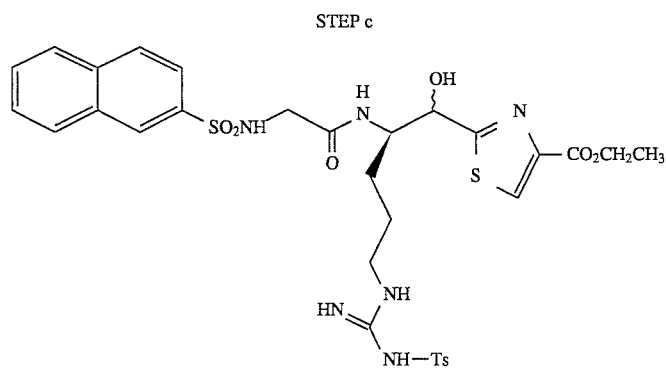

45

Activated MnO₂ (0.90 g, 10.4 mmol) was added to a stirred solution of intermediate 9b (0.85 g, 1.18 mmol) and CH₂Cl₂ (35 mL) at room temperature. The reaction mixture was stirred at room temperature for 48 h, filtered through a Nylon 66 Filter (0.45 μm) and concentrated in vacuo. The residue STEP d 9d

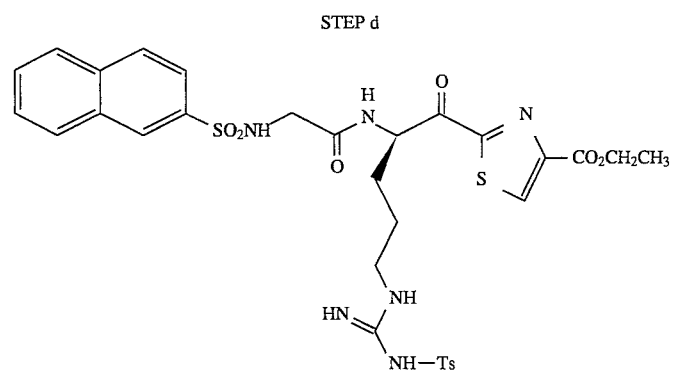

Dess Martin periodinane (105 mg, 0.248 mmol) was added to a stirred solution of thiazole 9c (160 mg, 0.0246 mmol) and CH₂Cl₂ (5 mL) at room temperature. The reaction mixture was stirred for 1 h at room temperature. The reaction mixture was quenched by adding 5 mL of quench solution (25 g $Na_2S_2O_3$ in 100 mL saturated aqueous $NaHCO_3$), ethyl acetate (20 mL) followed by stirring for 40 min. The resulting organic layer was separated and the aqueous layer was washed with portions ethyl acetate. The combined organic extracts were washed with successive portions of saturated aqueous $NaHCO_3$ and brine, dried ($Na_2SO_4$) and concentrated in Vacuo to give ketone 9d as a mixture of diastereomers; FAB-MS m/z 715 $(MH)^+$.

STEP e

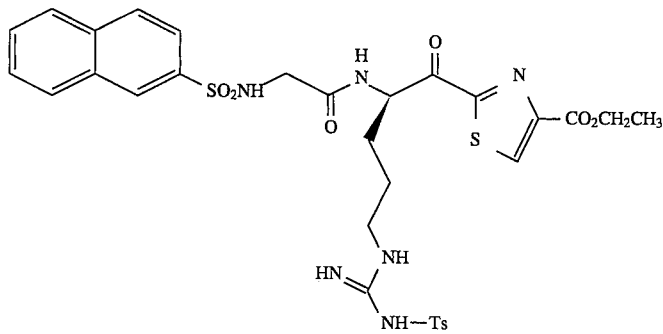

Compound 9

Ketone 9d (190 mg, 0.26 mmol) and anisole (2 mL) were combined in a Teflon reaction tube and placed on an HF apparatus. HF (10 mL) was distilled into the flask at −78° C., the resulting mixture was warmed to 0° C. and stirred at 0° C. for 3h. The HF was removed in vacuo, ether (25 mL) was added and the stoppered flask was placed in the refrigerator for 16 h. The resulting solid precipitate was isolated by filtration, washed with several portions of ether and dried under a stream of nitrogen. This solid was purified by reverse-phase HPLC eluting with $H_2O/CH_3CN/TFA$ (60:40:0.2) to give a solid. This solid was lyophilized to give compound 9 as a solid: mp 105°–110° C.;

Anal. Calc'd for $C_{24}H_{28}N_6O_6S_2 \cdot C_2HF_3O_2 \cdot H_2O$: Calculated: C, 45.08 H, 4.51; N, 12.13; $H_2O$, 2.60. Found: C, 44.96; H, 4.26; N, 11.97; $H_2O$, 2.99.

EXAMPLE 10

STEP a     10a

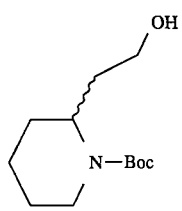

A solution of di-tert-butyl dicarbonate (21.8 g, 0.10 mol) and anhydrous $CH_2Cl_2$ (200 ml) was added dropwise to a stirred solution of (±)-2-piperidineethanol (12.9 g, 0.10 mol) and $CH_2Cl_2$ (200 mL) at 0° C. under argon over 30 min. The reaction was allowed to warm up to room temperature and stirred for 5h. The reaction mixture was extracted with twice with 1N HCl, once with saturated aqueous $NaHCO_3$, and once with brine, dried ($Na_2SO_4$) and concentrated in vacuo to give the protected amine 10a as an oil.

STEP b     10b

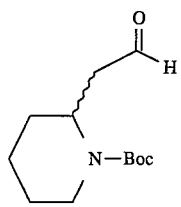

A solution of amine 10a (10.3 g, 45 mmol) and $CH_2Cl_2$ (100 mL) was added over 15 min to a stirred solution of pyridinium chlorochromate (14.5 g, 67.5 mmol) at room temperature. The resulting mixture was stirred for 4 h and diluted with ether (600 mL). The entire reaction mixture was filtered through filter aid and concentrated in vacuo to give the aldehyde 10b as an oil.

STEP c     10c

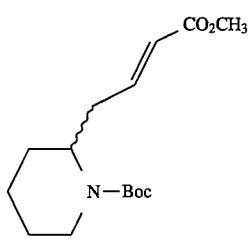

Methyltriphenylphosphoranylidene)acetate (13.46 g, 40.3 mmol) was added in portions to a solution of aldehyde 10b (9.14 g, 40.3 mmol) and THF (100 mL) at room temperature under argon. The reaction mixture was stirred for 16 h and concentrated in vacuo. The residue was triturated with several portions of ether. The combined ethereal extracts were dried ($Na_2SO_4$) and concentrated in vacuo to give the ester 10c as an oil.

STEP d 10d

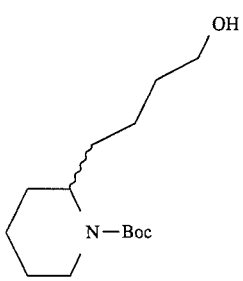

A solution of ester 10c (7.75 g, 27.3 mmol) and LiCl (3.49 g, 82 mmol) in anhydrous THF (80 mL) was treated with NaBH$_4$ (3.12 g, 82 mmol) while stirring at room temperature under argon. EtOH (97 mL) was added and the resulting mixture was stirred at room temperature for 62 h. The resulting mixture was cooled to 0° C. and adjusted to pH 4 with 10% aqueous citric acid. This mixture was concentrated in vacuo to afford an aqueous layer. This layer was readjusted to pH 4 with 10% citric acid, stirred at room temperature for 30 min, and extracted with CH$_2$Cl$_2$ several times. The combined organic extracts were washed with brine, dried and concentrated in vacuo to give the alcohol 10d as an oil.

STEP e 10e

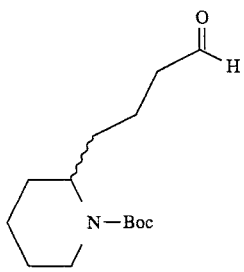

A solution of the alcohol 10d (6.06 g, 23.5 mmol) and CH$_2$Cl$_2$ (50 mL) was added to a mixture pyridinium chlorochromate (7.60 g, 35.3 mmol) and CH$_2$Cl$_2$ (150 mL) over 10 min and the resulting mixture was stirred at room temperature for 2 h. Diethyl ether (250 mL) was added and the resulting mixture was filtered through a plug of silica gel, which in turn was washed with CH$_2$Cl$_2$/Et$_2$O (1:1). The filtrate was dried (Na$_2$SO$_4$) and concentrated in vacuo and the residue was purified by column chromatography on silica gel eluting with ethyl acetate/hexane to give the aldehyde 10e as an oil.

STEP f 10f

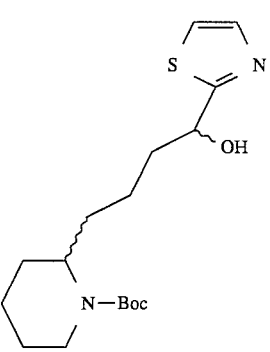

2-(Trimethylsilyl)thiazole (1.70 g, 9.2 mmol) was added to aldehyde 10e (2.07 g, 8.1 mmol) at room temperature under argon. The reaction mixture was stirred for 4 h, diluted with THF (60 mL), and 1.0M tetrabutylammonium fluoride/THF followed by another 15 min of stirring. The resulting mixture was concentrated in vacuo, diluted with ethyl acetate, washed with several successive portions of saturated aqueous NaHCO$_3$ and brine, dried (Na$_2$SO$_4$) and concentrated in vacuo to give the thiazole derivative 10f as an oil.

STEP g 10g

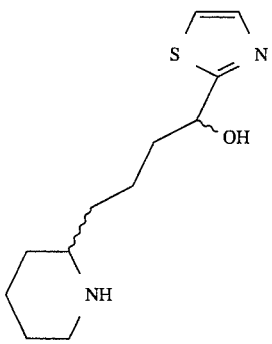

Trifluoroacetic acid (16 mL) was added to a stirred solution of thiazole 10f (2.90 g, 8.0 mmol) and CH$_2$Cl$_2$ (90 mL) at room temperature under argon. The mixture was stirred for 1 h, concentrated in vacuo, and diluted with CH$_2$Cl$_2$ (150 mL). The resulting mixture was neutralized (K$_2$CO$_3$), filtered and concentrated in vacuo. The residue was purified by chromatography uon silica gel eluting with ethyl acetate/ MeOH/NH$_4$OH (95:5:2). The desired fractions were concentrated in vacuo, dissolved in CH$_2$Cl$_2$, dried (K$_2$CO$_3$) and concentrated in vacuo to give the amine 10g as a mixture of diastereomers

STEP g 10g

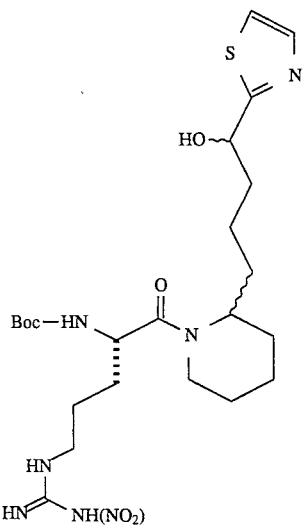

Isobutyl chloroformate (0.55 g, 4.0 mmol) was added to a stirred mixture of N-α-Boc-N$^G$-nitro-L-arginine·⅔ Et$_2$O·¼ EtOAc (1.56 g, 4.0 mmol), 4-methylmorpholine (0.44 g, 4.4 mmol) and anhydrous THF (25 mL) at −20° to −15° C. under argon and the reaction temperature was maintained at −15° to −10° C. for 1.5 h. A solution of amine 10f (0.85 g, 3.54 mmol) and THF (5 mL) was added over 60 seconds at −10° C. The reaction mixture was stirred at −10° C. for 1 h, allowed to warm up to room temperature, and stirred for 16 h. A drop of DMF was added, the resulting mixture was stirred for another 2 h at room temperature and was filtered. The filtrate was concentrated in vacuo and dissolved in CHCl$_3$. The organic layer was washed with successive portions of saturated aqueous NaHCO$_3$ and brine, dried (Na$_2$SO$_4$) and concentrated in vacuo to give the coupled derivative 10g as a solid.

STEP h          10h

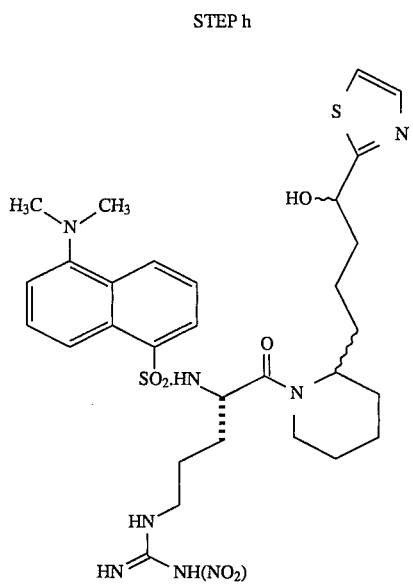

Ethanolic 6N HCl was added to a solution of derivative 10g (1.60 g, 2.95 mmol) and THF (30 mL) at room temperature under argon. The resulting mixture was stirred for 2.5 h, concentrated in vacuo, dissolved in THF (25 mL) and concentrated once again to give an oil. The residue was dissolved in THF (40 mL) along with triethylamine (15 mmol) and treated with dansyl chloride (0.84 g, 3.1 mmol). This mixture was stirred at room temperature under argon for 16 h. The resulting mixture was filtered, the filtrate was concentrated in vacuo and the residue was triturated twice with ether to give the dansyl derivative 10 h as a white solid which used in the next step without purification.

STEP i          10i

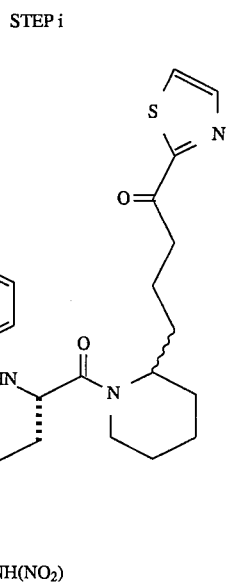

Dess-Martin periodinane (0.90 g, 2.1 mmol) was added to a stirred solution of derivative 10h (1.02 g, 1.5 mmol) and CH$_2$Cl$_2$ (30 mL) at room temperature under argon. The mixture was stirred for 1.5 h at room temperature, treated with 50 mL of quench solution (25 g Na$_2$S$_2$O$_3$ in 100 mL saturated aqueous NaHCO$_3$), and stirred for 40 min. The organic layer was separated and the aqueous layer was extracted twice with CH$_2$Cl$_2$. The combined CH$_2$Cl$_2$ extracts were washed with brine, dried (Na$_2$SO$_4$) and concentrated in vacuo. The residue was dissolved in ethyl acetate (10 mL) and MeOH (3 ml), purified by chromatography on silica gel eluting with ethyl acetate/MeOH/NH$_4$OH (95:5:1). The desired fractions were combined dissolved in CH$_2$Cl$_2$, dried (Na$_2$SO$_4$) and concentrated in vacuo to give the ketone 10i as a solid.

STEP f

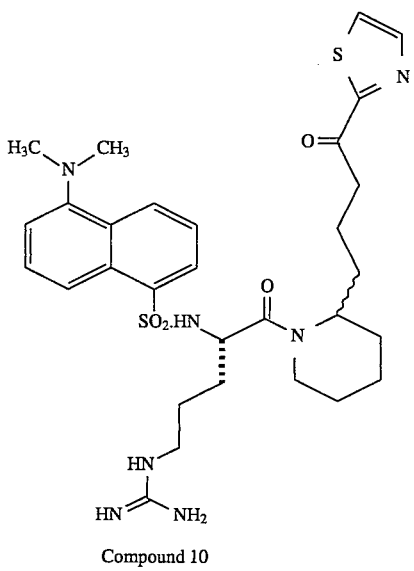

Compound 10

The ketone 10i (0.32 g, 0.47 mmol) and anisole (5 mL) were placed in a Teflon reaction tube of an HF apparatus under anhydrous conditions and cooled to −78° C. HF (20 mL) was distilled directly into this flask and the temperature of the mixture was allowed to rise to 0° C. This mixture was stirred for 1 h, the HF was removed in vacuo and the residue was dissolved in ether (25 mL) and stored in the refrigerator under anhydrous conditions overnight. The ether layer was removed and the resulting residue was triturated with several portions of ether to give a solid. This solid was purified by reverse-phase HPLC using H$_2$O/CH$_3$CN/TFA (60:40:0.2) to give the compound 10 as a mixture of diastereomers: mp 81°–91° C.; [α]$_D^{25}$ +25.9 (c 0.26, MeOH); FAB-MS m/z 628.9 (MH)$^+$.

Anal. Calc'd for C$_{30}$H$_{41}$N$_7$O$_4$S$_2$·3C$_2$HF$_3$O$_2$·H$_2$O: Calculated: C, 43.77; H, 4.69; N, 9.92; H$_2$O, 1.82. Found: C, 43.77; H, 4.56; N, 10.00; H$_2$O, 1.82.

EXAMPLE 11

N-METHYL-D-PHENYLALANYL-N-[5-[(AMINOIMINOMETHYL)AMINO]-1S-[(BENXOTHIAZOL-2-YL)CARBONYL]PENTYL]-L-PROLINAMIDE

STEP a    11a

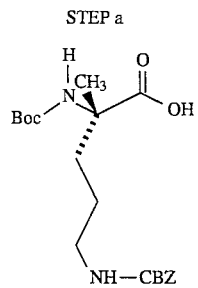

A suspension of L-C$^\alpha$-methylornithine·2HCl (7.03 g, 35 mmol; Zhenping, Z.; Edwards, P.; Roeske, R. W. *Int. J. Peptide Protein Res.* 1992, 40, 119–126) in 60 mL of water was cooled to 5° C. and the pH was adjusted to 11.0 with 3N NaOH. Benzyl chloroformate (6.00 mL, 42 mmol) was added dropwise over 4 h while stirring under argon at 5° C. The reaction was allowed to slowly warm to 22° C. over 16 h and then extracted three times with ether. The aqueous layer was cooled to 5° C., adjusted to pH 2.0 with 3N HCl, and extracted with three portions of ethyl acetate. The cold acidic aqueous layer was readjusted to pH 11.0 with 3N NaOH and diluted with 175 mL of dioxane. Di-tert-butyl dicarbonate (38.2 g, 175 mmol) was added in one portion at 5° C. while stirring under argon. The reaction was allowed to slowly warm to 22° C. over 16 h, the pH was adjusted to 11.0 with 3N NaOH, and another portion of di-tert-butyl dicarbonate (38.2 g, 175 mmol) was added and stirred at 22° C. over 24 h. The dioxane was removed in vacuo at 40° C. and the reaction mixture was adjusted to pH 11 with 3N NaOH, extracted three times with ether, cooled to 5° C., and saturated with NaCl. Ethyl acetate (100 mL) was added and the aqueous layer was adjusted to pH 4.0 with 25% aqueous citric acid (CAUTION: evolution of $CO_2$) while stirring at 5° C. The layers were separated and the acidic aqueous layer was extracted five more portions of ethyl acetate. The combined ethyl acetate extracts were dried (Mg $SO_4$), filtered through Celatom FW-14 and concentrated in vacuo at 40° C. to give 3.70 g (56%) of 11a as a clear glass; FAB-MS m/z 381 (MH)$^+$.

STEP b    11b

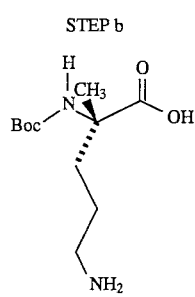

Compound 11a (6.86 g, 18 mmol) was dissolved in 180 mL of methanol and combined with 1.37 g of 20%Pd(OH)$_2$/C and placed under 60 psig of $H_2$ on a Parr hydrogenation apparatus for 18 h. The reaction was filtered and the filter cake was extracted with four 150 mL portions of hot methanol (CAUTION). The combined methanol extracts were filtered through Celatom FW-14 and concentrated in vacuo at 40° C. to give 3.50 g (79%) of compound 11b as a white solid; FAB-MS m/z 247 (MH)$^+$.

STEP c    11c

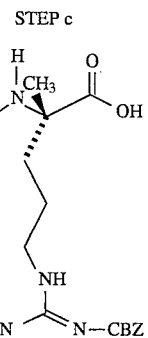

Compound 11b (3.40 g, 13.8 mmol) was combined with triethylamine (5.77 mL, 41.4 mmol) in DMF (75 mL) and to the resulting suspension was added N,N'-bis(benzyloxycarbonyl)-S-methylisothiourea (7.42 g, 20.7 mmol; ibid.). The resulting mixture was stirred at 22° C. under a nitrogen atmosphere for 40 h, treated with triethylamine (2.0 mL, 14.4 mmol) and N,N'-bis(benzyloxycarbonyl)-S-methylisothiourea (0.78 g, 2.2 mmol), stirred for 24 h, treated again with triethylamine (2.0 mL, 14.4 mmol) and N,N'-bis(benzyloxycarbonyl)-S-methylisothiourea (1.48 g, 4.1 mmol), and stirred at 22° C. for 3 days. The crude reaction mixture was filtered through Celatom FW-14 and the DMF was removed in vacuo at 40° C. The oily residue was partitioned between 200 mL of 0.1N NaOH and 200 mL of ether. The basic aqueous layer was extracted four times with ether, cooled to 5° C., layered with ethyl acetate, and adjusted to pH 3.5 with citric acid. The layers were separated and the acidic aqueous layer was extracted four times with ethyl acetate. The combined ethyl acetate extracts were dried (Na$_2$SO$_4$), filtered through Celatom FW-14, and concentrated in vacuo at 40° C. The residue was purified by HPLC on silica gel eluting with CH$_2$Cl$_2$/MeOH (95:5) to give 5.94 g (77%) of 11c as a white foam; FAB-MS m/z 557 (MH)$^+$.

STEP d    11d

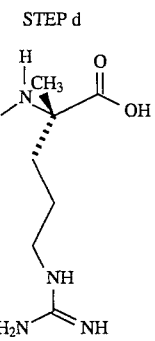

To a solution of compound 11c (5.86 g, 10.5 mmol) in 210 mL of methanol was added 20% Pd(OH)$_2$/C (1.47 g) and the mixture was placed under 60 psig of hydrogen on a Parr hydrogenation apparatus. After 24 h, another portion of 20% Pd(OH)$_2$/C (0.74 g) was added and the reaction was placed under 60 psig of hydrogen for 6 h. The crude reaction mixture was filtered through Celatom FW-14 and concentrated in vacuo to afford 3.03 g (100%) of 11d as a white foam; FAB-MS m/z 289 (MH)$^+$.

STEP e    11e

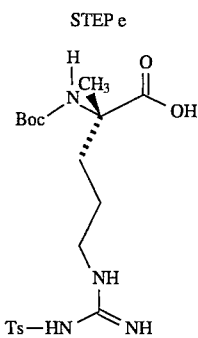

Compound 11d (519 mg, 1.80 mmol) was dissolved in 2.7 mL of 4N KOH and diluted with 9.0 mL of acetone and cooled to −18° C. To this solution was added a solution of p-toluenesulfonyl chloride (686 mg, 3.6 mmol) in 3.6 mL of acetone over 15 min while stirring vigorously. After 1 h at −18° to −15° C., the reaction was allowed to slowly warm to 22° C. over 2.5 h. The acetone was removed in vacuo at 20° C. and the aqueous residue was diluted 25 mL of water and extracted three times with ether. The aqueous layer was saturated with NaCl, layered with ethyl acetate, cooled to 5° C. and adjusted to pH 3.5 with 1N HCl. The acidic aqueous layer was extracted four more times with ethyl acetate and the combined ethyl acetate extracts were washed twice with brine, dried ($Na_4SO_4$), and concentrated in vacuo to give 720 mg (90%) of 11e as a white foam; FAB-MS m/z 443 $(MH)^+$.

STEP f    11f

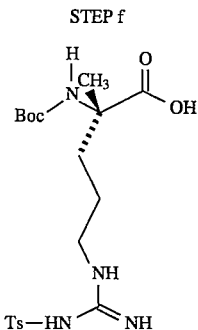

A stirring solution of 11e in 29 mL of $CH_2Cl_2$/MeOH (9:1) was cooled to 5° C. and treated dropwise over 10 min with 2M (trimethylsilyl)diazomethane in hexanes (4.3 mL, 8.63 mmol). After 10 min, the reaction was concentrated in vacuo at 22° C. and the residue was purified by HPLC on silica gel eluting with ethyl acetate/hexane (3:2) to give 1.06 g g (81%) of 11f as a white foam; FAB-MS m/z 457 $(MH)^+$.

STEP g    11g

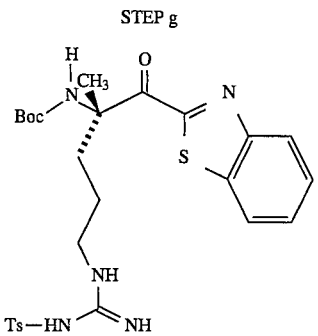

A solution of benzothiazole (2.63 g, 19.5 mmol) in 20 mL of THF was cooled to −75° C. while stirring under nitrogen. n-Butyl lithium (1.6M in hexanes, 9.46 mL, 15.1 mmol) was added dropwise over 15 min at −75° to −65° C. and then stirred at −75° to −65° C. for 15 min. To this solution was added dropwise over 15 min a solution of 11f (461 mg, 1.0 mmol) in 10 mL of THF at −75° to −70° C. The reaction was stirred at −75° C. for 2 h, quenched with 160 mL of saturated aqueous $NH_4Cl$, saturated with NaCl, and extracted three times with ethyl acetate. The combined ethyl acetate extracts were washed three times with brine, dried ($Na_2SO_4$), and concentrated in vacuo. The residue was triturated three times with hexane, dissolved in 150 mL of ethyl acetate/hexane (3:2), filtered through Celatom FW-14, and purified by HPLC on silica gel eluting with ethyl acetate/hexane (3:2) to give 0.42 g (74%) of 11g as clear glass; FAB-MS m/z 560 $(MH)^+$.

STEP h    11h

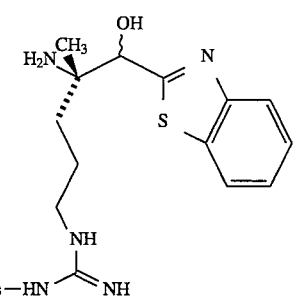

Compound 11g (0.389 g, 693 mmol) was dissolved in 14 mL of $CF_3CO_2H/CH_2Cl_2$ (1:4), stirred at 22° C. for 2 h under a nitrogen atmosphere, and concentrated in vacuo at 10° C. The residue was partitioned between 20 mL of aqueous 1N NaOH previously saturated with NaCl and 20 mL of $CH_2Cl_2$. The basic aqueous layer was extracted three more times with $CH_2Cl_2$ and the combined $CH_2Cl_2$ extracts were washed with brine, dried ($Na_2SO_4$), and concentrated in vacuo to give 319 mg (100%) of 11h as a brown amorphous solid; FAB-MS m/z 462 $(MH)^+$.

STEP i    11i

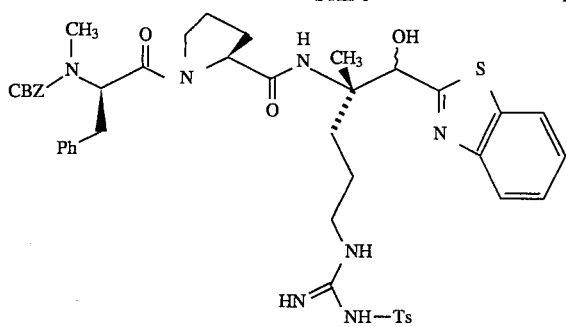

A solution of (CBZ)-N-methyl-D-phenylalanyl-L-proline (0.309 g, 0.753 mmol; U.S. Pat. No. 4,703,036) and diisopropylethylamine (132 µl, 0.758 mmol) in 10 mL of anhydrous $CH_2Cl_2$ was cooled to 5° C. while stirring under an argon atmosphere. Bis(2-oxo-3-oxazolidinyl)phosphinic chloride (BOP-Cl; 0.193 g, 0.758 mmol) was added and the reaction was stirred for 15 min. A solution of 10h (0.316 g, 0.685 mmol) and diisopropylethylamine (119 µl, 0.684 mmol) in 10 mL of anhydrous $CH_2Cl_2$ was over 10 min added at 5° C. and the reaction was allowed to warm to 22° C. over 4.5 h. The reaction was concentrated in vacuo at 40° C. and the residue was partitioned between ethyl acetate and aqueous 1M $KHSO_4$. The organic layer was extracted two more times with aqueous 1M $KHSO_4$, three times with saturated aqueous $NaHCO_3$, twice with brine, dried ($Na_2SO_4$) and concentrated in vacuo at 40° C. The residue was purified by chromatography on silica gel eluting with ethyl acetate/hexane (4:1) to give 0.381 g (65%) of 11i as a white foam; FAB-MS m/z 855 (MH)+.

STEP j    11j

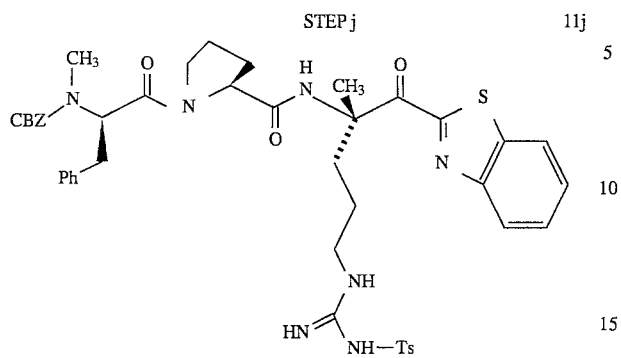

Compound 11i (0.359 g, 0.420 mmol) was dissolved in 6 mL of anhydrous $CH_2CL_2$. The Dess-Martin periodinane (0.304 g, 0.717 mmol) was added and the reaction was stirred under argon at 22° C. for 3 h. The excess periodinane was consumed by the addition of 20 mL of quench solution (25 g $Na_2S_2O_3$ in 100 mL saturated aqueous $NaHCO_3$) diluted with ethyl acetate (60 mL), and stirred at room temperature for 15 min. The resulting aqueous layer was isolated and extracted with several portions of ethyl acetate and the combined organic extracts were washed with successive portions of water and brine, dried ($Na_2SO_4$) and concentrated in vacuo to give 0.336 g (94%) of ketone 11j, as a white foam; FAB-MS m/z 853 (MH)+.

STEP k

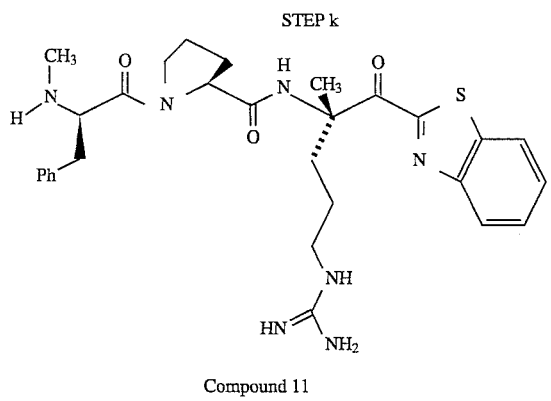

Compound 11

Compound 11j (0.336 g, 0.394 mmol) was dissolved in 3 mL of anhydrous thioanisole, placed in a Teflon reaction tube of an HF apparatus under anhydrous conditions, and cooled to −78° C. Anhydrous HF (3–4 mL) was distilled into this tube and upon completion of addition, the temperature of the mixture was allowed to rise to 0° C. This mixture was stirred at 0° C. for 4 h, concentrated in vacuo, and triturated with several portions of ether to give a white solid. This solid was purified by reverse phase HPLC eluting with $H_2O$/acetonitrile/TFA (60:40:0.2). The fractions containing compound 10 were combined, concentrated in vacuo, and lyophilized to afford 0.094 g (28%) of compound 11 as a white solid; mp 122°–130° C.; $[\alpha]_D^{25}$ −85.3 (c 0.26, MeOH); FAB-MS m/z 853 (MH)+.
Anal. for $C_{29}H_{37}N_7O_3S \cdot 2.3TFA \cdot 1.9 H_2O$: Calculated: C, 46.92; H, 5.05; N, 11.40; F, 15.24; $H_2O$, 3.98 Found: C, 46.59; H, 5.00; N, 11.17; F, 15.16; $H_2O$, 3.40.

EXAMPLE 12

N-METHYL-D-PHENYLALANYL-N-[4-
[(AMINOIMINOMETHYL)AMINO]-
2S-[(6-METHOXYCARBONYLBENXOTHIAZOL-
2-YL)CARBONYL]BUTYL]-L-PROLINAMIDE
Cpd#12

STEP a    12a

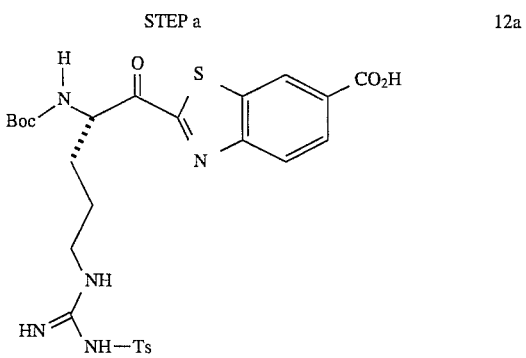

1.6M n-Butyl lithium (80.3 mL, 128.4 mmol) was added dropwise to a stirred solution of benzothiazole-6-carboxylic acid (11.5 g, 64.17 mmol) in THF (100 mL) at −78° C. under nitrogen at a rate that kept the reaction temperature below −70° C. Upon completion of addition, the reaction mixture was stirred for 30 min at −78° C. and a solution of N-α-Boc-$N^G$-tosyl-L-arginine N,O-dimethyl amide (800 mg, 1.69 mmol; DiMaio, et al. *Journal of Medicinal Chemistry* 1992, 35, 3331) (2.52 g, 5.35 mmol) in THF (150 mL) was added at a rate that maintained the reaction temperature below 70° C. The resulting mixture was stirred for 2 h at −78° C., warmed to −20° C., and diluted with saturated aqueous $NH_4Cl$ (700 mL). The resulting organic layer was separated and the aqueous layer was washed with several portions of EtOAc. The combined organic extracts were washed with water, brine, dried ($Na_2SO_4$) and concentrated in vacuo. The crude mixture was purified by chromatography on silica gel eluting with $CH_2Cl_2$/MeOH (8:1) to give the coupled benzothiazole derivative, 12a as a solid.

STEP b    12b

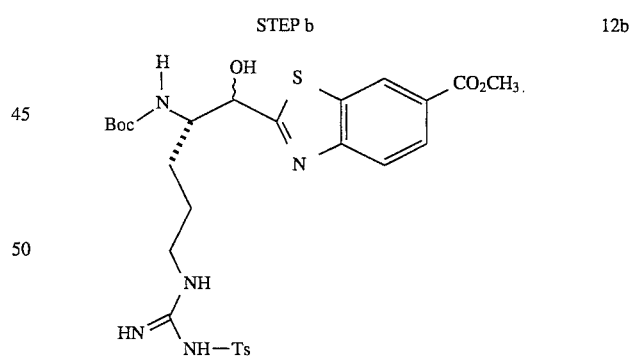

Sodium borohydride (1.42 g, 37.6 mmol) was added in one portion to a solution of 12a (3.5 g, 5.9 mmol) in MeOH (130 mL) at −25° to −20° C. and the reaction was stirred for 40 min. Acetone (20 mL) was added, the mixture was allowed to warm up to room temperature and concentrated in vacuo. The residue was dissolved in water, acidified with acetic acid (pH 3–4) and extracted with several portions of EtOAc. The combined extracts were washed with water and brine, dried ($Na_2SO_4$) and concentrated in vacuo. The residue was dissolved in $CH_2Cl_2$/MeOH (6:1) and cooled to 0° C. Trimethylsilyldiazomethane (2M in hexanes) was added dropwise over 5 min until a yellow color persisted and the reaction was stirred for another 25 min. The resulting STEP c

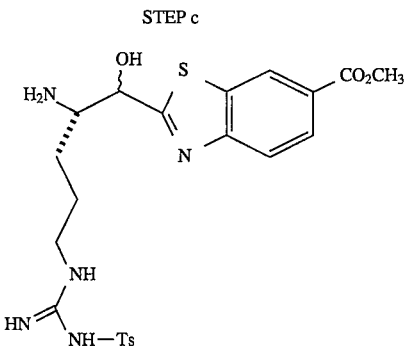

12c

A solution of compound 12b (3.1 g, 4.56 mmol, TFA (26 mL) in CH$_2$Cl$_2$ (104 mL) was stirred at room temperature for 1 h and concentrated in vacuo. The residue diluted with CH$_2$Cl$_2$ and concentrated under high vacuum to give the crude product 12c as an oil.

STEP d

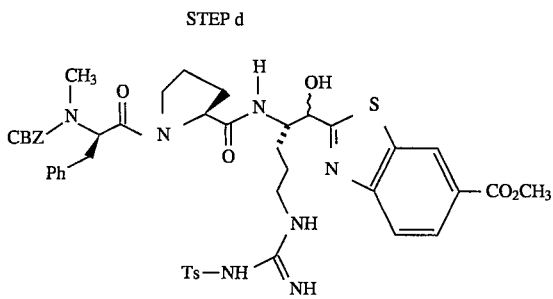

12d

A solution of 12c (2.3 g, 4.56 mmol) and HOBT (1.32 g, 9.12 mmol) in CH$_3$CN (210 mL) was neutralized by the addition of triethylamine (approx. 5 mL) under N$_2$. DCC (1.41 g, 6.84 mmol) and N-methyl-N-CBZ-D-phenylalanine-L-proline was added to this solution in one portion and this mixture was stirred for 2 h at room temperature and filtered. The filtrate was concentrated in vacuo and dissolved in EtOAc. The organic solution was washed with saturated aqueous NaHCO$_3$, water and brine, dried (Na$_2$SO$_4$) and concentrated in vacuo to give the coupled product 12d as a solid.

STEP e

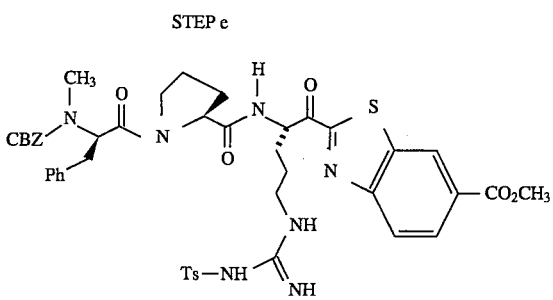

12e

Dess-Martin periodinane (680 mg, 1.60 mmol) was added to a solution of 12d (720 mg, 3.76 mmol) in CH$_2$Cl$_2$ (40 mL) at room temperature under an atmosphere of N$_2$ and the resulting mixture was stirred for 25 min. The excess periodinane was consumed by the addition of 30 mL of quench solution (25 g Na$_2$S$_2$O$_3$ in 100 mL saturated aqueous NaHCO$_3$) to the stirred reaction mixture. The resulting aqueous layer was isolated and extracted with several portions of CH$_2$Cl$_2$ and the combined organic extracts were washed with successive portions of water and brine, dried (Na$_2$SO$_4$) and concentrated in vacuo to give the ketone 12e, as a solid.

STEP f

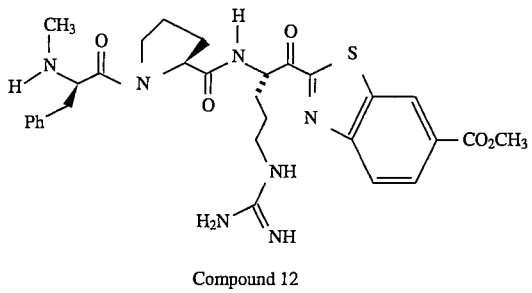

Compound 12

The intermediate ketone 12e (730 mg, 0.81 mmol) and anisole (3 mL) were placed in a Teflon reaction tube of an HF apparatus under anhydrous conditions and cooled to −78° C. HF (15–20 mL) was distilled into this tube and upon completion of addition, the temperature of the mixture was allowed to rise to 0° C. This mixture was stirred for 3.5 h, concentrated in vacuo and triturated with several portions of ether to give a solid. This solid was purified by reverse-phase, HPLC using water/acetonitrile/TFA (70:30:0.2) to give compound 12 as a solid: mp 125° C.; $[\alpha]_D^{25}$ −82.6 (c 0.5, MeOH); FAB-MS m/z 608.3 (MH$^+$).

Anal. Calc'd for C$_{30}$H$_{37}$N$_7$O$_5$S·2.5 CF$_3$CO$_2$H·1.7 H$_2$O: Calculated: C, 45.53; H, 4.68; F, 15.43; N, 10.62; H$_2$O, 3.32 Found: C, 45.51; H, 4.53; F, 15.19; N, 10.54, H$_2$O, 3.32.

EXAMPLE 13

N-METHYL-D-PHENYLALANYL-N-[4-[(AMINOIMINOMETHYL)AMINO]-1S-[(6-CARBOXYBENXOTHIAZOL-2-YL)CARBONYL]BUTYL]-L-PROLINAMIDE

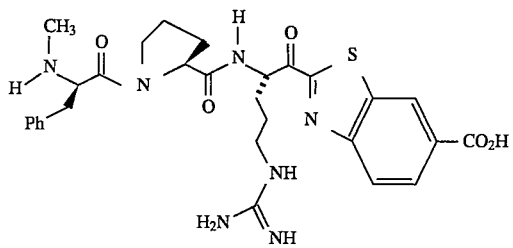

Compound 13

Compound 13 was prepared by modifying Example 12. A solution of anhydrous LiOH (400 mg, 16.7 mmol) in water (12 mL) was added to a stirred solution of compound 12d (5.0 g, 5.57 mmol) in dioxane (100 mL) at room temperature. The mixture was stirred for 4 h and an additional potion of LiOH (300 mg, 12.5 mmol) in water (7 mL) was added, followed by another 3 hours of stirring. The resulting mixture was acidified with HOAc (pH 3–4) and extracted several times with EtOAc. The combined organic extracts were washed with water and brine, dried (Na$_2$SO$_4$) and concentrated to give the 6 carboxybenzothiazole derivative. This derivative converted to the desired compound by following step e (quenching with 25% aqueous Na$_2$S$_2$O$_3$) and step f of Example 12 to give compound 13 as a solid; mp 125° C.; $[\alpha]_D^{25}$ −79.6 (c 1.0, MeOH); FAB-MS m/z 594.4 (MH$^+$).

Anal. Calc'd for C$_{29}$H$_{35}$N$_7$O$_5$S·2.5 CF$_3$CO$_2$H·H$_2$O: Calculated: C, 45.54; H, 4.44; F, 15.89; N, 10.93; H$_2$O, 2.01

Found: C, 45.59; H, 4.59; F, 15.60; N, 10.76; H₂O, 2.09.

EXAMPLE 14

N-METHYL-D-PHENYLALANYL-N-[4-[(AMINOIMINOMETHYL)AMINO]-1S-[(6-CARBOXAMIDOBENXOTHIAZOL-2-YL)CARBONYL]BUTYL]-L-PROLINAMIDE

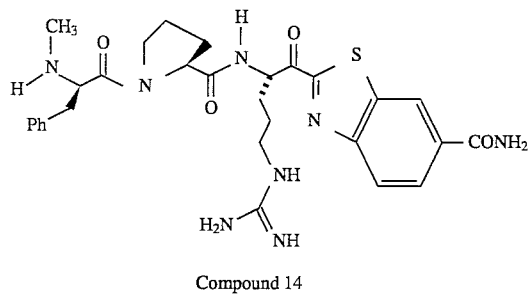

Compound 14

Compound 14 was prepared by modifying Example 12. HOBT (138 mg, 0.102 mmol) and DCC (14 mg, 0.068, mmol) was added to a stirred solution of compound 12c (30 mg, 0.034 mmol) in CH₂Cl₂/DMF (4:1, 2 mL) at room temperature under N₂. The reaction mixture was stirred for 30 min and aqueous 29% NH₄OH (50 μL, 0.38 mmol) was added. The mixture was stirred for 5 h and another portion of HOBT (7 mg), DCC (7 mg), and aqueous 29% NH₄OH (20 μL) was added. After another 2 h of stirring, the mixture was diluted with CH₂Cl₂. The resulting organic layer was washed with successive portions of water and brine, dried (Na₂SO₄) and concentrated to give the corresponding 6-carboxamidobenzothiazole derivative. This derivative was converted to the desired compound by following steps e and f of example 12 to give compound 14 as a solid: mp 130°–143° C.; [α]$_D^{25}$ –76.0 (c 0.3, MeOH); FAB-MS m/z 593 (MH⁺).
Anal. Calc'd for C₂₉H₃₆N₈O₄S·2.9 CF₃CO₂H·3.2 H₂O: Calculated: C, 42.61; H, 4.65; F, 16.85; N, 11.42.; H₂O, 5.87. Found: C, 42.16; H, 4.35; F, 16.19; N, 11.45.; H₂O, 5.37

EXAMPLES 15 and 16

N-METHYL-D-PHENYLALANYL-N-[4-[(AMINOIMINOMETHYL)AMINO]-1S-[(6-HYDROXYMETHYLBENXOTHIAZOL-2-YL)CARBONYL]BUTYL]-L-PROLINAMIDE
Cpd#15

N-METHYL-D-PHENYLALANYL-N-[4-[(AMINOIMINOMETHYL)AMINO]-1R-[(6-HYDROXYMETHYLBENXOTHIAZOL-2-YL)CARBONYL]BUTYL]-L-PROLINAMIDE
Cpd#16

STEP a

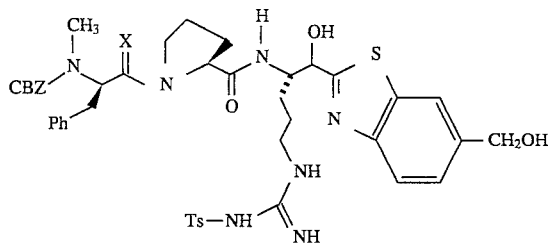

15a; X = O          15e; X = H, H

Compound 15 was prepared by modifying Example 12. 1.0M DIBAL (10 mL, 10 mmol) was added dropwise to a stirred solution of compound 12c (1.5 g, 1.67 mmol) in dry CH₂Cl₂ (160 mL) at –78° C. under N₂. The temperature of the reaction mixture was kept below –74° C. during this addition. The mixture was stirred for 45 min and quenched with concentrated aqueous NH₄OH (50 mL). A portion of 1N HCl was added to aid in the separation of the aqueous and organic layers and the resulting aqueous layer was washed with CH₂Cl₂. The combined organic extracts were washed with successive portions of saturated NaHCO₃, water and brine, dried (Na₂SO₄) and concentrated to give 15a and the corresponding methylene derivative 15e as a mixture which was used without purification.

STEP b

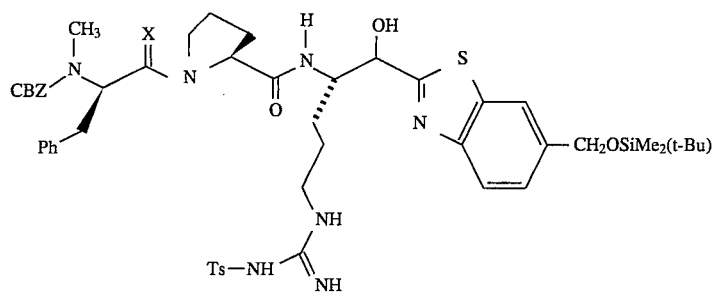

15b; X = O  15f; X = H, H

DMAP (61.2 mg, 0.50 mmol) and triethylamine (140 μL, 1.00 mmol) were added to a stirred solution of 15a and 15e (9.2 mg) at 0° C. under $N_2$. A solution of tert-butyltrimethylsilylchloride (45.3 mg, 0.30 mmol) in $CH_2Cl_2$ (15 mL) was added in one portion and the reaction was allowed to warm up to room temperature and stirred for 8 h. The resulting mixture was diluted with $CH_2Cl_2$ and washed with successive portions of 10% citric acid, saturated aqueous $NaHCO_3$, $H_2O$, and brine. The resulting organic layer was dried ($Na_2SO_4$) and concentrated in vacuo to give a mixture of 15b and the corresponding methylene derivative 15f, which was used without further purification.

STEP c

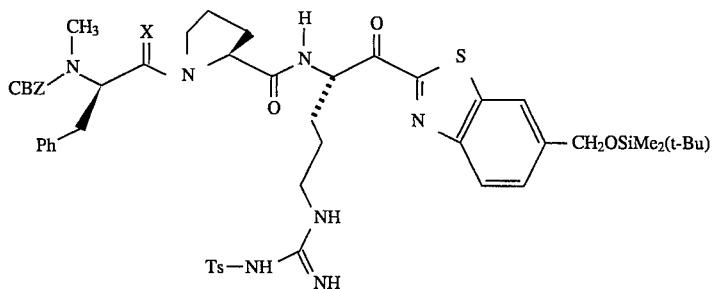

15c; X = O  15g; X = H, H

Dess-Martin periodinane (142 mg, 0.334 mmol) was added to a solution of 15b and 15f (160 mg) in $CH_2Cl_2$ (20 mL) at room temperature under an atmosphere of $N_2$ and the resulting mixture was stirred for 30 min. The excess periodinane was consumed by the addition of 10 mL of quench solution (25 g $Na_2S_2O_3$ in 100 mL saturated aqueous $NaHCO_3$) to the stirred reaction mixture. The resulting aqueous layer was isolated and extracted with several portions of $CH_2Cl_2$ and the combined organic extracts were washed with successive portions of saturated $NaHCO_3$, as well as brine, dried ($Na_2SO_4$) and concentrated in vacuo to give a mixture of ketone 15c and the corresponding methylene derivative 15g as a solid.

STEP d

-continued

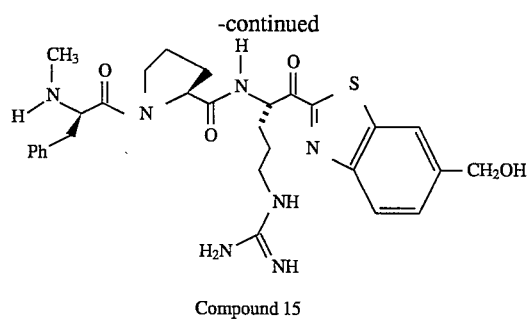

Compound 15

77

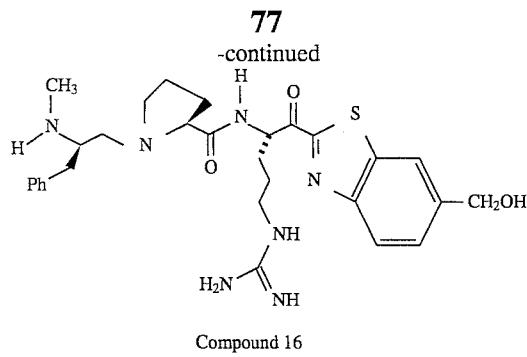

Compound 16

Intermediates and 15c and 15g (170 mg, 0.17 mmol) and anisole (2.5 mL) were placed in a Teflon reaction tube of an HF apparatus under anhydrous conditions and cooled to −78° C. HF (5 mL) was distilled into this tube and upon completion of addition, the temperature of the mixture was allowed to rise to 0° C. This mixture was stirred for 3.5 h, concentrated in vacuo and triturated with several portions of ether to give a solid. This solid was purified by reverse-phase HPLC using water/acetonitrile/TFA (70:30:0.2) to give compounds 15 and 16 as pure solids:
Compound 15: FAB-MS m/z 580 (MH$^+$).
Compound 16: mp 75°–85° C.; $[\alpha]_D^{25}$ =−82.6 (c=0.32, MeOH); FAB-MS m/z 580 (MH$^+$);
Anal. Calc'd for $C_{30}H_{37}N_7O_5S \cdot 2.5\ CF_3CO_2H \cdot 1.7\ H_2O$: Calculated: C, 43.74 H, 4.85; N, 10.09 Found: C, 43.96; H, 4.76; N, 9.95

EXAMPLE 17 and 18

N-METHYL-D-PHENYLALANYL-N-[4-[(AMINOIMINOMETHYL)AMINO]-1S-[(6-FLUOROBENXOTHIAZOL-2-YL)CARBONYL]BUTYL]-L-PROLINAMIDE
Cpd#17

N-METHYL-D-PHENYLALANYL-N-[4-[(AMINOIMINOMETHYL)AMINO]-1S-[(6-FLUOROBENXOTHIAZOL-2-YL)CARBONYL]BUTYL]-L-PROLINAMIDE
Cpd#18

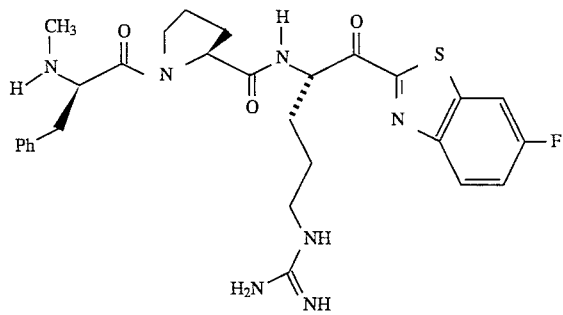

Compound 17

78

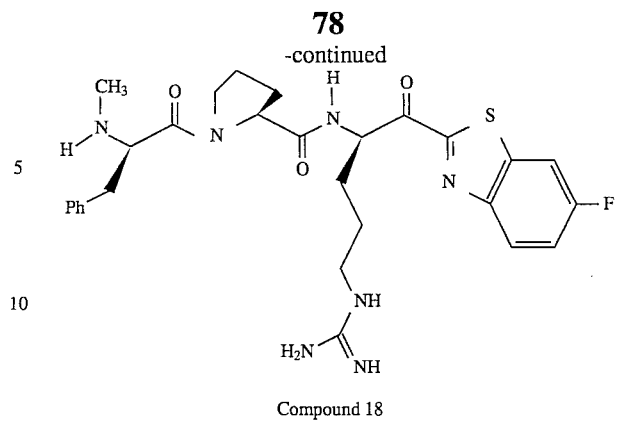

Compound 18

Compounds 17 and 18 were prepared by modifying Example 12. The starting benzothiazole of 12 Step A was replaced with 6-fluorobenzothiazole and the remaining steps of the sequence were carried through with only minor modifications. The preparation of 6-fluorobenzothiazole follows. A solution of sodium nitrite (24.6 g, 35.7 mmol) in water (80 mL) was added dropwise to a stirred solution of 2-amino-6-fluorobenzothiazole (10.0 g, 59.5 mmol) in 85% $H_3PO_4$ at 31 10° C., so that the reaction temperature did not exceed −4° C. This mixture was maintained at −8° C. for 1 h, poured into 50% $H_3PO_4$ at 0° C. and allowed to warm up to room temperature over 2 h. Water was added to give a total volume of 3 L and the resulting mixture was neutralized with $Na_2CO_3$. The aqueous layer and the solid precipitate were extracted with several portions of $CHCl_3$/EtOAc (1:1) and the combined organic extracts were washed with brine, dried ($Na_2SO_4$) and concentrated in vacuo to give 6-fluorobenzothiazole as a solid.

Compound 17: mp 65°–80° C.; $[\alpha]_D^{25}$ =−72.9 (c=0.32, MeOH); FAB-MS m/z 568 (MH$^+$);
Anal. Calc'd for $C_{28}H_{34}FN_7O_3S \cdot 3.0\ CF_3CO_2H \cdot 1.1\ H_2O$: Calculated: C, 43.94; F, 20.44, H, 4.25; N, 10.55; $H_2O$, 2.13 Found: C, 43.96; F, 20.57; H, 4.22; N, 10.82; $H_2O$, 2.22
Compound 18: mp 85°–100° C.; $[\alpha]_D^{25}$=−61.6 (c=0.85, MeOH); FAB-MS m/z 568 (MH$^+$);
Anal. Calc'd for $C_{28}H_{34}FN_7O_3S \cdot 2.7\ CF_3CO_2H \cdot 0.9\ H_2O$: Calculated: C, 44.99; F, 19.39, H, 4.35; N, 10.99; $H_2O$, 1.82 Found: C, 45.01; F, 19.61; H, 4.24; N, 11.15; $H_2O$, 1.84

EXAMPLES 19 and 20

N-METHYL-D-PHENYLALANYL-N-[4-
[(AMINOIMINOMETHYL)AMINO]-
1S-[(4-ETHOXYCARBONYLTHIAZOL-2-
YL)CARBONYL]BUTYL]-L-PROLINAMIDE
Cpd#19

N-METHYL-D-PHENYLALANYL-N-[4-
[(AMINOIMINOMETHYL)AMINO]-
1S-[(4-ETHOXYCARBONYLTHIAZOL-2-
YL)CARBONYL]BUTYL]-L-PROLINAMIDE
Cpd#20

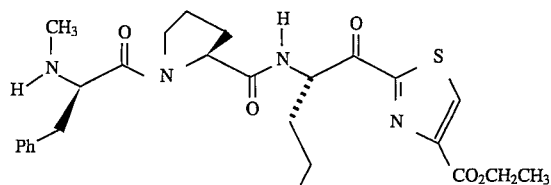

Compound 19

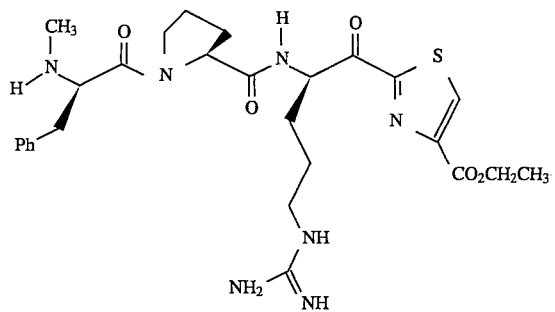

Compound 20

Compounds 19 and 20 were prepared by modifying the method of Example 9. N-CBZ-N-methyl-D-phenylalanyl-L-proline was used in place of intermediate 9a, and the remaining steps of the reaction sequence were carried out on the respective arginine epimers, with only minor modifications to give the title compounds as a solids:

Compound 19: mp 85°–100° C.; $[\alpha]_D^{25}$ =−61.6 (c=0.85, MeOH); FAB-MS m/z 572 (MH$^+$);
Anal. Calc'd for $C_{27}H_{37}N_7O_5S \cdot 2.3\ CF_3CO_2H \cdot 1.5\ H_2O$: Calculated: C, 44.08; H, 4.95; N, 11.39; $H_2O$, 3.14 Found: C, 44.25; H, 4.68; N, 11.29; $H_2O$, 3.29

Compound 20: mp 85°–100° C.; $[\alpha]_D^{25}$ =−61.6 (c=0.85, MeOH); FAB-MS m/z 572 (MH$^+$);
Anal. Calc'd for $C_{27}H_{37}N_7O_5S \cdot 2.75\ CF_3CO_2H \cdot 2.0\ H_2O \cdot 0.2\ C_2H_3N$: Calculated: C, 42.51; H, 4.81; N, 10.85; $H_2O$, 3.88

Found: C, 42.17; H, 4.66; N, 10.88; $H_2O$, 4.21

EXAMPLE 21

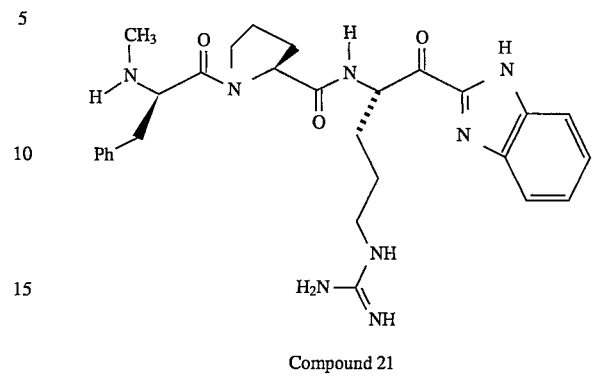

Compound 21

Compound 21 was prepared by modifying the method of of Example 5. 1,2-Phenylenediamine replaced 2-aminophenol in Step d of that example to give the corresponding benzimidazole derivative. This derivative was carried through the remaining steps with minor modifications to give the title compound as a solid: mp 70°–80° C.; $[\alpha]_D^{25}$ =−63.1 (c=1.00, $H_2O$); FAB-MS m/z 533 (MH$^+$);
Anal. Calc'd for $C_{28}H_{36}N_8O_3 \cdot 3.75\ CF_3CO_2H \cdot H_2O$: Calculated: C, 43.59; H, 4.30; N, 11.45; $H_2O$, 1.84 Found: C, 43.66; H, 4.37; N, 11.45; $H_2O$, 1.84

EXAMPLE 22

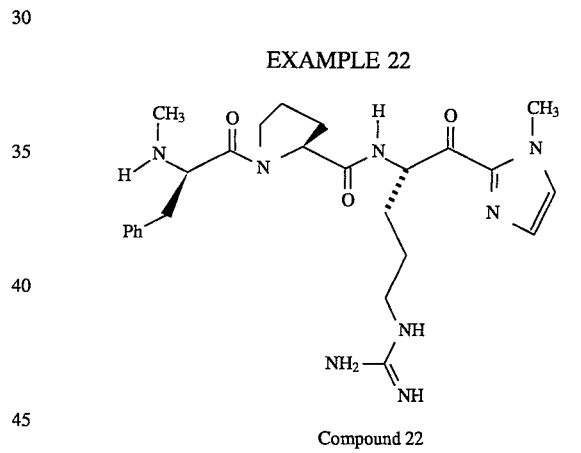

Compound 22

Compound 22 was prepared following the general procedure of Example 12. N-methylimidazole was used in place of benzothiazole in step a, to give the imidazole analog of intermediate 12a. This intermediate was carried through the remaining steps to give compound 22 as a solid: mp 85°–100° C.; $[\alpha]_D^{25}$ =−61.6 (c=0.85, MeOH); FAB-MS m/z 497 (MH$^+$);
Anal. Calc'd for $C_{28}H_{34}FN_7O_3S \cdot 2.7\ CF_3CO_2H \cdot 0.9\ H_2O$: Calculated: C, 44.99; F, 19.39, H, 4.35; N, 10.99; $H_2O$, 1.82 Found: C, 45.01; F, 19.61; H, 4.24; N, 11.15; $H_2O$, 1.84

EXAMPLE 23

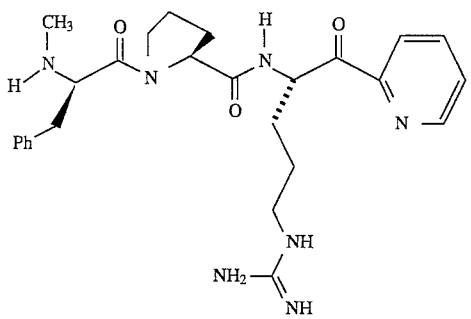

Compound 23

Compound 23 was prepared using the method of Example 12. Benzothiazole-6-carboxylic acid was replaced with 2-bromopyridine to give the title compound as a solid: mp 40°–68° C.; FAB-MS m/z 494 (MH$^+$);

Anal. Calc'd for $C_{28}H_{34}FN_7O_3S\cdot2.7$ $CF_3CO_2H\cdot0.9$ $H_2O$: Calculated: C, 44.99; F, 19.39, H, 4.35; N, 10.99; $H_2O$, 1.82 Found: C, 45.01; F, 19.61; H, 4.24; N, 11.15; $H_2O$, 1.84

EXAMPLE 24

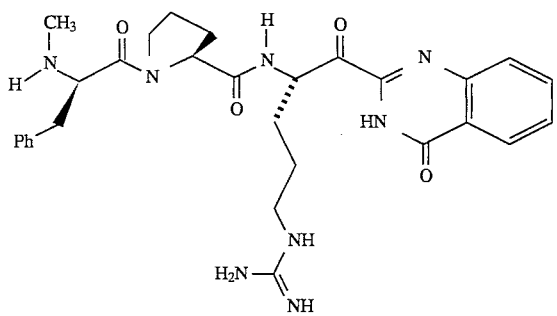

Compound 24

Compound 24 was prepared using the method of Example 5 replacing 2-aminophenol with anthranilic acid to give the title compound as a solid: mp 122°–138° C.; FAB-MS m/z 561 (MH$^+$);

Anal. Calc'd for $C_{29}H_{36}N_8O_4\cdot2.6$ $C_2H_2O_4\cdot3.0$ $H_2O$: Calculated C, 45.08; H, 4.93; N, 12.30; $H_2O$, 5.93 Found: C, 45.05; H, 4.79; N, 12.57; $H_2O$, 5.99

EXAMPLE 25

N-METHYL-D-PHENYLALANYL-N-[4-[(AMINOIMINOMETHYL)AMINO]-1S-[(6-HYDROXYBENXOTHIAZOL-2-YL)CARBONYL]BUTYL]-L-PROLINAMIDE

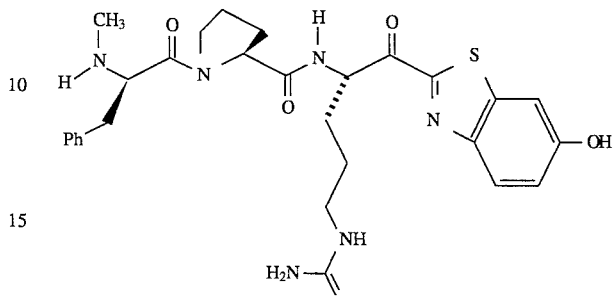

Compound 25

Compound 25 was prepared using the method of Example 12 by replacing benzothiazole-6-carboxylic acid with 5-(tert-butyldiphenylsilyloxy)benzothiazole to give a solid: mp 118°–128° C.; FAB-MS m/z 566 (MH$^+$);

Anal. Calc'd for $C_{28}H_{35}N_7O_4S\cdot2$ $C_2H_2O_4\cdot1.5$ $H_2O$: Calculated C, 46.83; H, 4.79; N, 11.95; $H_2O$, 3.29 Found: C, 46.79; H, 4.79; N, 12.15; $H_2O$, 3.29

EXAMPLE 26

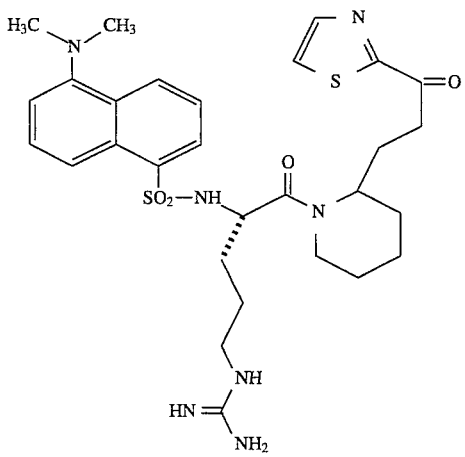

Compound 26

Compound 26 was prepared by further separating the individual diastereomers of compound 8 by reverse-phase HPLC the to give the title compound as a solid: mp 90°–110° C.; FAB-MS m/z 614 (MH+).

EXAMPLE 27

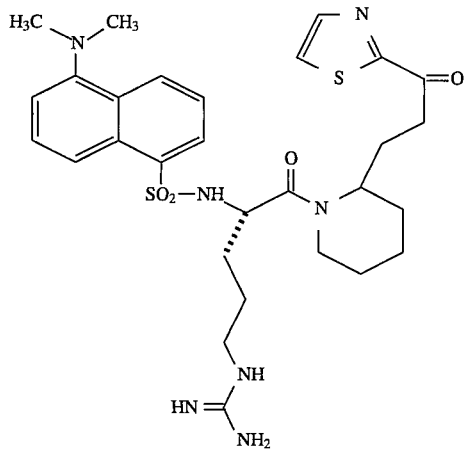

Compound 27

Compound 27 was prepared by further separating the individual diastereomers of compound 8 by reverse-phase HPLC the to give the title compound as a solid: mp 60°–75° C.; FAB-MS m/z614 (MH+).

EXAMPLE 28

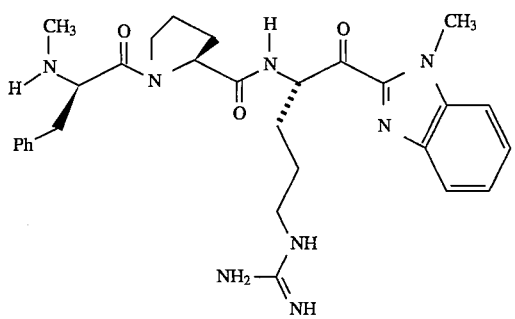

Compound 28

Compound 28 was prepared using the method of Example 12 by replacing benzothiazole-6-carboxylic acid with 1-methylbenzimidazole to give a solid: mp 118°–128° C.; FAB-MS m/z566 (MH+); $[\alpha]_D^{25}$ =−57.8 (c=1.0, MeOH);
Anal. Calc'd for $C_{29}H_{38}N_8O_3 \cdot 3.2\ C_2H_2O_4 \cdot 1.1H_2O$: Calculated C, 45.65; F, 19.58; H, 4.70; N, 12.03; $H_2O$; 2.13
Found: C, 45.66; F, 19.19; H, 4.51; N, 12.02; $H_2O$; 1.77

EXAMPLE 29

N-METHYL-D-CYOLOHEXYLALANYL-N-[4-[(AMINOIMINOMETHYL)AMINO]-1S-[(BENXOTHIAZOL-2-YL)CARBONYL]BUTYL]-L-PROLINAMIDE

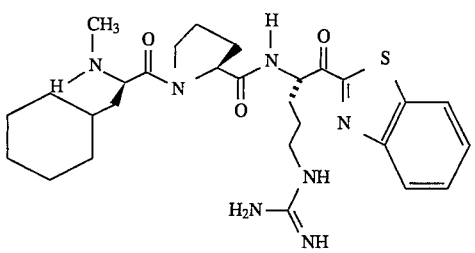

Compound 29

Compound 29 was prepared following the general procedure of Example 12. Benzothiazol-6-carboxylic acid was replaced with benzothiazole in step a and N-CBZ-N-methyl-D-phenylalanyl-L-proline was replaced with N-Boc-N-methyl-D-cyclohexylalanyl-L-proline in step d to give the title compound as a solid: mp 90°–100° C.; $[\alpha]_D^{25}$ =−40.96 (c=0.708, MeOH); FAB-MS m/z 497 (MH+);
Anal. Calc'd for $C_{28}H_{41}\ N_7O_3S \cdot 3\ CF_3CO_2H \cdot 0.75\ H_2O$:
Calculated: C, 44.81; F, 18.76, H, 4.35; N, 10.76; $H_2O$, 1.48
Found: C, 44.92; F, 18.83; H, 5.03; N, 10.80; $H_2O$, 1.37

EXAMPLE 30

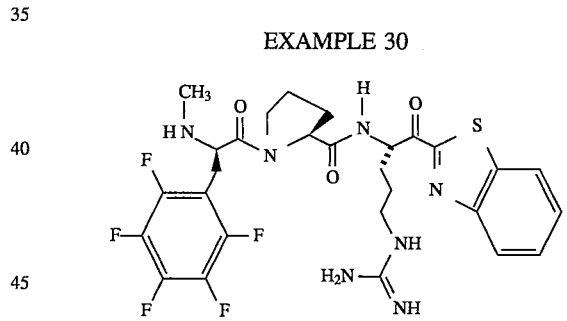

Compound 30

Compound 30 was prepared following the general procedure of Example 12. N-CBZ-N-methyl-D-phenylalanyl-L-proline was replaced with N-Boc-N-methyl-D-(pentafluorophenyl)alanyl-L-proline to give the title compound as a solid: mp 98°–125° C.; FAB-MS m/z 640 (MH+);
Anal. Calc'd for $C_{28}H_{30}F_5N_7O_3S \cdot 2.25\ CF_3CO_2H \cdot 1.25\ H_2O$:
Calculated: C, 42.48; F, 24.29, H, 3.81; N, 10.67; $H_2O$, 2.45
Found: C, 42.75; F, 24.12; H, 3.85; N, 10.66; $H_2O$, 2.61

EXAMPLE 31

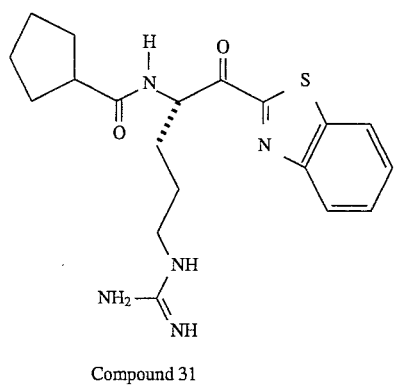

Compound 31

Compound 31 was prepared using the method of Example 12. Benzothiazole-6-carboxylic acid was replaced with benzothiazole and N-CBZ-N-methyl-D-phenylalanyl-L-proline was replaced with cyclopentane carboxylic acid to give the title compound as a solid: mp 60°–70° C.; $[\alpha]_D^{20} = +5.1$ (C=0.68, MeOH); FAB-MS m/z 388 (MH$^+$);
Anal. Calc'd for $C_{19}H_{25}N_5O_2S \cdot 1.25CF_3CO_2H \cdot 0.75 \ H_2O$:
Calculated C, 47.50; F, 13.10; H, 5.14; N, 12.88; H$_2$O, 2.48
Found: C, 47.50; F, 13.19; H, 4.99; N, 13.19; H$_2$O, 2.37

EXAMPLE 32

N-METHYL-D-(4-FLUOROPHENYL)ALANYL-N-[4-[(AMINOIMINOMETHYL)AMINO]-1S-[(BENXOTHIAZOL-2-YL)CARBONYL]BUTYL]-L-PROLINAMIDE

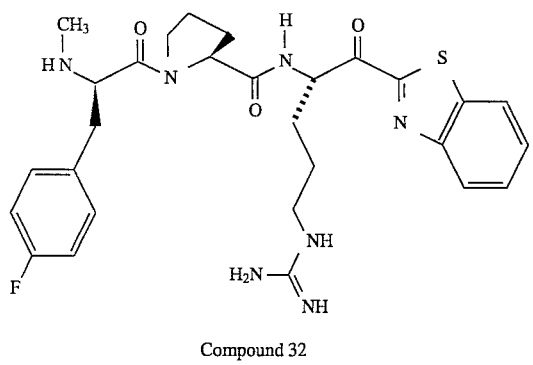

Compound 32

Compound 32 was prepared using the method of Example 12. Benzothiazole-6-carboxylic acid was replaced with benzothiazole and N-CBZ-N-methyl-D-phenylalanyl-L-proline was replaced with N-Boc-N-methyl-D-(4-fluorophenyl)alanyl-L-proline to give the title compound as a solid: mp 70°–125° C.; $[\alpha]_D^{25} = -79.7$ (C=1.0, MeOH); FAB-MS m/z 568 (MH$^+$);
Anal. Calc'd for $C_{28}H_{34}N_7O_3S \cdot 2.1 \ CF_3CO_2H \cdot 1.1 \ H_2O$: Calculated C, 46.77; F, 16.77; H, 4.67; N, 11.86; H$_2$O, 2.40
Found: C, 46.42; F, 16.69; H, 4.67; N, 11.82; H$_2$O, 2.54

EXAMPLES 33 and 34

N-METHYL-D-PHENYLGLYCYL-N-[4-[(AMINOIMINOMETHYL)AMINO]-1S-[(BENXOTHIAZOL-2-YL)CARBONYL]BUTYL]-L-PROLINAMIDE

Cpd#33

Cpd#34

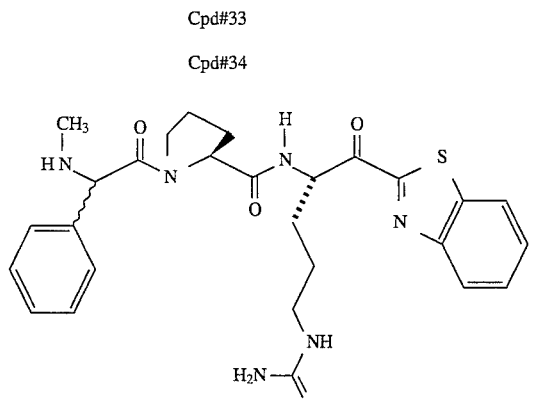

Compounds 33 and 34

Compound 33 was prepared using the method of Example 12. Benzothiazol-6-carboxylic acid was replaced with benzothiazole and N-CBZ-N-methyl-D-phenylalanyl-L-proline was replaced with N-Boc-N-methyl-D,L-phenylglycyl-L-proline to give diastereomers 33 and 34 which were separated by reverse-phase HPLC:
Compound 33; mp 60(s)–125° C.; $[\alpha]_D^{20} = -43.0$ (C=1.0, MeOH); FAB-MS m/z 536 (MH$^+$);
Anal. Calc'd for $C_{27}H_{33}N_7O_3S \cdot 2.1CF_3CO_2H \cdot 1.9 \ H_2O$: Calculated: C, 46.30; F, 14.78; H, 4.84; N, 12.11; H$_2$O, 4.23
Found: C, 46.52; F, 15.09; H, 4.84; N, 12.29; H$_2$O, 4.53
Compound 34: mp 65(s)–125° C.; $[\alpha]_D^{20} = -1.3$ (C=1.0, MeOH); FAB-MS m/z 536 (MH$^+$);
Anal. Calc'd for $C_{27}H_{33}N_7O_3S \cdot 2.25CF_3CO_2H \cdot 1.75H_2O$:
Calculated: C, 45.93; F, 15.57; H, 4.74; N, 11.90; H$_2$O, 3.83
Found: C, 46.21; F, 15.67; H, 4.90; N, 12.09; H$_2$O, 4.22

EXAMPLE 35

N-METHYL-D-(DIPHENYL)ALANYL-N-[4-[(AMINOIMINOMETHYL)AMINO]-1S-[(BENXOTHIAZOL-2-YL)CARBONYL]BUTYL]-L-PROLINAMIDE

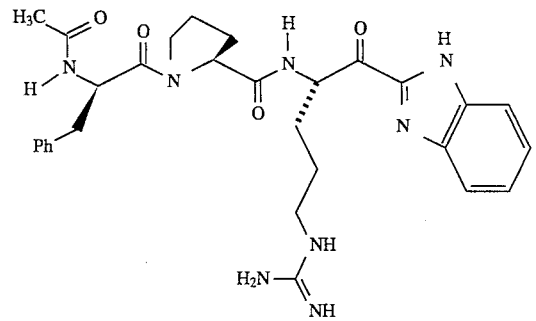

Compound 35

Compound 35 was prepared using the method of Example 12. Benzothiazol-6-carboxylic acid was replaced with benzothiazole and N-CBZ-N-methyl-D-phenylalanyl-L-proline was replaced with N-acetyl-D-phenylalanyl-L-proline to give the title compound as a solid: mp 65°–125° C.; FAB-MS m/z 578 (MH⁺);
Anal. Calc'd for $C_{29}H_{35}N_7O_4S \cdot 1.4\ CF_3CO_2H \cdot H_2O$: Calculated: C, 50.57; F, 10.56; H, 5.12; N, 12.98; $H_2O$, 2.38 Found: C, 50.77; F, 10.39; H, 5.03; N, 13.17; $H_2O$, 2.70

EXAMPLE 36

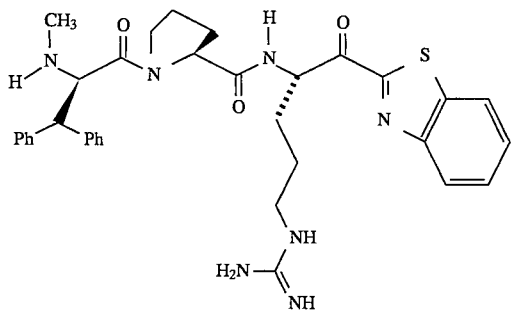

Compound 36

Compound 36 was prepared using the method of Example 12. N-Boc-N-methyl-D-diphenylalanyl-L-proline replaced N-CBZ-N-methyl-D-phenylalanyl-L-proline and benzothiazole replaced benzothiazole-6-carboxylic acid to give the title compound as a solid: mp 65°–125° C.; FAB-MS m/z 578 (MH⁺);
Anal. Calc'd for $C_{29}H_{35}N_7O_3S \cdot 2.25\ CF_3CO_2H \cdot 1.9H_2O$: Calculated: C, 50.45; F, 13.99; H, 4.95; N, 10.69; $H_2O$, 3.73 Found: C, 50.20; F, 10.70; H, 4.78; N, 13.62; $H_2O$, 3.34

EXAMPLE 37

N-METHYL-D-CYCLOHEXYLGLYCYL-N-[4-[(AMINOIMINOMETHYL)AMINO]-1S-[(BENXOTHIAZOL-2-YL)CARBONYL]BUTYL]-L-PROLINAMIDE

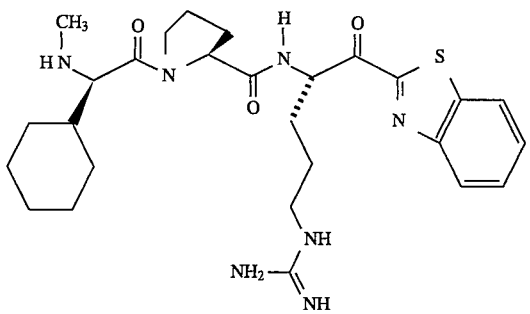

Compound 37

Compound 37 was prepared using the method of Example 12. N-CBZ-N-methyl-D-phenylalanyl-L-proline was replaced with N-Boc-N-methyl-D-cyclohexylglycyl-L-proline and benzothiazole-6-carboxylic acid was replaced with benzothiazole to give the title compound as a solid: mp 65°–125° C.; FAB-MS m/z 542 (MH⁺);
Anal. Calc'd for $C_{27}H_{39}N_7O_3S \cdot 2.0\ CF_3CO_2H \cdot 2.0H_2O$: Calculated: C, 46.21; F, 14.15; H, 5.63; N, 12.17; $H_2O$, 4.47 Found: C, 45.96; F, 14.39; H, 5.71; N, 12.07; $H_2O$, 4.41

EXAMPLE 38

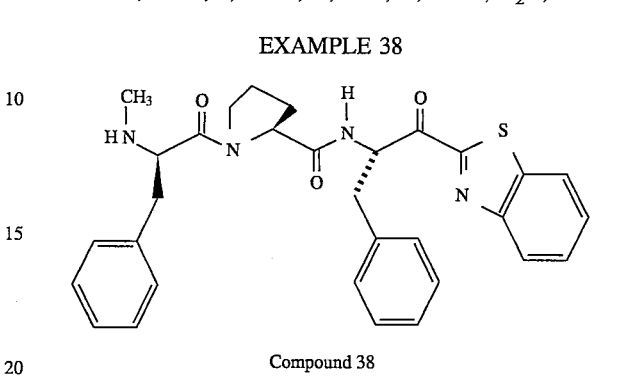

Compound 38

Compound 38 was prepared using the method of Example 12. N-α-Boc-N$^G$-tosyl-L-arginine N,O-dimethyl amide was replaced with N-Boc-L-phenylalanine N,O-dimethylamide and benzothiazole-6-carboxylic acid was replaced with benzothiazole in step a. The remaining steps of the sequence were carried through with only minor modifications to give the title compound as a solid: mp 74°–95° C.; $[\alpha]_D^{25} = -45.3$ (C=1.00, MeOH); FAB-MS m/z541 (MH⁺);
Anal. Calc'd for $C_{31}H_{32}N_4O_3 \cdot 1.5\ CF_3CO_2H \cdot 0.7\ H_2O$: Calculated C, 56.38; F, 11.8; H, 4.86; N, 7.73; $H_2O$, 1.74 Found: C, 56.62; F, 11.48; H, 4.48; N, 7.61; $H_2O$, 1.76

EXAMPLE 39

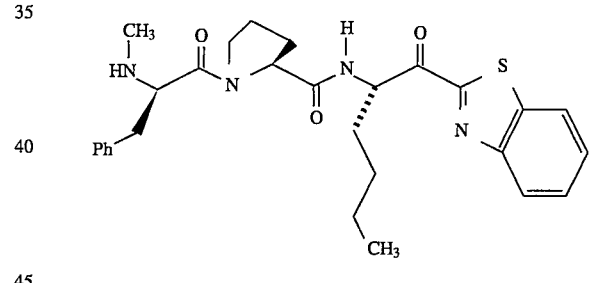

Compound 39

Compound 39 was prepared using the method of Example 12. N-α-Boc-N$^G$-tosyl-L-arginine N,O-dimethyl amide was replaced with N-Boc-L-norleucine N,O-dimethylamide and benzothiazole-6-carboxylic acid was replaced with benzothiazole in step a. The remaining steps of the sequence were carried through with only minor modifications to give the title compound as a solid: $[\alpha]_D^{25} = -80.7$ (C=1.0, MeOH); FAB-MS m/z 507 (MH⁺);
Anal. Calc'd for $C_{28}H_{34}N_4O_3 \cdot 1.5\ CF_3CO_2H \cdot 0.3\ H_2O$: Calculated C, 54.51; F, 12.52; H, 5.33; N, 8.2; $H_2O$, 0.79 Found:

C, 54.6; F, 12.28; H, 5.38; N, .8.18; H$_2$O, 0.60

EXAMPLE 40

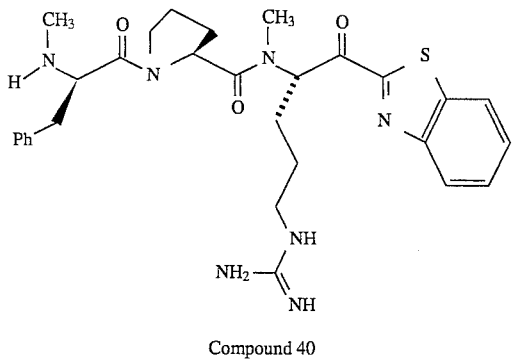

Compound 40

Compound 40 was prepared using the method of Example 12. N-α-Boc-N$^G$-tosyl-L-arginine N,O-dimethyl amide was replaced with N-α-Boc-N-α-methyl-N$^G$-tosyl-L-arginine N,O-dimethylamide and benzothiazole-6-carboxylic acid was replaced with benzothiazole in step a and carried through steps b and c. Step d required the use of bis(2-oxo-3-oxazolidinyl)phosphinic chloride (BOP-Cl) as the coupling agent. The remaining steps of the sequence were carried through with only minor modifications to give the title compound as a solid: $[α]_D^{25} = -91.3$ (C=1.00, MeOH); FAB-MS m/z 564 (MH$^+$);
Anal. Calc'd for C$_{29}$H$_{37}$N$_7$O$_3$S·2.3 CF$_3$CO2H·1.1 H$_2$O: Calculated C, 47.72; F, 15.5; H, 4.95; N, 11.59; H$_2$O, 2.34
Found: C, 47.58; F, 15.69; H, 4.89; N, 11.58; H$_2$O, 2.36

EXAMPLE 41

D-PHENYLALANYL-N-[4-[(AMINOIMINOMETHYL)AMINO]-1S-[(BENZOTHIAZOL-2-YL)CARBONYL]BUTYL]-L-PROLINAMIDE

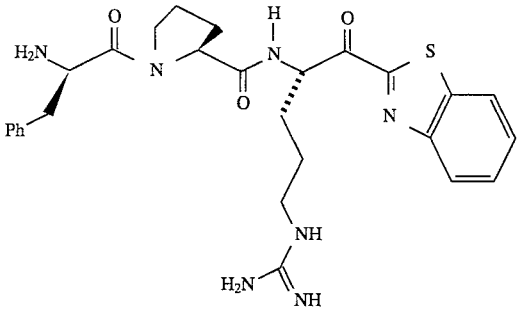

Compound 41

Compound 41 was prepared using the method of Example 12. N-CBZ-N-methyl-D-phenylalanyl-L-proline was replaced with N-CBZ-D-phenylalanyl-L-proline and benzothiazole-6-carboxylic acid was replaced with benzothiazole to give the title compound as a solid: FAB-MS m/z 540 (MH$^+$);

Anal. Calc'd for C$_{27}$H$_{33}$N$_7$O$_3$S·2.4 CF$_3$CO$_2$H·0.9 H$_2$O: Calculated C, 46.27; F, 16.57; H, 4.54; N, 11.8, H$_2$O, 1.96
Found: C, 46.22; F, 16.01; H, 4.59; N, 12.02, H$_2$O, 1.6

EXAMPLE 42

N-METHYL-D-PHENYLALANYL-N-[4-[(AMINOIMINOMETHYL)AMINO]-1S-[(BENZOTHIAZOL-2-YL)CARBONYL]BUTYL]-2S-PIPERIDINECARBOXAMIDE

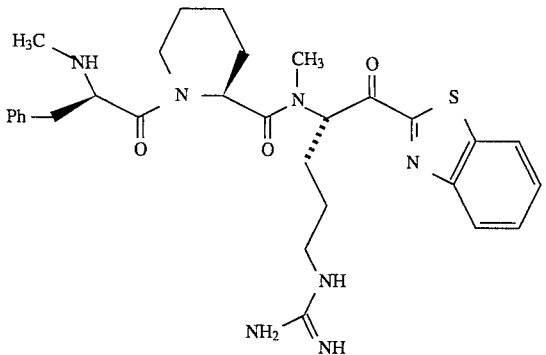

Compound 42 was prepared using the method of Example 12. Benzothiazol-6-carboxylic acid was replaced with benzothiazole in step a and N-CBZ-N-methyl-D-phenylalanyl-L-proline was replaced with N-Boc-N-methylphenylalanyl-L-homoproline in step d to give the title compound as a solid: FAB-MS m/z 564 (MH$^+$);
Anal. Calc'd for C$_{29}$H$_{37}$N$_7$O$_3$S·2.4 CF$_3$CO$_2$H·1.3 H$_2$O: Calculated C, 47.16; F, 15.89; H, 4.92; N, 11.39, H$_2$O, 2.72
Found: C, 46.76; F, 15.62; H, 4.95; N, 11.39, H$_2$O, 2.28

EXAMPLE 43

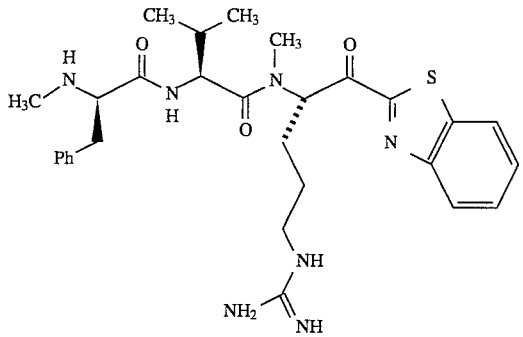

Compound 43

Compound 43 was prepared using the method of example 12. Benzothiazole-6-carboxylic acid was replaced with benzothiazole in step a and N-CBZ-N-methyl-D-phenylalanyl-L-proline was replaced with N-Boc-N-methyl-D-valyl-L-proline acid in step d to give the title compound as a solid: FAB-MS m/z 552 (MH$^+$);
Anal. Calc'd for C$_{28}$H$_{37}$N$_7$O$_3$S·2.3 CF$_3$CO$_2$H·H$_2$O: Calculated C, 47.06; F, 15.76; H, 5.00; N, 11.78, H$_2$O, 2.16 Found:

C, 46.89; F, 16.22; H, 5.06; N, 12.11, H₂O, 2.76

EXAMPLE 44

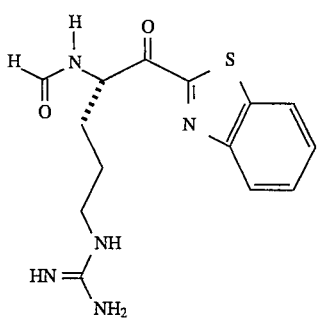

Compound 44

Compound 44 was prepared by treating intermediate 3e with refluxing ethyl formate, oxidizing the resulting product with Dess Martin Periodinane and deprotecting the ketone product with HF to give the title compound as a solid: FAB-MS m/z 560 (MH⁺);
Anal. Calc'd for $C_{14}H_{17}N_5O_2S·1.32\ CF_3CO2H·0.71\ H_2O$:
Calculated C, 41.39; F, 15.60; H, 4.12; N, 14.50; H₂O, 2.66
Found: C, 41.04; F, 15.49; H, 3.97; N, 14.84; H₂O, 2.26

EXAMPLE 45

1-(N-METHYLAMINO)-1-CYCLOHEXYLCARBONYL-N-[4-[(AMINOIMINOMETHYL)AMINO]-1S-[(BENZOTHIAZOL-2-YL)CARBONYL]BUTYL]-L-PROLINAMIDE

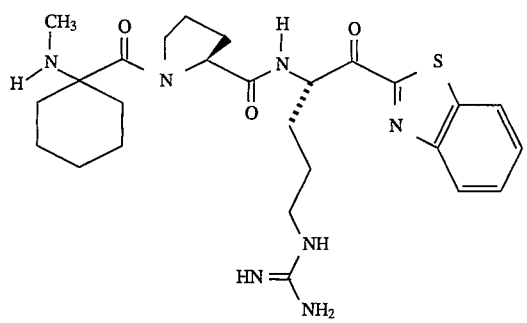

Compound 45

Compound 45 was prepared using the method of Example 12. Benzothiazole-6-carboxylic acid was replaced with benzothiazole in step a and N-CBZ-N-methyl-D-phenylalanyl-L-proline was replaced with 1-(N-Boc-N-methylamino)-1-cyclohexanecarbonyl-L-proline in step d. The remaining steps in the scheme were carried out with minor modifications to give the title compound as a solid: FAB-MS m/z 528 (MH⁺);
Anal. Calc'd for $C_{26}H_{37}N_7O_3S·2.3\ CF_3CO2H·1.8\ H_2O$:
Calculated C, 44.69; F, 15.94; H, 5.26; N, 11.92; H₂O, 3.94
Found: C, 44.37; F, 15.8; H, 4.89; N, 11.75; H₂O, 3.11

EXAMPLE 46

2,2-DIPHENYLGLYCYL-N-[4-[(AMINOIMINOMETHYL)AMINO]-1S-[(BENZOTHIAZOL-2-YL)CARBONYL]BUTYL]-L-PROLINAMIDE

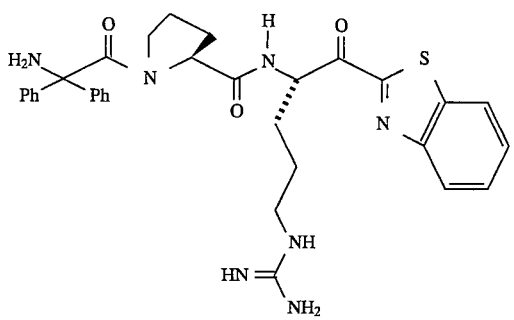

Compound 46

Compound 46 was prepared using the method of Example 12. Benzothiazol-6-carboxylic acid was replaced with benzothiazole in step a and N-CBZ-N-methyl-D-phenylalanyl-L-proline was replaced with N-CBZ-diphenylglycylproline in step d to give the title compound as a solid: FAB-MS m/z 598 (MH⁺);
Anal. Calc'd for $C_{32}H_{35}N_7O_3S·2.6\ CF_3CO2H·1.2\ H_2O$:
Calculated C, 48.79; F, 16.18; H, 4.40; N, 10.71; H₂O, 2.36
Found: C, 48.70; F, 15.78; H, 4.22; N, 10.63; H₂O, 1.37

EXAMPLE 47

α-METHYL-D-PHENYLALANYL-N-[4-[(AMINOIMINOMETHYL)AMINO]-1S-[(BENXOTHIAZOL-2-YL)CARBONYL]BUTYL]-L-PROLINAMIDE

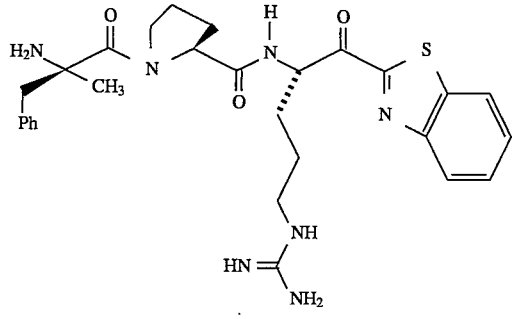

Compound 47

Compound 47 was prepared using the method of Example 12. Benzothiazole-6-carboxylic acid was replaced with benzothiazole in step a and N-CBZ-N-methyl-D-phenylalanyl-L-proline was replaced with N-Boc-α-methyl-D-phenylalanylproline in step d to give the title compound as a solid: FAB-MS m/z 550 (MH⁺);
Anal. Calc'd for $C_{28}H_{35}N_7O_3S·2.6\ CF_3CO2H·1.5\ H_2O$:
Calculated C, 45.67; F, 16.97; H, 4.69; N, 11.23 Found: C, 45.28; F, 16.91; H, 4.46; N, 11.00

EXAMPLE 48

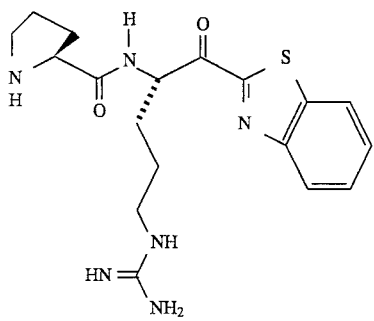

Compound 48

Compound 48 was prepared using the method of Example 12. Benzothiazole replaced benzothiazole-6-carboxylic acid in step a and N-Boc-L-proline replaced N-CBZ-N-methyl-D-phenylalanyl-L-proline in step d to give the title compound as a solid: FAB-MS m/z 389 (MH+);
Anal. Calc'd for $C_{18}H_{24}N_6O_2S·1.9$ $CF_3CO2H·0.9$ $H_2O$:
Calculated C, 42.14; F, 17.43; H, 4.49; N, 13.53, $H_2O$, 2.58
Found: C, 42.30; F, 17.69; H, 4.20; N, 13.18, $H_2O$, 2.61

EXAMPLE 49

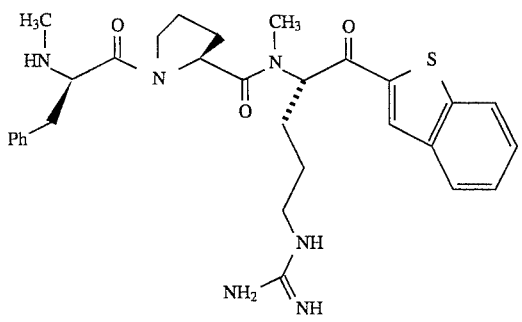

Compound 49

Compound 49 was prepared by the method of Example 12. Benzo[b]thiophene replaced benzothiazole-6-carboxylic acid in step a and the remaining steps in the sequence were carried out with only minor modifications to give the title compound as a solid: $[\alpha]_D^{25}$ =−78.3 (C=1.00, MeOH); FAB-MS m/z 549 (MH+);
Anal. Calc'd for $C_{29}H_{36}N_6O_3S·2.4$ $CF_3CO2H·1.5$ $H_2O$:
Calculated C, 47.80; F, 16.10; H, 4.91; N, 9.89, $H_2O$, 3.18
Found: C, 47.68; F, 15.81; H, 4.82; N, 9.74, $H_2O$, 3.18

EXAMPLE 50

N-METHYL-D-PHENYLALANYL-N-[4-[(AMINOIMINOMETHYL)AMINO]-1S-[(6-METHOXYBENXOTHIAZOL-2-YL)CARBONYL]BUTYL]-L-PROLINAMIDE

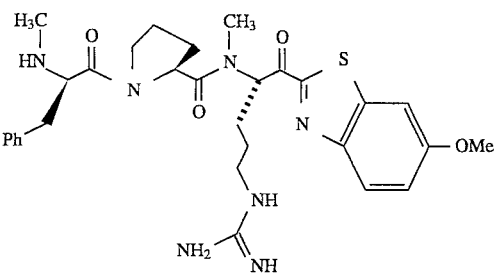

Compound 50

Compound 50 was prepared using the method of Example 12. Benzothiazole-6-carboxylic acid was replaced with 6-methoxybenzothiazole in step a. The remaining steps in the sequence were run with only minor modifications to give the title compound as a solid: $[\alpha]_D^{25}$ =−76.6 (C=0.73, MeOH); FAB-MS m/z 549 (MH+);
Anal. Calc'd for $C_{29}H_{37}N_7O_4S·2.3$ $CF_3CO2H·1.75$ $H_2O$:
Calculated C, 47.80; F, 16.10; H, 4.91; N, 9.89, $H_2O$, 3.18
Found: C, 47.68; F, 15.81; H, 4.82; N, 9.74, $H_2O$, 3.18

EXAMPLE 51

N-METHYL-D-PHENYLALANYL-N-[4-[(AMINOIMINOMETHYL)AMINO]-1S-[(4,5,6,7-TETRAHYDROBENZOTHIAZOL-2-YL)CARBONYL]BUTYL]-L-PROLINAMIDE

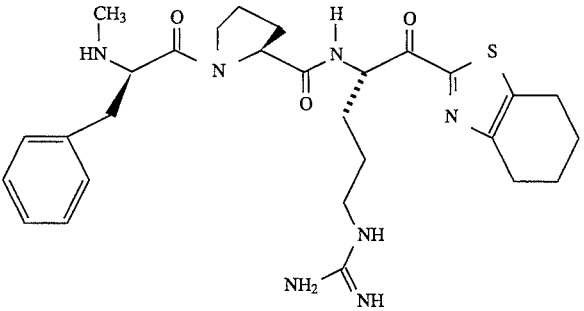

Compound 51

Compound 51 was prepared using the method of Example 12. Benzothiazole-6-carboxylic acid was replaced with 4,5,6,7-tetrahydrobenzothiazole in step a, and the remaining steps of the sequence were followed to give the title compound as a solid: mp 50°–60° C.; FAB-MS m/z 554 (MH+);
Anal. Calc'd for $C_{28}H_{39}N_7O_3S·2.6$ $CF_3CO_2H·1.4$ $H_2O$: Calculated: C, 45.55; F, 16.93; H, 5.11; N, 11.20; $H_2O$, 2.88

Found: C, 45.71; F, 17.16; H, 5.31; N, 11.34; H₂O, 2.96

EXAMPLE 52

N-METHYL-D-PHENYLALANYL-N-[4-
[(AMINOIMINOMETHYL)AMINO]-
1S-[(NAPTHO[2,1-D]THIAZOL-2-
YL)CARBONYL]BUTYL]-L-PROLINAMIDE

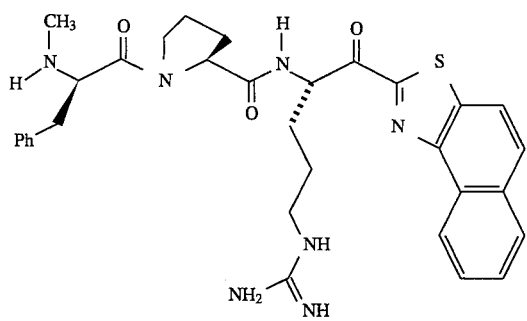

Compound 52

Compound 52 was prepared using the method of Example 12 by replacing 6-carboxybenzothizole with naphtho[2,1-d]thiazole to give a solid: $[\alpha]_D^{25}$ =–103.0 (C=1.00, MeOH); FAB-MS m/z 560 (MH⁺);
Anal. Calc'd for $C_{32}H_{37}N_7O_3S \cdot 3.46\ CF_3CO_2H \cdot 1.3\ H_2O$: Calculated C, 45.93; F, 19.38; H, 4.26; N, 9.36; H₂O, 2.30
Found: C, 45.60; F, 19.06; H, 4.03; N, 9.70; H₂O, 1.96

EXAMPLE 53

STEP a          53a

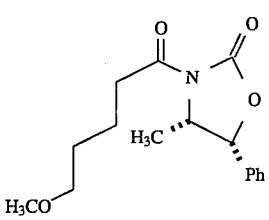

A solution of 5-methoxypentanoic acid (6.80 g, 0.052 mol; Kirmse, K.; Jansen, U. *Chem. Ber.* 1985, 118, 2607–2625) and triethylamine (6.80 g, 0.067 mol) in 100 mL of anhydrous THF was cooled to –78° C. while stirring under argon. Pivaloyl chloride (6.80 g, 0.067 mol) was added to the reaction mixture dropwise over 15 min at –78° C. After 15 min, the reaction was warmed to 0° C., stirred for 1.5 h, and then recooled to –78° C.
Meanwhile, n-BuLi (58 mL of 1.6M in hexanes, 0.093 mol) was added dropwise to a solution of (4S,5R)-(–)-4-methyl-5-phenyl-2-oxazolidinone (16.4 g, 0.093 mol) in 100 mL of anhydrous THF over 30 min while stirring under argon at –78° C. After 15 min, this reaction was added slowly to the above mixed-anhydride reaction while stirring under argon at –78° C. The reaction mixture was allowed to slowly warm to room temperature over 18 h, quenched with 1N aqueous KHSO₄, and the solvents were removed in vacuo at 40° C. The residue was partitioned between water and CH₂Cl₂ and the aqueous layer was extracted 3× with CH₂Cl₂. The combined CH₂Cl₂ extracts were washed twice with brine, dried over anhydrous Na₂SO₄, and concentrated in vacuo at 40° C. The residue was purified by chromatography on silica gel eluting with CH₂Cl₂/EtOAc (95:5) to give 8.2 g (55%) of 53a as a white solid; FAB-MS m/z 292 (MH⁺).

STEP b          53b

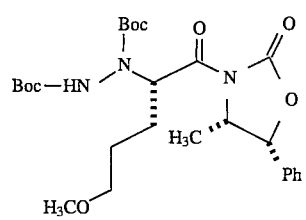

Compound 53a (3.81 g, 0.013 mol) reacted with di-tert-butyl azodicarboxylate (0.48 g, 0.01 5 mol) according to the general method of D. A. Evans et al (*Tetrahedron* 1988, 44, 5525–5540) to give crude 53b. The crude product was purified by chromatography on silica gel eluting with CH₂Cl₂/hexane/acetonitrile (70:30:7) to give pure 53b (2.33 g, 33%) as a white solid; FAB-MS m/z 522 (MH⁺).

STEP c          53c

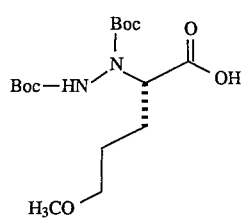

Compound 53b (2.33 g, 0.0045 mol) was dissolved in 18 mL of THF, cooled to 0° C., and treated with a solution of LiOH·H₂O (0.46 g, 0.0107 mol) in 9 mL of H₂O. Aqueous H₂O₂ (1.1 mL of 30%, 0.010 mol) was added and the reaction was stirred at 0° C. for 3h. The reaction mixture was partitioned between aqueous 1N HCl and CH₂Cl₂ and the acidic aqueous layer was extracted with CH₂Cl₂. The combined CH₂Cl₂ extracts were washed with brine, dried over anhydrous MgSO₄, and concentrated in vacuo at 40° C. The residue was purified by chromatography on silica gel eluting with EtOAc/hexane/HOAc to afford 53c as a white solid; FAB-MS m/z 363 (MH⁺).

STEP d          53d

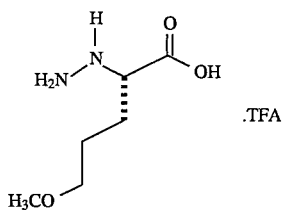

Compound 53c (2.15g, 0.0593 mol) was dissolved in 215 mL of TFA/CH₂Cl₂ (1:4 v/v) and stirred at room temperature under argon for 1.5 h. The solvents were removed in vacuo at 20° C. to furnish 53d (2.07 g); FAB-MS m/z 163 (MH⁺).

STEP e          53e

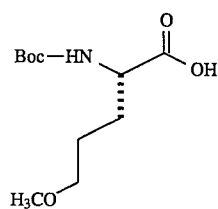

Compound 53d was dissolved in absolute ethanol (100 mL), combined with PtO₂ (0.300 g), and placed on a Parr hydrogenation apparatus under hydrogen pressure (55 psig) at room temperature over 24h. The reaction mixture was filtered through filter aid and concentrated in vacuo. The residue was dissolved in methanol (50 mL) and the pH was adjusted to pH 8 with Et₃N (ca. 2 mL). The solution was cooled to 0° C., treated with di-tert-butyl dicarbonate (2.0 g, 0.009 mol), and allowed to slowly warm to room temperature over 20 h. The reaction was concentrated in vacuo at 40° C. and partitioned between EtOAc (50 mL) and cold (5° C.) aqueous 1N HCl (50 mL). The organic extract was extracted with cold aqueous 1N HCl (50 mL), washed with brine, dried over anhydrous Na₂SO₄, and concentrated in vacuo at 40° C. to give 53e (2.15 g) as a white solid; FAB-MS m/z 248 (MH⁺).

STEP f                                          53f

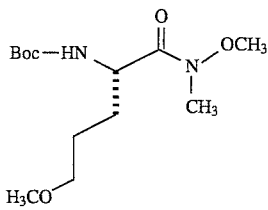

Compound 53e (1.48 g, 0.0060 mol) was dissolved in 70 mL of anhydrous CH₂Cl₂, combined with N,O-dimethylhydroxylamine hydrochloride (0.878 g, 0.0090 mol). The resulting mixture was adjusted to pH 8 with Et₃N and treated with bis(2-oxo-3-oxazolidinyl)phosphinic chloride (BOP-Cl; 2.29 g, 0.0090 mol) while stirring at room temperature under argon. After 2 h, the reaction was partitioned between CH₂Cl₂ and cold aqueous 1N HCl. The organic layer was extracted with saturated aqueous NaHCO₃, brine, dried over anhydrous MgSO₄, and concentrated in vacuum. The residue was partially dissolved in methanol and the insolubles were removed by filtration. The filtrate was concentrated in vacuo to afford 53f (1.00 g, 57%) as a white solid; FAB-MS m/z 291 (MH⁺).

STEP g

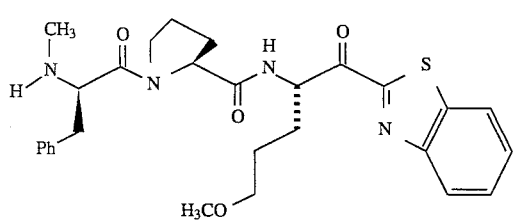

Compound 53

Amide 53f was converted to Compound 53 by following the general procedures of Example 3. Compound 53f was reacted with 2-lithiobenzothiazole as described for 3c. The resulting ketone intermediate was carried through the procedures used to prepare 3d and 3e and the resulting amino alcohol was subsequently coupled with (CBZ)-N-methyl-D-phenylalanyl-L-proline by following the method of step 3f. This intermediate was analogously carried through the remaining steps of Example 3 to give compound 53, which was purified by reverse-phase HPLC eluting with H₂O/acetonitrile/TFA (50:50:0.2) to afford compound 53 as a white solid; $[\alpha]_D^{25}$ −85.3 (c 0.26, MeOH); FAB-MS m/z 853 (MH⁺).

Anal. for C₂₈H₃₄N₄O₄S·2.15 TFA·1.1 H₂O: Calculated: C, 51.12; H, 5.33; N, 7.85; F, 11.98; H₂O, 2.77 Found: C, 51.16; H, 5.17; N, 7.87; F, 11.58; H₂O, 2.45.

EXAMPLE 54

N-METHYL-D-PHENYLALANYL-N-[4-[(AMINOIMINOMETHYL)AMINO]-1S-[(4-CARBOXYTHIAZOL-2-YL)CARBONYL]BUTYL]-L-PROLINAMIDE

STEP a                                          54a

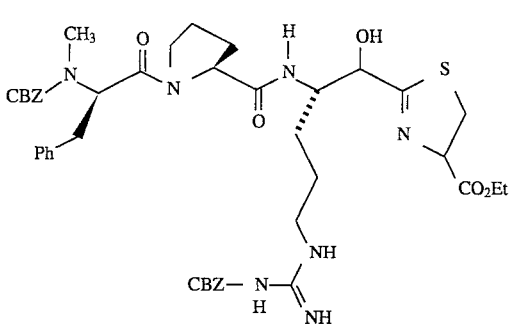

A mixture of intermediate 1b (5.09 g, 6.52 mmol) and L-cysteine ethyl ester·HCl (2.42 g, 13.05 mmol) in anhydrous CH₂Cl₂ (127 mL) was stirred at room temperature under argon over 16 h. The resulting mixture was filtered through filter aid, concentrated in vacuo, and partitioned between brine and ethyl acetate. The aqueous layer was extracted with several portions of ethyl acetate and the combined organic extracts were dried (Na₂SO₄) and concentrated in vacuo. The residue was purified by chromatography on silica gel eluting with CH₂Cl₂:MeOH:NH₄OH (90:9:1) to give 54a as a white foam.

STEP b                                          54b

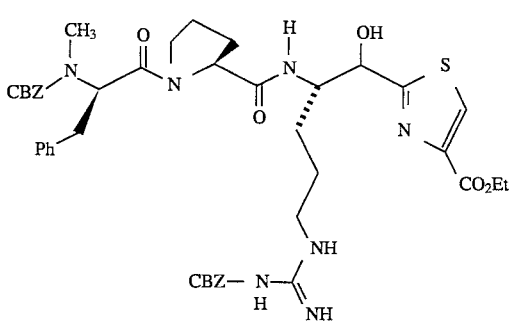

A mixture of 54a (1.0 g, 1.18 mmol) and MnO₂ (1.00 g, 14.38 mmol) in anhydrous CH₂Cl₂ (28 mL) was stirred at room temperature under argon for 4.5 h. An additional portion MnO₂ (0.25 g) was added and the mixture was stirred for another 2.5 h. The resulting mixture was filtered through filter aid, and concentrated in vacuo to give thiazole 54b as a crude solid.

STEP c

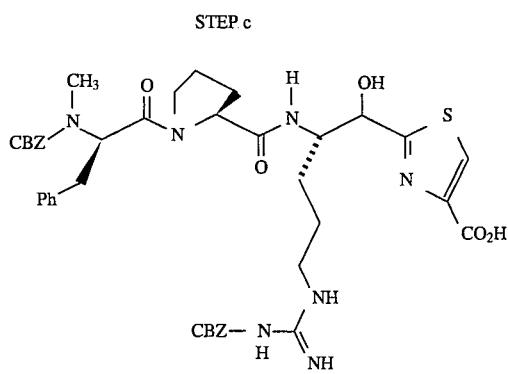

54c

LiOH (65 mg, 2.64 mmol) and H₂O (0.1 mL) in dioxane (0.9 mL) was stirred under argon for 3 h. The resulting mixture was diluted with H₂O and extracted with several portions of ether. The aqueous layer was separated and acidified to pH 4 with 1N HCl and extracted with several portions of CH₂Cl₂. The combined CH₂Cl₂ extracts were washed with brine, dried (Na₂SO₄) and concentrated in vacuo to give the acid 54b as a solid.

STEP d

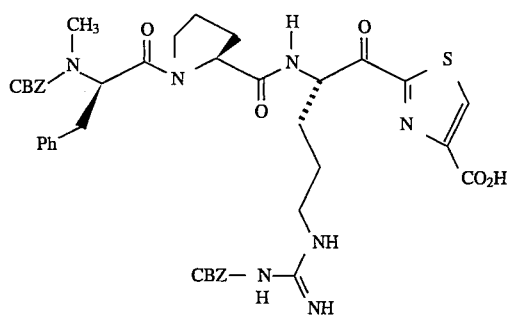

54d

A mixture of 54c (252 mg, 0.31 mmol) and peridoinane (197 mg, 0.464 mmol) in CH₂Cl₂ (10 mL) was stirred under N₂ at room temperature for 1 h. Additional portions of periodinane were added (132 mg, 0.31 mmol) were added over 3h and the resulting mixture was quenched with aqueous Na₂S₂O₃. The aqueous layer was acidified to pH 3.0 with acetic acid, then washed with several portions of CH₂Cl₂. The combined organic extracts were washed with brine, filtered through diatomaceous earth and and concentrated in vacuo. The residue was purified by reverse-phase HPLC using CH₃CN:H₂O:TFA (50:50:0.2) to give the ketone 54d as a solid.

STEP e

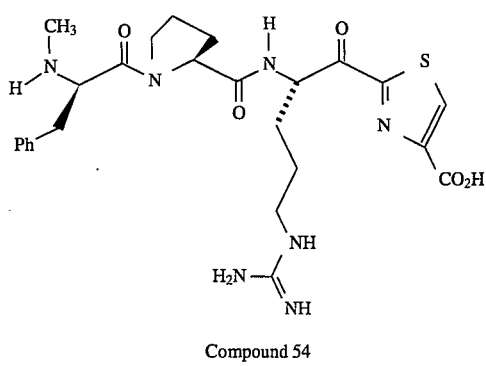

Compound 54

The intermediate ketone 54d (140 mg, 0.17 mmol) and anisole (4 mL) were placed in a Teflon reaction tube of an HF apparatus under anhydrous conditions and cooled to −78° C. HF (8 mL) was distilled into this tube and upon completion of addition, the temperature of the mixture was allowed to rise to −10° C. This mixture was stirred for 1 h at −20° to −10° C., concentrated in vacuo and triturated with several portions of ether to give a solid. This solid was purified by reverse-phase HPLC eluting with water/acetonitrile/TFA (70:30:0.2) and lyophilized to give compound 54 as a solid: $[\alpha]_D^{25} = -86.5$ (C=0.65, H₂O); FAB-MS m/z 860 (MH⁺);

Anal. Calc'd for $C_{25}H_{33}N_7O_5S \cdot 2.5\ CF_3CO_2H \cdot 1.7\ H_2O$: Calculated C, 41.93; H, 4.56; N, 11.41; H₂O, 3.56 Found: C, 41.59; H, 4.53; N, 11.84; H₂O, 3.40

EXAMPLES 55 and 56

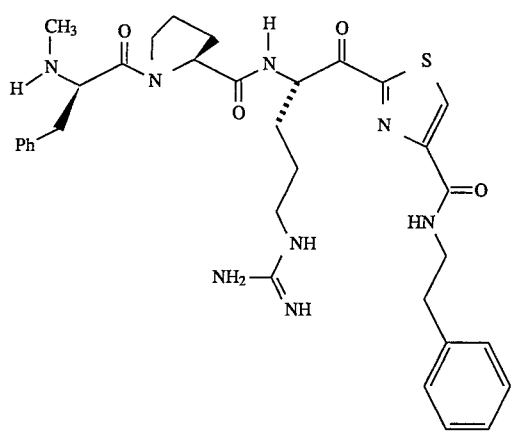

Compound 55

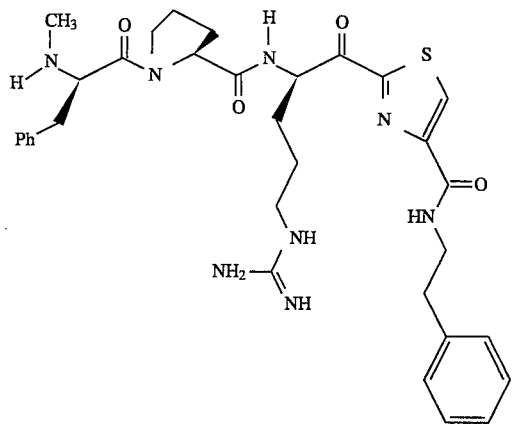

Compound 56

Compounds 55 and 56 were prepared by modifying Example 54. BOP-Cl (13 mg, 0.03 mmol) was added to a stirred mixture of intermediate 54c (21.8 mg, 0.027 mmol), triethylamine (5.6 μL, 0.077 mmol) DMF (1.5 mL) and phenethylamine (5. μL, 0.041 mmol) at 5° C. under argon. The resulting mixture was stirred for 16 h, concentrated in vacuo, and partitioned between ethyl acetate and saturated aqueous NaHCO₃. The aqueous layer was extracted with several portions of ethyl acetate and the combined organic extracts were dried (Na₂SO₄) and concentrated in vacuo to give the protected amide. This amide was deprotected in the manner of Example 54 to give the respective title compounds as solids:

Compound 55: $[\alpha]_D^{25} = -67.5$ (C=0.74, MeOH); FAB-MS m/z 647 (MH$^+$);
Anal. Calc'd for $C_{33}H_{42}N_8O_4S \cdot 2.6\ CF_3CO2H \cdot 1.2\ H_2O$:
Calculated C, 41.93; H, 4.56; N, 11.41; H$_2$O, 3.56 Found: C, 41.59; H, 4.53; N, 11.84; H$_2$O, 3.40
Compound 56: FAB-MS m/z 647 (MH$^+$)

EXAMPLE 57

STEP a    57a

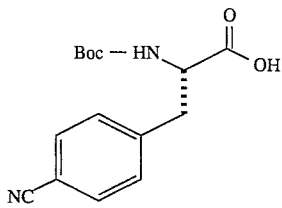

L-4-Cyanophenylalanine (36.1 g, 0.19 mol; EP 0513675 A1) was combined with Et$_3$N (26 mL, 0.19 mol) in 550 mL of H$_2$O. The resulting solution was treated with di-tert-butyl dicarbonate (68.0 g, 0.31 mol), stirred at room temperature over 18 h, and cooled to 5° C. The pH was adjusted to pH 1 with concentrated aqueous HCl and the acidic aqueous layer was extracted twice with EtOAc (500 mL). The combined EtOAc layers were washed twice with brine (200 mL), dried over anhydrous Na$_2$SO$_4$, and concentrated in vacuo. The residue was triturated with hexane to give 57a as a light-pink solid (50.0 g, 87%); mp=145°–147° C. (decomposition); $[\alpha]_D^{25}$ +3.3 (c 1.0, MeOH); FAB-MS m/z 291 (MH)$^+$.

STEP b    57b

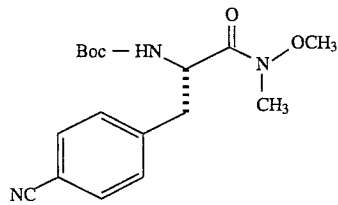

A solution of 57a (25 g, 0.086 mol), N,O-dimethylhydroxylamine hydrochloride (12.7 g, 0.130 mol) in anhydrous DMF (500 mL) was cooled to 0° C. while stirring under argon and treated with Et$_3$N (23.3 g, 0.230 mol). Benzotriazol-1-yloxy-tris(dimethylamino)phosphonium hexafluorophosphate (BOP; 42.1 g, 0.095 mol) was added portionwise over 10 min and the reaction was stirred at 0°–5° C. over 18 h while maintaining the pH at pH 8–9 by the addition of Et$_3$N. The reaction was concentrated in vacuo and the residue was partitioned between CH$_2$Cl$_2$ (500 mL) and H$_2$O (250 mL). The organic layer was washed with 50 mL of 5% aqueous NaHCO$_3$, 50 mL of aqueous 1N HCl, 100 mL of H$_2$O, dried over anhydrous Na$_2$SO$_4$, and concentrated in vacuo. The residue was purified by chromatography on silica gel eluting with CHCl$_3$/MeOH (95:5) to give 57b as a yellow solid (22.1 g, 70%); FAB-MS m/z 334 (MH)$^+$.

STEP c    57c

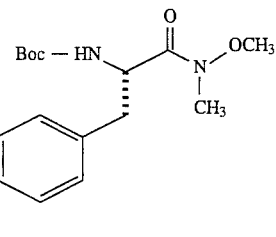

Compound 57b (28.7 g, 0.0861 mol) and Et$_3$N (100 mL, 0.72 mol) were dissolved pyridine (400 mL). Anhydrous H$_2$S was bubbled into this solution over 3 h at room temperature. The reaction vessel was then stoppered, allowed to stand at room temperature for 60 h, and concentrated in vacuo at 30° C. The residue was diluted with H$_2$O (500 mL), cooled to 5° C., acidified to pH 4–5 with concentrated aqueous HCl, and extracted with EtOAc (500 mL). The organic layer was extracted twice with 250 mL of aqueous 1N HCl, twice with 200 mL of brine, dried over anhydrous MgSO$_4$, and concentrated in vacuo to give the 57c (27.8 g, 88%); FAB-MS m/z 368 (MH)$^+$.

STEP d    57d

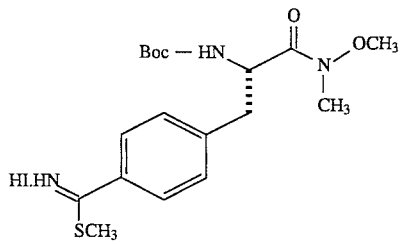

A solution of 57c (27.0 g, 0.074 mol) and methyl iodide (75 mL,) in acetone (750 mL) was heated at reflux while stirring under argon for 1 h. After cooling to room temperature, the reaction was concentrated in vacuo to give crude 57d as an amber glass, which was used directly in the next step; FAB-MS m/z 381 (MH)$^+$.

STEP e    57e

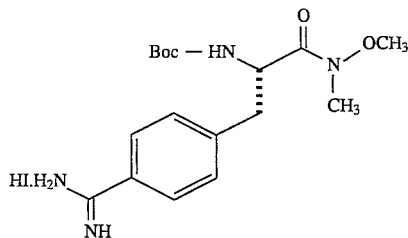

Compound 57d (38.0 g, 0.075 mol) was added to a solution of ammonium acetate (8.70 g, 0.112 mol) in methanol (200 mL) and heated at reflux while stirring under argon for 3.5 h. After cooling to room temperature, the reaction was concentrated in vacuo and the residue was partitioned between CHCl$_3$ (500 mL) and saturated aqueous NaHCO$_3$. The CHCl$_3$ was filtered, washed with brine, dried over anhydrous Na$_2$SO$_4$, and concentrated in vacuo to give 57e as a light yellow glass; FAB-MS m/z 351 (MH)$^+$.

STEP f 57f

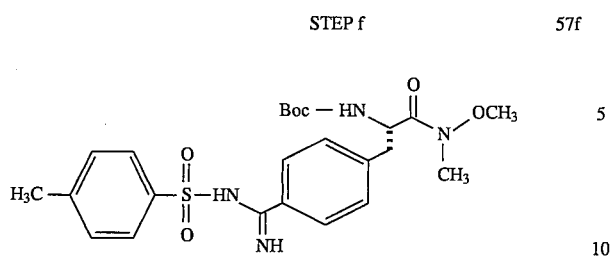

A solution of 57e (24.3 g, 0.069 mol) and tosyl chloride (14.6 g, 0.076 mol) in acetone (500 mL) was cooled to −15° C. 1,8-Diazabicyclo[5.4.0]undeo-7-ene (DBU; 21.4 g, 0.139 mol) was added dropwise while stirring at −15° C. over 45 min. and this mixture was allowed to slowly warm to room temperature over 3 h. The reaction was diluted with 100 mL of methanol and concentrated in vacuo. The residue was purified by chromatography on silica gel eluting with EtOAc/hexane (3:1) to give 57f (14.4 g, 41%) as a white solid; FAB-MS m/z 505 (MH)$^+$.

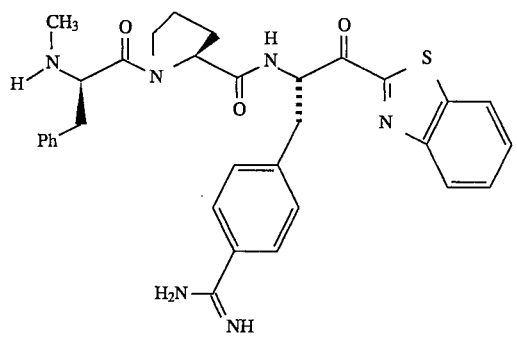

Compound 57

Amide 57f was converted to Compound 57 by following the general procedures of Example 3. Compound 57f was reacted with 2-lithiobenzothiazole as described for 3c. The resulting ketone intermediate was carried through the procedures used to prepare 3d and 3e and the resulting amino alcohol was subsequently coupled with (CBZ)-N-methyl-D-phenylalanyl-L-proline by following the method of step 3f. This intermediate was analogously carried through the remaining steps of Example 3; note that the HF cleavage step (STEP h) required 6h at room temperature instead of 3 h at 0° C. The resulting compound 57, was purified by reverse-phase HPLC eluting with H$_2$O/acetonitrile/TFA (65:35:0.2) to afford compound 57 as a white solid; FAB-MS m/z 583 (MH)$^+$.
Anal. for C$_{32}$H$_{34}$N$_6$O$_3$S·2.25 TFA·1.0 H$_2$O: Calculated: C, 51.14; H, 4.50; N, 9.80; F, 14.96; S, 3.74; H$_2$O, 2.10 Found: C, 50.96; H, 4.39; N, 9.60; F, 14.66; S, 3.77; H$_2$O, 1.72.

EXAMPLE 58

STEP a 58a

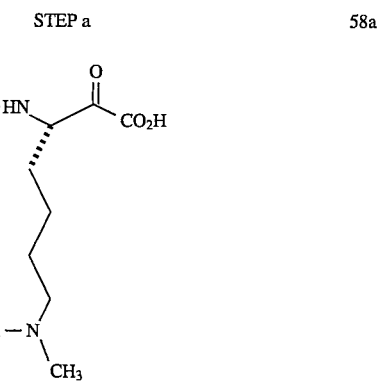

N-ε-Methyl-L-lysine was reacted with 4-methoxy-2,3,6-trimethylbenzenesulfonyl (Mtr) chloride according to method used to prepare N-ε-Mtr-L-lysine described by M. Fujino et al. in *Chem. Pharm. Bull. Jpn.* 1982, 30, 2766. The resulting N-ε-methyl-N-ε-Mtr-L-lysine (5.00 g, 0.0134 mol) was dissolved in dioxane (52 mL), diluted with H$_2$O 952 mL), cooled to 0° C., and adjusted to pH 11 with aqueous 3N NaOH. Di-tert-butyl dicarbonate (8.79 g, 0.040 mol) was added and the reaction was stirred at 0° C. while maintaining the pH at pH 10–11 over 18 h. The solvents were removed in vacuo and the residue was partitioned between H$_2$O (100 mL) and ether. The basic aqueous layer (pH 11) was extracted again with ether (2×), cooled to 0° C., adjusted to pH 3 with aqueous 3N HCl, and extracted with EtOAc (3×). The combined EtOAc extracts were washed with brine, dried over anhydrous Na$_2$SO$_4$, and concentrated in vacuo to give 58a (3.34 g, 53%) as a white foam; FAB-MS m/z 473 (MH)$^+$.

STEP b 58b

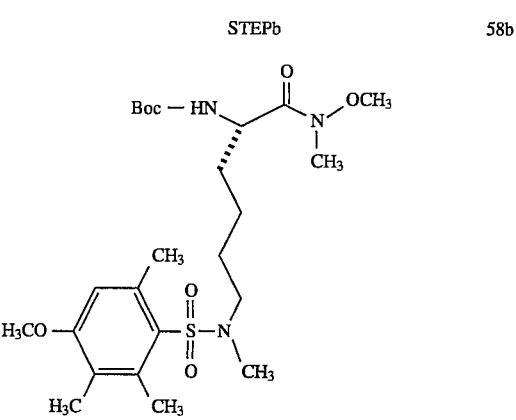

Compound 58b was reacted with N,O-dimethylhydroxylamine hydrochloride according to the general procedure used to prepare 57b to yield 58b as a white solid; m/z 516 (MH)$^+$.

STEP c

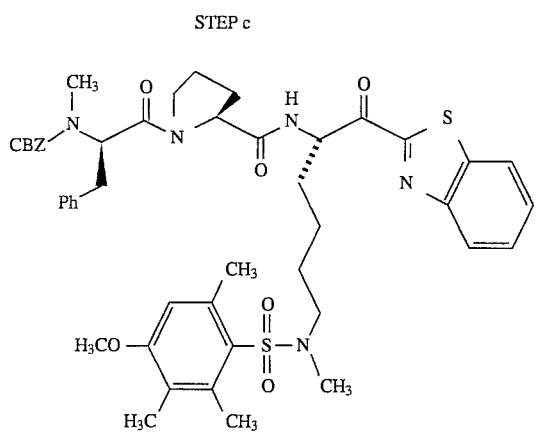

Amide 58b was converted to 58d by following the general procedures of Example 3. Compound 58b was reacted with 2-lithiobenzothiazole as described for 3c. The resulting ketone intermediate was carried through the procedures used to prepare 3d and 3e and the resulting amino alcohol was subsequently coupled with (CBZ)-N-methyl-D-phenylalanyl-L-proline by following the method of step 3f. This intermediate was oxidized with the Dess-Martin periodinane as described for 3g to furnish 58d; m/z 883 (MH)$^+$.

STEP d

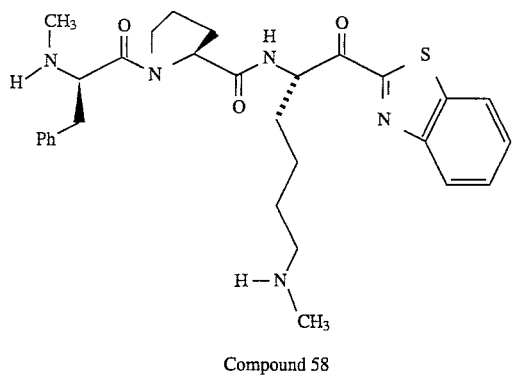

Compound 58

Compound 58d (0.025 g, 0.028 mmol), pentamethylbenzene (0.32 g), and dimethylsulfide (0.63 mL) were dissolved in 3 mL of anhydrous trifluoroacetic acid and cooled to 5° C. while stirring under argon. Anhydrous HBr gas was bubbled through the solution over 15 min. and the reaction was allowed to slowly warm to room temperature over 15 h. The solvents were removed in vacuo and the residue was triturated with anhydrous ether and purified by reverse-phase HPLC eluting with H$_2$O/acetonitrile/TFA (60:40:0.2) to give Compound 58 as a white solid; FAB-MS m/z 536 (MH)$^+$.

What is claimed is:

1. A compound of the formula I:

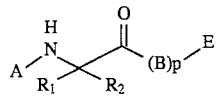

wherein:

A is selected from the group consisting of $C_{1-8}$alkyl, carboxy$C_{1-4}$alkyl, $C_{1-4}$alkoxycarbonyl$C_{1-4}$alkyl, phenyl$C_{1-4}$alkyl, substituted phenyl$C_{1-4}$alkyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, formyl, $C_{1-4}$ alkoxycarbonyl, $C_{1-12}$alkylcarbonyl, phenyl$C_{1-4}$alkoxycarbonyl, $C_{3-7}$cycloalkylcarbonyl, phenylcarbonyl, substituted phenylcarbonyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, $C_{1-4}$alkylsulfonyl, $C_{1-4}$alkoxysulfonyl, perfluoro$C_{1-4}$alkylsulfonyl, phenylsulfonyl, substituted phenylsulfonyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 10-camphorsulfonyl, phenyl$C_{1-4}$alkylsulfonyl, substituted phenyl$C_{1-4}$alkylsulfonyl, $C_{1-4}$alkylsulfinyl, perfluoro$C_{1-4}$alkylsulfinyl, phenylsulfinyl, substituted phenylsulfinyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, phenyl$C_{1-4}$alkylsulfinyl, substituted phenyl$C_{1-4}$alkylsulfinyl, 1-naphthylsulfonyl, 2-naphthylsulfonyl or substituted naphthylsulfonyl where the naphthyl substituents are independently selected from one or more of, $C_{1-4}$alkyl, perfluoro$C_{1-4}$alkyl, $C_{1-4}$alkoxy, hydroxy, halo, amido, nitro, amino, carboxy or $C_{1-4}$alkoxycarbonyl, 1-naphthylsulfinyl, 2-naphthylsulfinyl or substituted naphthylsulfinyl where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl;

a D or L amino acid which is coupled at its carboxy terminus to the nitrogen depicted in formula I and is selected from the group consisting of alanine, asparagine, 2-azetidinecarboxylic acid, glycine, N-C$_{1-8}$alkylglycine, proline, 1-amino-1-cycloC$_{3-8}$alkylcarboxylic acid, thiazolidine-4-carboxylic acid, 5,5-dimethylthiazolidine-4-carboxylic acid, oxazolidine-4-carboxylic acid, pipecolinic acid, valine, methionine, cysteine, serine, threonine, norleucine, leucine, tert-leucine, isoleucine, phenylalanine, 1-naphthalanine, 2-naphthalanine, 2-thienylalanine, 3-thienylalanine, [1,2,3,4]-tetrahydroisoquinoline-1-carboxylic acid and [1,2,3,4]-tetrahydroisoquinoline-2-carboxylic acid where the amino terminus of said amino acid is connected to a member selected from the group consisting of $C_{1-4}$alkyl, tetrazol-5-yl-$C_{1-2}$alkyl, carboxy$C_{1-4}$alkyl, $C_{1-4}$ alkoxycarbonyl$C_{1-4}$alkyl, phenyl$C_{1-4}$alkyl, substituted phenyl $C_{1-4}$alkyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3-carbonyl, 1-methylamino-1-cyclohexanecarbonyl, 1-hydroxy-1-cyclohexanecarbonyl, 1-hydroxy-1-phenylacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-12}$alkylcarbonyl, perfluoro$C_{1-4}$alkyl$C_{0-}$ 4alkylcarbonyl, phenylC$_{1-4}$alkylcarbonyl, substituted phenylC$_{1-4}$alkylcarbonyl where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl) 1,1-diphenylC$_{1-4}$alkylcarbonyl, substituted 1,1-diphenylC$_{1-4}$alkylcarbonyl where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, perfluoroC$_{1-4}$alkylsulfonyl, C$_{1-4}$alkylsulfonyl, C$_{1-4}$alkoxysulfonyl, phenylsulfonyl, substituted phenylsulfonyl where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 10-camphorsulfonyl, phenylC$_{1-4}$alkylsulfonyl, substituted phenylC$_{1-4}$alkylsulfonyl, perfluoroC$_{1-4}$alkylsulfinyl, C$_{1-4}$alkylsulfinyl, phenylsulfinyl, substituted phenylsulfinyl where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, phenylC$_{1-4}$alkylsulfinyl, substituted phenylC$_{1-4}$alkylsulfinyl where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 1-naphthylsulfonyl, 2-naphthylsulfonyl, substituted naphthylsulfonyl where the naphthyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 1-naphthylsulfinyl, 2-naphthylsulfinyl, and substituted naphthylsulfinyl where the naphthyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl;

or a poly peptide comprised of two amino acids, where the first amino acid is a D or L amino acid, bound via its carboxy terminus to the nitrogen depicted in formula I and is selected from the group consisting of glycine, N-C$_{1-8}$alkylglycine, alanine, 2-azetidinecarboxylic acid, proline, thiazolidine-4-carboxylic acid, 5,5-dimethylthiazolidine- 4-carboxylic acid, oxazolidine-4-carboxylic acid, 1-amino-1-cycloC$_{3-8}$alkylcarboxylic acid, 3-hydroxyproline, 4-hydroxyproline, 3-(C$_{1-4}$alkoxy)proline, 4-(C$_{1-4}$alkoxy)proline, 3,4-dehydroproline, 2,2-dimethyl-4-thiazolidine carboxylic acid, 2,2-dimethyl-4-oxazolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalanine, [1,2,3,4]-tetrahydroisoquinoline- 1-carboxylic acid, [1,2,3,4]-tetrahydroisoquinoline- 2-carboxylic acid, aspartic acid-4-C$_{1-4}$ alkyl ester and glutamic acid-5-C$_{1-4}$alkyl ester and the second D or L amino acid, is bound to the amino terminus of said first amino acid, and is selected from the group consisting of phenylalanine, 4-benzoylphenylalanine, 4-carboxyphenylalanine, 4-(carboxy C$_{0-2}$alkyl)phenylalanine, substituted phenylalanine where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 3-benzothienylalanine, 4-biphenylalanine, homophenylalanine, octahydroindole-2-carboxylic acid, 2-pyridylalanine, 3-pyridylalanine, 4-thiazolylalanine, 2-thienylalanine, 3-(3-benzothienyl)alanine, 3-thienylalanine, tryptophan, tyrosine, asparagine, 3-tri-C$_{1-4}$alkylsilylalanine, cyclohexylglycine, diphenylglycine, phenylglycine, methionine sulfoxide, methionine sulfone, 2,2-dicyclohexylalanine, 2-(1-naphthylalanine), 2-( 2-naphthylalanine), phenyl substituted phenylalanine where the substituents are selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, aspartic acid, aspartic acid-4-C$_{1-4}$alkyl ester, glutamic acid, glutamic acid-5-C$_{1-4}$ alkyl ester, cycloC$_{3-8}$alkylalanine, substituted cycloC$_{3-8}$alkylalanine where the ring substituents are carboxy, C$_{1-4}$alkylcarboxy, C$_{1-4}$alkoxycarbonyl or aminocarbonyl, 2,2-diphenylalanine and all alpha-C$_{1-5}$alkyl of all amino acid derivatives thereof, where the amino terminus of said second amino acid is unsubstituted or monosubstituted with a member of the group consisting of formyl, C$_{1-12}$alkyl, tetrazol-5-ylC$_{1-2}$alkyl, carboxyC$_{1-8}$alkyl, carboalkoxyC$_{1-4}$alkyl, phenyl C$_{1-4}$alkyl, substituted phenylC$_{1-4}$alkyl where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 1,1-diphenylC$_{1-4}$alkyl, C$_{1-6}$alkoxycarbonyl, phenylC$_{1-6}$alkoxycarbonyl, C$_{1-12}$alkylcarbonyl, perfluoroC$_{1-4}$alkylC$_{0-4}$alkylcarbonyl, phenylC$_{1-4}$alkylcarbonyl, substituted phenylC$_{1-4}$alkylcarbonyl where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 1,1-diphenylC$_{1-4}$alkylcarbonyl, C$_{1-4}$alkylsulfonyl, C$_{1-4}$alkoxysulfonyl, perfluoroC$_{1-4}$alkylsulfonyl, phenylsulfonyl, substituted phenylsufonyl where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 10-camphorsulfonyl, phenylC$_{1-4}$alkylsulfonyl, substituted phenylC$_{1-4}$alkylsulfonyl, C$_{1-4}$alkylsulfinyl, perfluoro C$_{1-4}$alkylsulfinyl, phenylsulfinyl, substituted phenylsufinyl where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, phenylC$_{1-4}$alkylsulfinyl, substituted phenylC$_{1-4}$alkylsulfinyl 1-naphthylsulfonyl, 2-naphthylsulfonyl, substituted naphthylsulfonyl where the naphthyl substituent is selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl, 1-naphthylsulfinyl, 2-naphthylsulfinyl and substituted naphthylsulfinyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl;

$R_1$ is selected from the group consisting of hydrogen and $C_{1-5}$alkyl, $R_2$ is selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino$C_{2-5}$alkyl, amidino$C_{2-5}$alkyl, $C_{1-4}$ alkylamidino$C_{2-5}$alkyl, di$C_{1-4}$alkylamidino$C_{2-5}$alkyl, $C_{1-3}$alkoxy $C_{2-5}$alkyl, phenyl, substituted phenyl where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro, benzyl, phenyl substituted benzyl where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro, hydroxy$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alkyl and $C_{1-5}$alkyl;

p is 0 or 1
B is

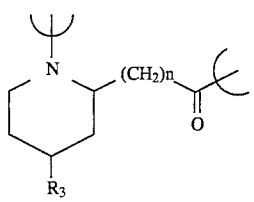

where n is 0–3, R3 is H or $C_{1-5}$alkyl and the carbonyl moiety of B is bound to E;

E is a heterocycle selected from the group consisting of oxazolin-2-yl, oxazol-2-yl, thiazol-2-yl, thiazol-5-yl, thiazol-4-yl, thiazolin-2-yl, benzoxazol-2-yl, benzothiazol-2-yl, 4,5,6,7-tetrahydrobenzothiazol- 2-yl, naphtho[2,1-d]thiazol-2-yl, naphtho[1,2-d]thiazol-2-yl, isothiazol-5-yl, isothiazol-3-yl, and a substituted heterocycle where the substituents are independently selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl, hydroxy or phenyl$C_{1-4}$alkylaminocarbonyl;

or pharmaceutically acceptable salts thereof.

2. The compound of claim 1 wherein:

A is a poly peptide comprised of two amino acids, where the first amino acid is a D or L amino acid, bound via its carboxy terminus to the nitrogen depicted in formula I and is selected from the group consisting of glycine, N-$C_{1-8}$alkylglycine, alanine, 2-azetidinecarboxylic acid, proline, thiazolidine-4-carboxylic acid, 5,5-dimethylthiazolidine-4-carboxylic acid, oxazolidine-4-carboxylic acid, 1-amino-1-cyclo$C_{3-8}$alkylcarboxylic acid, 3-hydroxyproline, 4-hydroxyproline, 3-($C_{1-4}$alkoxy)proline, 4-($C_{1-4}$alkoxy)proline, 3,4-dehydroproline, 2,2-dimethyl-4-thiazolidine carboxylic acid, 2,2-dimethyl-4-oxazolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalanine, [1,2,3,4]-tetrahydroisoquinoline- 1-carboxylic acid, [1,2,3,4]-tetrahydroisoquinoline- 2-carboxylic acid, aspartic acid-4-$C_{1-4}$ alkyl ester and glutamic acid-5-$C_{1-4}$alkyl ester and the second D or L amino acid, is bound to the amino terminus of said first amino acid, and is selected from the group consisting of phenylalanine, 4-benzoylphenylalanine, 4-carboxyphenylalanine, 4-(carboxy $C_{0-2}$alkyl)phenylalanine, substituted phenylalanine where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 3-benzothienylalanine, 4-biphenylalanine, homophenylalanine, octahydroindole-2-carboxylic acid, 2-pyridylalanine, 3-pyridylalanine, 4-thiazolyalanine, 2-thienylalanine, 3-(3-benzothienyl)alanine, 3-thienylalanine, tryptophan, tyrosine, asparagine, 3-tri-$C_{1-4}$alkylsilylalanine, cyclohexylglycine, diphenylglycine, phenylglycine, methionine sulfoxide, methionine sulfone, cyclo$C_{3-8}$alkylalanine, substituted cyclo$C_{3-8}$alkylalanine where the ring substituents are carboxy, $C_{1-4}$alkylcarboxy, $C_{1-4}$alkoxycarbonyl or aminocarbonyl, 2,2-diphenylalanine, 2,2-dicyclohexylalanine, 2-(1-naphthylalanine, 2-(2-naphthylalanine), phenyl substituted phenylalanine where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, aspartic acid, aspartic acid-4-$C_{1-4}$alkyl ester, glutamic acid, glutamic acid-5-$C_{1-4}$alkyl ester and all alpha $C_{1-5}$alkyl derivatives thereof, where the amino terminus of said second amino acid is unsubstituted or monosubstituted with a member of the group consisting of formyl, $C_{1-12}$alkyl, tetrazol-5-yl$C_{1-2}$alkyl, carboxy$C_{1-8}$alkyl, carboalkoxy$C_{1-4}$alkyl, phenyl $C_{1-4}$alkyl, substituted phenyl$C_{1-4}$alkyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1,1-diphenyl$C_{1-4}$alkyl, $C_{1-6}$alkoxycarbonyl, phenyl$C_{1-6}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1,1-diphenyl$C_{1-4}$alkylcarbonyl, $C_{1-4}$alkylsulfonyl, $C_{1-4}$alkoxysulfonyl, perfluoro$C_{1-4}$alkylsulfonyl, phenylsulfonyl, substituted phenylsufonyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 10-camphorsulfonyl, phenyl$C_{1-4}$alkylsulfonyl, substituted phenyl$C_{1-4}$alkylsulfonyl, $C_{1-4}$alkylsulfinyl, perfluoro $C_{1-4}$alkylsulfinyl, phenylsulfinyl, substituted phenylsufinyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, phenyl$C_{1-4}$alkylsulfinyl, substituted phenyl$C_{1-4}$alkylsulfinyl 1-naphthylsulfonyl, 2-naphthylsulfonyl, substituted naphthylsulfonyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1-naphthylsulfinyl, 2-naphthylsulfinyl and substituted naphthylsulfinyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl; and p is 0.

3. The compound of claim 2 wherein:

the first amino acid is an L amino acid selected from the group consisting of glycine, N-$C_{1-8}$alkylglycine, 2-azetidinecarboxylic acid, proline, thiazolidine-4-carboxylic acid, 5,5-dimethylthiazolidine-4-carboxylic acid, oxazolidine-4-carboxylic acid, 1-amino-1-cyclo$C_{3-8}$alkylcarboxylic acid, 3-hydroxyproline, 4-hydroxyproline, 3-($C_{1-4}$alkoxy)proline, 4-($C_{1-4}$alkoxy)proline, 3,4-dehydroproline, 2,2-dimethyl-4-thiazolidine carboxylic acid, 2,2-dimethyl-4-oxazolidine carboxylic acid, pipecolinic acid, valine, methionine, leucine, tert-leucine, isoleucine, phenylalanine, 1-naphthalanine, 2-naphthalanine, 2-thienylalanine, 3-thienylalanine, and the second amino acid is a D amino acid, bound to the amino terminus of said first amino acid, and is selected from the group consisting of phenylalanine, 4-carboxyphenylalanine, 4-(carboxy $C_{0-2}$alkyl)phenylalanine, substituted phenylalanine where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 3-benzothienylalanine, 4-biphenylalanine, homophenylalanine, octahydroindole-2-carboxylic acid, 4-thiazolyalanine, 2-thienylalanine, 3-(3-benzothienyl)alanine, 3-thienylalanine, tryptophan, tyrosine, asparagine, cyclohexylglycine, diphenylglycine, phenylglycine, methionine sulfoxide, methionine sulfone, cyclo$C_{3-8}$alkylalanine, substituted cyclo$C_{3-8}$alkylalanine where the ring substituents are carboxy, $C_{1-4}$alkylcarboxy, $C_{1-4}$alkoxycarbonyl or aminocarbonyl, 2,2-diphenylalanine, 2,2-dicyclohexylalanine, 2-(1-naphthylalanine, 2-( 2-naphthylalanine), phenyl substituted phenylalanine where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, aspartic acid, aspartic acid-4-$C_{1-4}$alkyl ester, glutamic acid, glutamic acid-5-$C_{1-4}$alkyl ester and all alpha $C_{1-5}$alkyl derivatives thereof, where the amino terminus of said second amino acid is unsubstituted or monosubstituted with a member of the group consisting of formyl, $C_{1-12}$alkyl, tetrazol-5-yl$C_{1-2}$alkyl, carboxy$C_{1-8}$alkyl, carboalkoxy$C_{1-4}$alkyl, phenyl $C_{1-4}$alkyl, substituted phenyl$C_{1-4}$alkyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, $C_{1-6}$alkoxycarbonyl, phenyl$C_{1-6}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl; $C_{1-4}$alkylsulfonyl, $C_{1-4}$alkoxysulfonyl, perfluoro$C_{1-4}$alkylsulfonyl, phenylsulfonyl, substituted phenylsufonyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 10-camphorsulfonyl, phenyl$C_{1-4}$alkylsulfonyl, substituted phenyl$C_{1-4}$alkylsulfonyl, $C_{1-4}$alkylsulfinyl, perfluoro $C_{1-4}$alkylsulfinyl, phenylsulfinyl, substituted phenylsufinyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, phenyl$C_{1-4}$alkylsulfinyl, substituted phenyl$C_{1-4}$alkylsulfinyl 1-naphthylsulfonyl, 2-naphthylsulfonyl, substituted naphthylsulfonyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1-naphthylsulfinyl, 2-naphthylsulfinyl and substituted naphthylsulfinyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl.

4. The compound of claim 2 wherein:

the first amino acid is an L amino acid selected from the group consisting of N-$C_{1-8}$alkylglycine, 2-azetidinecarboxylic acid, proline, 1-amino-1-cyclo$C_{3-8}$alkylcarboxylic acid, 3-($C_{1-4}$alkoxy)proline, 4-($C_{1-4}$alkoxy)proline, pipecolinic acid, valine, methionine, leucine, tert-leucine, isoleucine, phenylalanine, 1-naphthalanine, 2-naphthalanine, 2-thienylalanine, 3-thienylalanine, and the second amino acid, is a D amino acid, bound to the amino terminus of said first amino acid, and is selected from the group consisting of phenylalanine, 4-carboxyphenylalanine, 4-(carboxy $C_{0-2}$alkyl)phenylalanine, substituted phenylalanine where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, octahydroindole-2-carboxylic acid, 2-thienylalanine, 3-(3-benzothienyl)alanine, 3-thienylalanine, tryptophan, cyclohexylglycine, diphenylglycine, phenylglycine, methionine sulfoxide, methionine sulfone, cyclo$C_{3-8}$alkylalanine, substituted cyclo$C_{3-8}$alkylalanine where the ring substituents are carboxy, $C_{1-4}$alkylcarboxy, $C_{1-4}$alkoxycarbonyl or aminocarbonyl, 2,2-diphenylalanine, 2,2-dicyclohexylalanine, 2-(1-naphthylalanine), 2-(2-naphthylalanine), phenyl substituted phenylalanine where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, aspartic acid, glutamic acid, and all alpha $C_{1-5}$alkyl derivatives thereof, where the amino terminus of said second amino acid is unsubstituted or monosubstituted with a member of the group consisting of $C_{1-12}$alkyl, tetrazol-5-yl$C_{1-2}$alkyl, carboxy$C_{1-8}$alkyl, carboalkoxy$C_{1-4}$alkyl, $C_{1-6}$alkoxycarbonyl, phenyl$C_{1-6}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, $C_{1-4}$alkylsulfonyl, $C_{1-4}$alkoxysulfonyl, perfluoro$C_{1-4}$alkylsulfonyl, phenylsulfonyl, substituted phenylsufonyl where the phenyl substituents are independently selected from one or more of, $C_{1-4}$alkyl, perfluoro$C_{1-4}$ alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 10-camphorsulfonyl, phenyl$C_{1-4}$alkylsulfonyl, substituted phenyl$C_{1-4}$alkylsulfonyl, $C_{1-4}$alkylsulfinyl, perfluoro $C_{1-4}$alkylsulfinyl, phenylsulfinyl, substituted phenylsufinyl where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, phenyl$C_{1-4}$alkylsulfinyl, substituted phenyl$C_{1-4}$alkylsulfinyl 1-naphthylsulfonyl, 2-naphthylsulfonyl, substituted naphthylsulfonyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl, 1-naphthylsulfinyl, 2-naphthylsulfinyl and substituted naphthylsulfinyl where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl.

5. The compound of claim 4 wherein:

$R_2$ is selected from the group consisting of amino$C_{2-5}$alkyl, guanidino$C_{2-5}$alkyl, amidino$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alkyl, and $C_{1-5}$alkyl.

6. The compound of claim 5 wherein:

E is a heterocycle selected from the group consisting of oxazolin-2-yl, oxazol-2-yl, thiazol-2-yl, thiazol-5-yl, thiazol-4-yl, thiazolin-2-yl, benzoxazol-2-yl, benzothiazol-2-yl, [4,5,6,7]-tetrahydrobenzothiazol-2-yl, naphtho[2,1-d]thiazol-2-yl, naphtho[1,2-d]thiazol-2-yl, isothiazol-5-yl, isothiazol-3-yl, and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl, hydroxy or phenyl$C_{1-4}$alkylaminocarbonyl.

7. The compound of claim 6 wherein:

E is a heterocycle selected from the group consisting of thiazol-2-yl, thiazol-5-yl, thiazol-4-yl, thiazolin-2-yl, benzoxazol-2-yl, benzothiazol-2-yl, [4,5,6,7]-tetrahydrobenzothiazol-2-yl, naphtho[2,1-d]thiazol-2-yl, naphtho[1,2-d]thiazol-2-yl, isothiazol-5-yl, isothiazol-3-yl, and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl or hydroxy.

8. The compound of claim 7 wherein:

E is a heterocycle selected from the group consisting of thiazol-2-yl, thiazol-5-yl, thiazol-4-yl, thiazolin-2-yl, benzothiazol-2-yl, 4,5,6,7-tetrahydrobenzothiazol-2-yl, naphtho[2,1-d]thiazol-2-yl, naphtho[1,2-d]thiazol-2-yl, isothiazol-5-yl, isothiazol-3-yl, and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl or hydroxy.

9. The compound of claim 1, N-methyl-D-phenylalanyl-N-[4-[(aminoiminomethyl)amino]-1S-[(benzothiazol-2-yl)carbonyl]butyl]-L-prolinamide.

10. The compound of claim 1, N-methyl-D-phenylalanyl-N-[5-[(aminoiminomethyl)amino]-1S-[(benzothiazol-2-yl)carbonyl]pentyl]-L-prolinamide.

11. The compound of claim 1, N-methyl-D-phenylalanyl-N-[4-[(aminoiminomethyl)amino]-2S-[(6-methoxycarbonylbenzothiazol-2-yl)carbonyl]butyl]-L-prolinamide.

12. The compound of claim 1, N-methyl-D-phenylalanyl-N-[4-[(aminoiminomethyl)amino]-1S-[(6-carboxybenzothiazol-2-yl)carbonyl]butyl]-L-prolinamide.

13. The compound of claim 1, N-methyl-D-phenylalanyl-N-[4-[(aminoiminomethyl)amino]-1S-[(6-carboxamidobenzothiazol-2-yl)carbonyl]butyl]-L-prolinamide.

14. The compound of claim 1, N-methyl-D-phenylalanyl-N-[4-[(aminoiminomethyl)amino]-1S-[(6-hydroxymethylbenzothiazol-2-yl)carbonyl]butyl]-L-prolinamide.

15. The compound of claim 1, N-methyl-D-phenylalanyl-N-[4-[(aminoiminomethyl)amino]-1S-[(6-fluorobenzothiazol-2-yl)carbonyl]butyl]-L-prolinamide.

16. The compound of claim 1, N-methyl-D-phenylalanyl-N-[4-[(aminoiminomethyl)amino]-1S-[(4-ethoxycarbonylthiazol-2-yl)carbonyl]butyl]-L-prolinamide.

17. The compound of claim 1, N-methyl-D-phenylalanyl-N-[4-[(aminoiminomethyl)amino]-1S-[(4-carboxythiazol-2-yl)carbonyl]butyl]-L-prolinamide.

18. The compound of claim 1, N-methyl-D-phenylalanyl-N-[4-[(aminoiminomethyl)amino]-1S-[(6-methoxybenzothiazol-2-yl)carbonyl]butyl]-L-prolinamide.

19. The compound of claim 1, N-methyl-D-phenylalanyl-N-[4-[(aminoiminomethyl)amino]-1S-[(6-hydroxybenzothiazol-2-yl)carbonyl]butyl]-L-prolinamide.

20. The compound of claim 1, N-methyl-D-cyclohexylalanyl-N-[4-[(aminoiminomethyl)amino]-1S-[(benzothiazol-2-yl)carbonyl]butyl]-L-prolinamide.

21. The compound of claim 1, N-methyl-D-phenylalanyl-N-[4-[(aminoiminomethyl)amino]-1S-[(naptho[2,1-d]thiazol-2-yl)carbonyl]butyl]-L-prolinamide.

22. The compound of claim 1, N-methyl-D-(4-fluorophenyl)alanyl-N-[4-[(aminoiminomethyl)amino]-1S-[(benzothiazol-2-yl)carbonyl]butyl]-L-prolinamide.

23. The compound of claim 1, N-methyl-D-phenylglycyl-N-[4-[(aminoiminomethyl)amino]-1S-[(benzothiazol-2-yl)carbonyl]butyl]-L-prolinamide.

24. The compound of claim 1, N-methyl-D-(diphenyl)alanyl-N-[4-[(aminoiminomethyl)amino]-1S-[(benzothiazol-2-yl)carbonyl]butyl]-L-prolinamide.

25. The compound of claim 1, N-methyl-D-cyclohexylglycyl-N-[4-[(aminoiminomethyl)amino]-1S-[(benzothiazol-2-yl)carbonyl]butyl]-L-prolinamide.

26. The compound of claim 1, N-methyl-D-phenylalanyl-N-[4-[(aminoiminomethyl)amino]-1S-[(4,5,6,7-tetrahydrobenzothiazol-2-yl)carbonyl]butyl]-L-prolinamide.

27. The compound of claim 1, D-phenylalanyl-N-[4-[(aminoiminomethyl)amino]-1S-[(benzothiazol-2-yl)carbonyl]butyl]-L-prolinamide.

28. The compound of claim 1, N-methyl-D-phenylalanyl-N-[4-[(aminoiminomethyl)amino]-1S-[(benzothiazol-2-yl)carbonyl]butyl]-2-piperidinecarboxamide.

29. The compound of claim 1, 2,2-diphenylglycyl-N-[4-[(aminoiminomethyl)amino]-1S-[(benzothiazol-2-yl)carbonyl]butyl]-L-prolinamide.

30. The compound of claim 1, α-methyl-D-phenylalanyl-N-[4-[(aminoiminomethyl)amino]-1S-[(benzothiazol-2-yl)carbonyl]butyl]-L-prolinamide.

31. The compound of claim 1, 1-(N-methylamino)-1-cyclohexylcarbonyl-N-[4-[(aminoiminomethyl)amino]-1S-[(benzothiazol-2-yl)carbonyl]butyl]-L-prolinamide.

32. A pharmaceutical composition comprising pharmaceutically acceptable carrier and an therapeutically effective amount of a compound of claim 1.

33. A pharmaceutical composition comprising pharmaceutically acceptable carrier and an effective amount of a compound of claim 1 necessary to treat thrombin mediated diseases in a mammal.

34. A method for inhibiting thrombin comprising contacting a compound of claim 1 with a medium containing thrombin.

35. A method of claim 34 where the compound contacts the medium via an orthopedic or a surgical device.

36. A method of claim 34 where the medium is mammailian blood.

37. A method of claim 36 where the mammal is a human.

38. A method treating a thrombin mediated disease in a mammal comprising administering an effective amount of a compound of claim 1.

39. A method for inhibiting trypsin comprising contacting a compound of claim 1 with a medium containing trypsin.

40. A method of treating a trypsin related disorder in a mammal comprising administering an effective amount of a compound of claim 1.

* * * * *

UNITED STATES PATENT AND TRADEMARK OFFICE
CERTIFICATE OF CORRECTION

PATENT NO. : 5,523,308  
DATED : June 4, 1996  
INVENTOR(S) : Michael J. Costanzo and Bruce E. Maryanoff It is certified that error appears in the above-identified patent and that said Letters Patent is hereby corrected as shown below:

<u>Columns 23 and 24,</u>
That portion of SCHEME III which reads
"
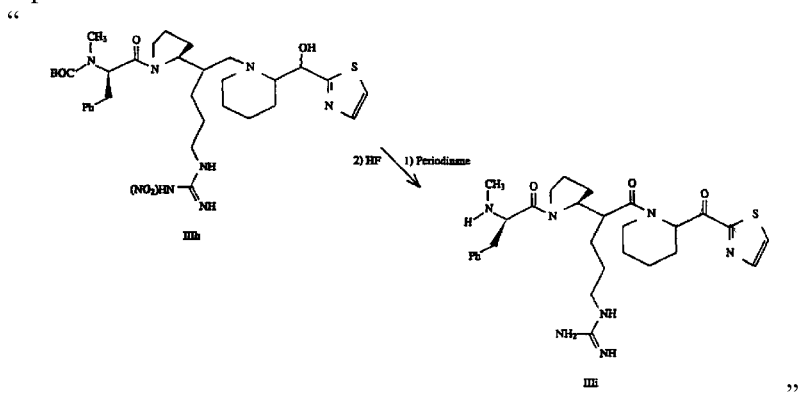
"

should read as
--
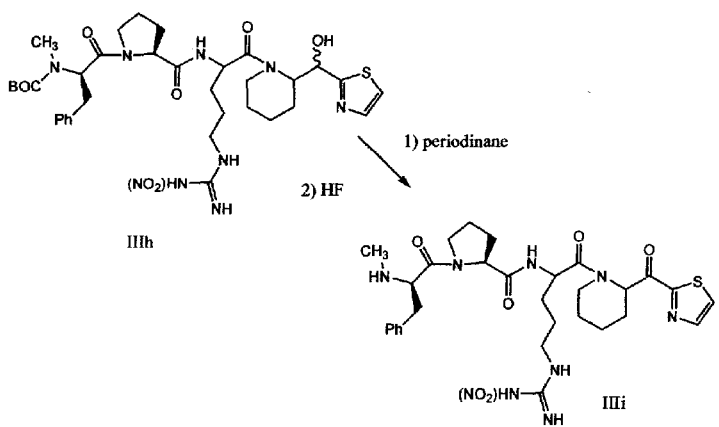
--

Signed and Sealed this

Eighth Day of July, 2003

JAMES E. ROGAN  
*Director of the United States Patent and Trademark Office*